US009476884B2

(12) United States Patent
Ma

(10) Patent No.: US 9,476,884 B2
(45) Date of Patent: Oct. 25, 2016

(54) HYBRIDIZATION- INDEPENDENT LABELING OF REPETITIVE DNA SEQUENCE IN HUMAN CHROMOSOMES

(71) Applicant: University of Massachusetts, Boston, MA (US)

(72) Inventor: Hanhui Ma, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 14/505,927

(22) Filed: Oct. 3, 2014

(65) Prior Publication Data

US 2015/0099269 A1 Apr. 9, 2015

Related U.S. Application Data

(60) Provisional application No. 61/887,017, filed on Oct. 4, 2013.

(51) Int. Cl.
*G01N 33/58* (2006.01)
*C12N 9/22* (2006.01)

(52) U.S. Cl.
CPC ............... *G01N 33/582* (2013.01); *C12N 9/22* (2013.01); *C07K 2319/60* (2013.01); *C07K 2319/80* (2013.01)

(58) Field of Classification Search
CPC .................................................... G01N 33/582
See application file for complete search history.

(56) References Cited

U.S. PATENT DOCUMENTS

| | | | | |
|---|---|---|---|---|
| 3,817,837 | A | 6/1974 | Rubenstein | 435/7.9 |
| 3,850,752 | A | 11/1974 | Schuurs et al. | 435/7.93 |
| 3,939,350 | A | 2/1976 | Kronick et al. | 250/365 |
| 3,996,345 | A | 12/1976 | Ullman et al. | 436/537 |
| 4,275,149 | A | 6/1981 | Litman et al. | 435/7.91 |
| 4,277,437 | A | 7/1981 | Maggio | 422/401 |
| 4,366,241 | A | 12/1982 | Tom et al. | 435/7.91 |
| 6,514,693 | B1 | 2/2003 | Lansdorp | 435/6.13 |
| 8,586,526 | B2 * | 11/2013 | Gregory | C12N 15/62 435/23 |
| 2012/0270273 | A1 | 10/2012 | Zhang et al. | 435/91.52 |

FOREIGN PATENT DOCUMENTS

| | | | |
|---|---|---|---|
| EP | 2206723 | 12/2010 | |
| EP | 2392208 | 12/2011 | |
| WO | WO/01/83732 | 11/2001 | |
| WO | WO 2010/079430 * | 7/2010 | C07K 14/415 |
| WO | WO 2011/146121 A | 11/2011 | |
| WO | WO 2011/146121 B | 11/2011 | |
| WO | WO 2011/154393 | 12/2011 | |
| WO | WO/2012/138939 | 10/2012 | |

OTHER PUBLICATIONS

Alexandrov, et al., "Chromosome-Specific Alpha Satellites: Two Distinct Families on Human Chromosome 18." *Genomics*, 11(1):15-23 (1991).

Antonarakis, et al., "Chromosome 21 and Down Syndrome: From Genomics to Pathophysiology." *Nat Rev Genet*, 5(10):725-738 (2004).

Baker, "Gene-Editing Nucleases." *Nat Methods*, 9(1):23-26 (2012).

Boch, et al., "Breaking the Code of DNA Binding Specificity of TAL-Type III Effectors." *Science*, 326(5959):1509-1512 (2009).

Boch and Bonas, "Xanthomonas AvrBs3 Family-Type III Effectors: Discovery and Function." *Annu Rev Phytopathol*, 48:419-436 (2010).

Bodnar, et al., "Extension of Life-Span by Introduction of Telomerase into Normal Human Cells." *Science*, 279(5349):349-352 (1998).

Bogdanove and Voytas "TAL Effectors: Customizable Proteins for DNA Targeting." *Science*, 333(6051):1843-1846 (2011).

Brind'Amour and Lansdorp "Analysis of Repetitive DNA in Chromosomes by Flow Cytometry." *Nat Methods*, 8(6):484-486 (2011).

Broccoli, et al., "Human Telomeres Contain Two Distinct Myb-Related Proteins, TRF1 and TRF2." *Nat Genet*, 17(2):231-235 (1997).

Bryan, et al., "Telomere Length Dynamics in Telomerase-Positive Immortal Human Cell Populations." *Exp Cell Res*, 239(2):370-378 (1998).

Bultmann, et al., "Targeted Transcriptional Activation of Silent Oct4 Pluripotency Gene by Combining Designer TALES and Inhibition of Epigenetic Modifiers." *Nucleic Acids Res*, 40(12):5368-5377 (2012).

Choo, et al., "Identification of Two Distinct Subfamilies of Alpha Satellite DNA That Are Highly Specific for Human Chromosome 15." *Genomics*, 7(2):143-151 (1990).

Crabbe, et al., "Human Telomeres Are Tethered to the Nuclear Envelope During Postmitotic Nuclear Assembly." *Cell Rep*, 2(6):1521-1529 (2012).

Crowe, et al., "Objective Measurement of Surfactant Irritation by Fiber Optic Spectroscopy." *Contact Dermatitis*, 19(3):192-194 (1988).

Deng, et al., "Structural Basis for Sequence-Specific Recognition of DNA by TAL Effectors." *Science*, 335(6069):720-723 (2012).

DeVos, et al., "Four-Dimensional Telomere Analysis in Recordings of Living Human Cells Acquired with Controlled Light Exposure Microscopy." *J Microsc*, 238(3):254-264 (2010).

Gygi, et al., "Use of Fluorescent Sequence-Specific Polyamides to Discriminate Human Chromosomes by Microscopy and Flow Cytometry." *Nucleic Acids Res*, 30(13):2790-2799 (2002).

(Continued)

*Primary Examiner* — Amber D Steele
(74) *Attorney, Agent, or Firm* — Medlen & Carroll, LLP

(57) ABSTRACT

The present invention discloses a transcription activator-like effector-based strategy, termed "TALEColor", for labeling specific repetitive DNA sequences in human chromosomes. TALEs were custom designed for human telomeric repeats and fused with any of numerous fluorescent proteins (FPs). TALE-telomere-FP fusion proteins were used to detect telomeric sequence in both living cells and fixed cells. Using human cells with different average telomere lengths, TALE-Color signals correlated positively with telomere length. TALEs were also designed to detect centromeric sequences unique to specific chromosomes, enabling localization of these specific human chromosomes in live cells. These methods may have significant potential both for basic chromosome and genome research as well as in clinical applications.

32 Claims, 20 Drawing Sheets

(56) References Cited

OTHER PUBLICATIONS

Henderson, et al., "Location of Ribosomal DNA in the Human Chromosome Complement." *Proc Natl Acad Sci U S A*, 69(11):3394-3398 (1972).

Huang, et al., "Heritable Gene Targeting in Zebrafish Using Customized TALENs." *Nat Biotechnol*, 29(8):699-700 (2011).

Jacobson, et al., "RNA traffic and localization reported by fluorescence cytochemistry in living cells." In: mRNA Formation and Function. Richter, J. D., ed. Academic Press, NY, pp. 341-359 (1997).

Janssen and Medema "Genetic Instability: Tipping the Balance." *Oncogene*, 32(38):4459-4470 (2013).

Jegou, et al., "Dynamics of Telomeres and Promyelocytic Leukemia Nuclear Bodies in a Telomerase-Negative Human Cell Line." *Mol Biol Cell*, 20(7):2070-2082 (2009).

Kim, et al., "Specific Association of Human Telomerase Activity with Immortal Cells and Cancer." *Science*, 266(5193):2011-2015 (1994).

Krutilina, et al., "A Negative Regulator of Telomere-Length Protein TRF1 Is Associated with Interstitial (TTAGGG)n Blocks in Immortal Chinese Hamster Ovary Cells." *Biochem Biophys Res Commun*, 280(2):471-475 (2001).

Lindhout, et al., "Live Cell Imaging of Repetitive DNA Sequences Via Gfp-Tagged Polydactyl Zinc Finger Proteins." *Nucleic Acids Res*, 35(16):e107 (2007).

Ma, et al., "A Highly Efficient Multifunctional Tandem Affinity Purification Approach Applicable to Diverse Organisms." *Mol Cell Proteomics*, 11(8):501-511 (2012).

Mahfouz, et al., "De Novo-Engineered Transcription Activator-Like Effector (TALE) Hybrid Nuclease with Novel DNA Binding Specificity Creates Double-Strand Breaks." *Proc Natl Acad Sci U S A*, 108(6):2623-2628 (2011).

Mak, et al., "The Crystal Structure of TAL Effector Pthxol Bound to Its DNA Target." *Science*, 335(6069):716-719 (2012).

Maniatis, et al., "Regulation of Inducible and Tissue-Specific Gene Expression." *Science*, 236(4806):1237-1245 (1987).

Meckler, et al., "Quantitative Analysis of TALE-DNA Interactions Suggests Polarity Effects." *Nucleic Acids Res*, 41(7):4118-4128 (2013).

Miller, et al., "A TALE Nuclease Architecture for Efficient Genome Editing." *Nat Biotech*, 29(2):143-148 (2011).

Mirkin "Expandable DNA Repeats and Human Disease." *Nature*, 447(7147):932-940 (2007).

Molenaar, et al., "Visualizing Telomere Dynamics in Living Mammalian Cells Using PNA Probes." *Embo J*, 22(24):6631-6641 (2003).

Morbitzer, et al., "Regulation of Selected Genome Loci Using De Novo-Engineered Transcription Activator-Like Effector (TALE)-Type Transcription Factors." *Proc Natl Acad Sci U S A*, 107(50):21617-21622 (2010).

Moscou and Bogdanove "A Simple Cipher Governs DNA Recognition by TAL Effectors." *Science*, 326(5959):1501 (2009).

Ouellette, et al., "Telomerase Activity Does Not Always Imply Telomere Maintenance." *Biochem Biophys Res Commun*, 254(3):795-803 (1999).

Politz, et al., "Diffusion-Based Transport of Nascent Ribosomes in the Nucleus." *Mol Biol Cell*, 14(12):4805-4812 (2003).

Sander, et al., "Targeted Gene Disruption in Somatic Zebrafish Cells Using Engineered TALENs." *Nat Biotechnol*, 29(8):697-698 (2011).

Sambrook, J. et al., In: "Molecular Cloning: A Laboratory Manual," 2nd ed., Cold Spring Harbor laboratory Press, New York, pp. , pp. 7.39-7.52 (1989).

Sambrook, J. et al., In: "Molecular Cloning: A Laboratory Manual," 2nd ed., Cold Spring Harbor laboratory Press, New York, pp. 9.31-9.58 (1989).

Sambrook, J. et al., In: "Molecular Cloning: A Laboratory Manual," 2nd ed., Cold Spring Harbor laboratory Press, New York, pp. 16.7-16.8 (1989).

Sanjana, et al., "A Transcription Activator-Like Effector Toolbox for Genome Engineering." *Nat Protoc*, 7(1):171-192 (2012).

Solovjeva, et al., "Characterization of Telomeric Repeats in Metaphase Chromosomes and Interphase Nuclei of Syrian Hamster Fibroblasts." *Mol Cytogenet*, 5(1):37 (2012).

Takai, et al., "In Vivo Stoichiometry of Shelterin Components." *J Biol Chem*, 285(2):1457-1467 (2010).

Uetake, et al., "Cell Cycle Progression and De Novo Centriole Assembly after Centrosomal Removal in Untransformed Human Cells." *J Cell Biol*, 176(2):173-182 (2007).

Vaijayanthi, et al., "Progress and Prospects of Pyrrole-Imidazole Polyamide-Fluorophore Conjugates as Sequence-Selective DNA Probes." *Chembiochem*, 13(15):2170-2185 (2012).

Vissel and Choo "Human Alpha Satellite DNA—Consensus Sequence and Conserved Regions." *Nucleic Acids Res*, 15(16):6751-6752 (1987).

Wang, et al., "Rapid Telomere Motions in Live Human Cells Analyzed by Highly Time-Resolved Microscopy." *Epigenetics Chromatin*, 1(1):4 (2008).

Waye and Willard "Nucleotide Sequence Heterogeneity of Alpha Satellite Repetitive DNA: A Survey of Alphoid Sequences from Different Human Chromosomes." *Nucleic Acids Res*, 15(18):7549-7569 (1987).

Willard and Waye "Hierarchical Order in Chromosome-Specific Human Alpha Satellite DNA." *Trends in Genetics*, 3:192-198 (1987).

Zhang, et al., "Efficient Construction of Sequence-Specific TAL Effectors for Modulating Mammalian Transcription." *Nat Biotech*, 29(2):149-153 (2011).

Abbott Molecular. "CEP Probes." A: https://www.abbottmolecular.com/us/products/analyte-specific-reagents/Centromere-CEP-probes.html. Copyright © 2013 Abbott Laboratories. Abbott Park, Illinois, U.S.A.

Abbott Molecular. "CEP Probes." B: https://www.abbottmolecular.com/us/products/analyte-specific-reagents/Centromere-CEP-probes.html. Copyright © 2013 Abbott Laboratories. Abbott Park, Illinois, U.S.A.

Dako, "Telomere PNA Kit/FITC for Flow Cytometry." Dated Feb. 19, 2007.

Gall and Pardue, "Formation and Detection of RNA-DNA Hybrid Molecules in Cytological Preparations." *Proc Natl Acad Sci U S A*, 63(2):378-383 (1969).

Scholze and Streubel, "TAL Effectors from Xanthomonas: Design of a Programmable DNA-Binding Specificity." *Bulletin of Insectology* 64 (Supplement):S279-S280 (2011).

Sugimoto, et al., "Centromere/kinetochore localization of human centromere protein A (CENP-A) exogenously expressed as a fusion to green fluorescent protein." Cell structure and Function, 25:253 (2000).

Zhang, et al., "Programmable Sequence-Specific Transcriptional Regulation of Mammalian Genome Using Designer TAL Effectors." PubMed version of *Nat Biotech*, 29(2):149-153 (2011).

* cited by examiner

A

B

A

B

A

B

TALE-TelR06 (SEQ ID NO: 2):

MATTHMGSGIHGVPAAVDLRTLGYSQQQQEKIKPKVRSTVAQHHEALVG
HGFTHAHIVALSQHPAALGTVAVKYQDMIAALPEATHEAIVGVGKQWSG
ARALEALLTVAGELRGPPLQLDTGQLLKIAKRGGVTAVEAVHAWRNALT
GAPLNLTPEQVVAIASNIGGKQALETVQRLLPVLCQAHGLTPEQVVAIAS
NIGGKQALETVQRLLPVLCQAHGLTPEQVVAIASHDGGKQALETVQRLLP
VLCQAHGLTPEQVVAIASHDGGKQALETVQRLLPVLCQAHGLTPEQVVA
IASHDGGRPALESIVAQLSRPDPALAALTNDHLVALACLGGRPALDAVKK
GLPHAPALIKRTNRRIPERTSHRVA

Targeting Sequence: TAACCC (SEQ ID NO: 11)

Figure 10

TALE-TelR09 (SEQ ID NO: 3):

MATTHMGSGIHGVPAAVDLRTLGYSQQQQEKIKPKVRSTVAQHHEALVG HGFTHAHIVALSQHPAALGTVAVKYQDMIAALPEATHEAIVGVGKQWSG ARALEALLTVAGELRGPPLQLDTGQLLKIAKRGGVTAVEAVHAWRNALT GAPLNLTPEQVVAIASNIGGKQALETVQRLLPVLCQAHGLTPEQVVAIAS NIGGKQALETVQRLLPVLCQAHGLTPEQVVAIASHDGGKQALETVQRLLP VLCQAHGLTPEQVVAIASHDGGKQALETVQRLLPVLCQAHGLTPEQVVA IASHDGGKQALETVQRLLPVLCQAHGLTPEQVVAIASNGGGKQALETVQ RLLPVLCQAHGLTPEQVVAIASNIGGKQALETVQRLLPVLCQAHGLTPEQ VVAIASNIGGRPALESIVAQLSRPDPALAALTNDHLVALACLGGRPALDA VKKGLPHAPALIKRTNRRIPERTSHRVA

Targeting Sequence: TAACCCTAA (SEQ ID NO: 12)

Figure 11

TALE-TelR12 (SEQ ID NO: 4):

MATTHMGSGIHGVPAAVDLRTLGYSQQQQEKIKPKVRSTVAQHHEALVG
HGFTHAHIVALSQHPAALGTVAVKYQDMIAALPEATHEAIVGVGKQWSG
ARALEALLTVAGELRGPPLQLDTGQLLKIAKRGGVTAVEAVHAWRNALT
GAPLNLTPEQVVAIASNIGGKQALETVQRLLPVLCQAHGLTPEQVVAIAS
NIGGKQALETVQRLLPVLCQAHGLTPEQVVAIASHDGGKQALETVQRLLP
VLCQAHGLTPEQVVAIASHDGGKQALETVQRLLPVLCQAHGLTPEQVVA
IASHDGGKQALETVQRLLPVLCQAHGLTPEQVVAIASNGGGKQALETVQ
RLLPVLCQAHGLTPEQVVAIASNIGGKQALETVQRLLPVLCQAHGLTPEQ
VVAIASNIGGKQALETVQRLLPVLCQAHGLTPEQVVAIASHDGGKQALET
VQRLLPVLCQAHGLTPEQVVAIASHDGGKQALETVQRLLPVLCQAHGLT
PEQVVAIASHDGGRPALESIVAQLSRPDPALAALTNDHLVALACLGGRPA
LDAVKKGLPHAPALIKRTNRRIPERTSHRVA

Targeting Sequence: TAACCCTAACCC (SEQ ID NO: 13)

Figure 12

TALE-TelR15 (SEQ ID NO: 5):

MATTHMGSGIHGVPAAVDLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPEQVVAIASNIGGKQALETVQRLLPVLCQAHGLTPEQVVAIASNIGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNIGGKQALETVQRLLPVLCQAHGLTPEQVVAIASNIGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNIGGKQALETVQRLLPVLCQAHGLTPEQVVAIASNIGGRPALESIVAQLSRPDPALAALTNDHLVALACLGGRPALDAVKKGLPHAPALIKRTNRRIPERTSHRVA

Targeting Sequence: TAACCCTAACCCTAA (SEQ ID NO: 14)

Figure 13

TALE-TelR20 (SEQ ID NO: 6):

MATTHMGSGIHGVPAAVDLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPEQVVAIASNIGGKQALETVQRLLPVLCQAHGLTPEQVVAIASNIGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNIGGKQALETVQRLLPVLCQAHGLTPEQVVAIASNIGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNIGGKQALETVQRLLPVLCQAHGLTPEQVVAIASNIGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNIGGRPALESIVAQLSRPDPALAALTNDHLVALACLGGRPALDAVKKGLPHAPALIKRTNRRIPERTSHRVA

Targeting Sequence: TAACCCTAACCCTAACCCTA (SEQ ID NO: 15)

Figure 14

TALE-TelL20 (SEQ ID NO: 7):

VDLRTLGYSQQQQEKIKPKVRSTVAQHHEALVGHGFTHAHIVALSQHPA
ALGTVAVKYQDMIAALPEATHEAIVGVGKQWSGARALEALLTVAGELR
GPPLQLDTGQLLKIAKRGGVTAVEAVHAWRNALTGAPLNLTPEQVVAIA
SNIGGKQALETVQRLLPVLCQAHGLTPEQVVAIASNHGGKQALETVQRLL
PVLCQAHGLTPEQVVAIASNHGGKQALETVQRLLPVLCQAHGLTPEQVV
AIASNHGGKQALETVQRLLPVLCQAHGLTPEQVVAIASNGGGKQALETV
QRLLPVLCQAHGLTPEQVVAIASNGGGKQALETVQRLLPVLCQAHGLTPE
QVVAIASNIGGKQALETVQRLLPVLCQAHGLTPEQVVAIASNHGGKQALE
TVQRLLPVLCQAHGLTPEQVVAIASNHGGKQALETVQRLLPVLCQAHGL
TPEQVVAIASNHGGKQALETVQRLLPVLCQAHGLTPEQVVAIASNGGGK
QALETVQRLLPVLCQAHGLTPEQVVAIASNGGGKQALETVQRLLPVLCQ
AHGLTPEQVVAIASNIGGKQALETVQRLLPVLCQAHGLTPEQVVAIASNH
GGKQALETVQRLLPVLCQAHGLTPEQVVAIASNHGGKQALETVQRLLPV
LCQAHGLTPEQVVAIASNHGGKQALETVQRLLPVLCQAHGLTPEQVVAI
ASNGGGKQALETVQRLLPVLCQAHGLTPEQVVAIASNGGGKQALETVQR
LLPVLCQAHGLTPEQVVAIASNIGGRPALESIVAQLSRPDPALAALTNDHL
VALACLGGRPALDAVKKGLPHAPALIKRTNRRIPERTSHRVA

Targeting Sequence: TAGGGTTAGGGTTAGGGTTA (SEQ ID NO:16)

Figure 15

TALE-PanCen (SEQ ID NO: 8):

VDLRTLGYSQQQQEKIKPKVRSTVAQHHEALVGHGFTHAHIVALSQHPA
ALGTVAVKYQDMIAALPEATHEAIVGVGKQWSGARALEALLTVAGELR
GPPLQLDTGQLLKIAKRGGVTAVEAVHAWRNALTGAPLNLTPEQVVAIA
SNIGGKQALETVQRLLPVLCQAHGLTPEQVVAIASNHGGKQALETVQRLL
PVLCQAHGLTPEQVVAIASNIGGKQALETVQRLLPVLCQAHGLTPEQVVA
IASHDGGKQALETVQRLLPVLCQAHGLTPEQVVAIASNIGGKQALETVQR
LLPVLCQAHGLTPEQVVAIASNHGGKQALETVQRLLPVLCQAHGLTPEQ
VVAIASNIGGKQALETVQRLLPVLCQAHGLTPEQVVAIASNIGGKQALET
VQRLLPVLCQAHGLTPEQVVAIASNHGGKQALETVQRLLPVLCQAHGLT
PEQVVAIASHDGGKQALETVQRLLPVLCQAHGLTPEQVVAIASNIGGKQA
LETVQRLLPVLCQAHGLTPEQVVAIASNGGGKQALETVQRLLPVLCQAH
GLTPEQVVAIASNGGGKQALETVQRLLPVLCQAHGLTPEQVVAIASHDG
GKQALETVQRLLPVLCQAHGLTPEQVVAIASNGGGKQALETVQRLLPVL
CQAHGLTPEQVVAIASHDGGKQALETVQRLLPVLCQAHGLTPEQVVAIAS
NIGGKQALETVQRLLPVLCQAHGLTPEQVVAIASNHGGKQALETVQRLLP
VLCQAHGLTPEQVVAIASNIGGRPALESIVAQLSRPDPALAALTNDHLVAL
ACLGGRPALDAVKKGLPHAPALIKRTNRRIPERTSHRVA

Targeting Sequence: TAGACAGAAGCATTCTCAGA (SEQ ID NO: 17)

Figure 16

TALE-Cen15 (SEQ ID NO: 9)

VDLRTLGYSQQQQEKIKPKVRSTVAQHHEALVGHGFTHAHIVALSQHPA
ALGTVAVKYQDMIAALPEATHEAIVGVGKQWSGARALEALLTVAGELR
GPPLQLDTGQLLKIAKRGGVTAVEAVHAWRNALTGAPLNLTPEQVVAIA
SHDGGKQALETVQRLLPVLCQAHGLTPEQVVAIASNIGGKQALETVQRLL
PVLCQAHGLTPEQVVAIASHDGGKQALETVQRLLPVLCQAHGLTPEQVV
AIASNGGGKQALETVQRLLPVLCQAHGLTPEQVVAIASNGGGKQALETV
QRLLPVLCQAHGLTPEQVVAIASHDGGKQALETVQRLLPVLCQAHGLTPE
QVVAIASNIGGKQALETVQRLLPVLCQAHGLTPEQVVAIASNIGGKQALE
TVQRLLPVLCQAHGLTPEQVVAIASNNGGKQALETVQRLLPVLCQAHGL
TPEQVVAIASNIGGKQALETVQRLLPVLCQAHGLTPEQVVAIASNGGGKQ
ALETVQRLLPVLCQAHGLTPEQVVAIASNGGGKQALETVQRLLPVLCQA
HGLTPEQVVAIASHDGGKQALETVQRLLPVLCQAHGLTPEQVVAIASNG
GGKQALETVQRLLPVLCQAHGLTPEQVVAIASNIGGKQALETVQRLLPVL
CQAHGLTPEQVVAIASHDGGKQALETVQRLLPVLCQAHGLTPEQVVAIAS
NNGGKQALETVQRLLPVLCQAHGLTPEQVVAIASNNGGKQALETVQRLL
PVLCQAHGLTPEQVVAIASNIGGRPALESIVAQLSRPDPALAALTNDHLVA
LACLGGRPALDAVKKGLPHAPALIKRTNRRIPERTSHRVA

Targeting Sequence: TCACTTCAAGATTCTACGGA (SEQ ID NO: 18)

Figure 17

TALE-Cen18 (SEQ ID NO: 10):

VDLRTLGYSQQQQEKIKPKVRSTVAQHHEALVGHGFTHAHIVALSQHPA
ALGTVAVKYQDMIAALPEATHEAIVGVGKQWSGARALEALLTVAGELR
GPPLQLDTGQLLKIAKRGGVTAVEAVHAWRNALTGAPLNLTPEQVVAIA
SNGGGKQALETVQRLLPVLCQAHGLTPEQVVAIASNNGGKQALETVQRL
LPVLCQAHGLTPEQVVAIASNIGGKQALETVQRLLPVLCQAHGLTPEQVV
AIASNIGGKQALETVQRLLPVLCQAHGLTPEQVVAIASHDGGKQALETVQ
RLLPVLCQAHGLTPEQVVAIASHDGGKQALETVQRLLPVLCQAHGLTPEQ
VVAIASNIGGKQALETVQRLLPVLCQAHGLTPEQVVAIASHDGGKQALET
VQRLLPVLCQAHGLTPEQVVAIASHDGGKQALETVQRLLPVLCQAHGLT
PEQVVAIASNNGGKQALETVQRLLPVLCQAHGLTPEQVVAIASNGGGKQ
ALETVQRLLPVLCQAHGLTPEQVVAIASNGGGKQALETVQRLLPVLCQA
HGLTPEQVVAIASNGGGKQALETVQRLLPVLCQAHGLTPEQVVAIASNG
GGKQALETVQRLLPVLCQAHGLTPEQVVAIASNNGGKQALETVQRLLPV
LCQAHGLTPEQVVAIASNIGGKQALETVQRLLPVLCQAHGLTPEQVVAIA
SNIGGKQALETVQRLLPVLCQAHGLTPEQVVAIASNNGGKQALETVQRLL
PVLCQAHGLTPEQVVAIASNNGGRPALESIVAQLSRPDPALAALTNDHLV
ALACLGGRPALDAVKKGLPHAPALIKRTNRRIPERTSHRVA

Targeting Sequence: TTGAACCACCGTTTTGAAGG (SEQ ID NO: 19)

Figure 18

HYBRIDIZATION- INDEPENDENT LABELING OF REPETITIVE DNA SEQUENCE IN HUMAN CHROMOSOMES

FIELD OF INVENTION

The present invention is related to compositions and methods for detecting sequence-specific chromosomal sites. For example, such methods and compositions are useful to detect repeated nucleic acid sequences in chromosomal telomeres and/or centromeres. The invention is also related to labeled Transcription activator-like effectors that might be used as probes to detect DNA sequences in cell preparations without DNA denaturation.

BACKGROUND

The presence or localization of specific DNA sequences in human chromosomes can be detected in chemically fixed cells by In Situ Hybridization (ISH), a method based on complementary base-pairing between the target sequence and an oligonucleotide probe that carries a detectable tag (e.g., a fluorescent dye). However, the DNA hybridization protocol is time-consuming and the oligonucleotide probes are costly. Furthermore, ISH is normally applicable to fixed cells and is challenging to apply in live cells when desired due to the stringent conditions of hybridization which are not physiological. Live cell imaging would be required for observation of the intranuclear movements or rearrangements of a given chromosomal region that contains the array of DNA sequence(s) being targeted, and would allow investigation of how such movements or rearrangement may result in human diseases.

"TALEN" ("Transcriptional Activator-Like Effector Nuclease") is a recently introduced method that allows specific DNA sequences to be targeted by a molecular mechanism that does not involve pairing between complementary bases in the DNA and the probe. Instead, unique arrays of amino acids are incorporated into a peptide to confer upon it a high specificity for binding to a particular DNA sequence. To date, the major application of this method has been to site-specifically direct the cutting of DNA inside cells to allow the deletion/insertion/mutation, at the cut site, of a new DNA element ("genomic engineering"). This is achieved by tethering to the peptide a DNA-cutting enzyme (the "Effector Nuclease" in the method's acronym) whose action is thus directed specifically to that DNA site.

What is need in the art are compositions and methods to detect chromosomal sites by direct binding of labeled protein sequences that are devoid of nuclease activity.

SUMMARY OF THE INVENTION

The present invention is related to compositions and methods for detecting chromosomal loci in a sequence-dependent manner. For example, such methods and compositions are useful to detect repeated nucleic acid sequences in chromosomal telomeres and/or centromeres. The invention is also related to labeled Transcription activator-like effectors that might be used as probes to detect DNA sequences in cell preparations without DNA denaturation.

In one embodiment, the present invention contemplates a transcriptional activator-like effector (TALE) protein comprising a plurality of repeat amino acid sequences, wherein said TALE protein is not coupled to a nuclease. In one embodiment, the repeat amino acid sequences include, but are not limited to,

```
                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,

                                   (SEQ ID NO: 25)
LTPEQVVAIASNGGGKQALETVQRLLPVLCQAHG,

                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,

                                    (SEQ ID NO: 1)
LTPEQVVAIASHDGGKQALETVQRLLPVLCQAHG,

                                   (SEQ ID NO: 25)
LTPEQVVAIASNGGGKQALETVQRLLPVLCQAHG,

                                   (SEQ ID NO: 24)
LTPEQVVAIASNIGGKQALETVQRLLPVLCQAHG,
and

                                   (SEQ ID NO: 26)
LTPEQVVAIASNIGG.
```

In one embodiment, the TALE protein comprises SEQ ID NO:2. In one embodiment, the TALE protein comprises SEQ ID NO:3. In one embodiment, the TALE protein comprises SEQ ID NO:4. In one embodiment, the TALE protein comprises SEQ ID NO:5. In one embodiment, the TALE protein comprises SEQ ID NO:6. In one embodiment, the TALE protein comprises SEQ ID NO:7. In one embodiment, the TALE protein has specific affinity for a telomere nucleic acid target sequence.

In one embodiment, the present invention contemplates a transcriptional activator-like effector (TALE) protein comprising a plurality of repeat amino acid sequences, wherein said TALE protein is not coupled to a nuclease. In one embodiment, the plurality of amino acid sequences are selected from the group consisting of

```
                                   (SEQ ID NO: 25)
LTPEQVVAIASNGGGKQALETVQRLLPVLCQAHG,

                                   (SEQ ID NO: 27)
LTPEQVVAIASNHGGKQALETVQRLLPVLCQAHG,

                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,

                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,

                                   (SEQ ID NO: 27)
LTPEQVVAIASNHGGKQALETVQRLLPVLCQAHG,

                                   (SEQ ID NO: 25)
LTPEQVVAIASNGGGKQALETVQRLLPVLCQAHG,

                                   (SEQ ID NO: 25)
LTPEQVVAIASNGGGKQALETVQRLLPVLCQAHG,
```

-continued (SEQ ID NO: 27)
LTPEQVVAIASNHGGKQALETVQRLLPVLCQAHG, (SEQ ID NO: 24)
LTPEQVVAIASNIGGKQALETVQRLLPVLCQAHG, (SEQ ID NO: 27)
LTPEQVVAIASNHGGKQALETVQRLLPVLCQAHG,
and (SEQ ID NO: 29)
LTPEQVVAIASNHGG.

In one embodiment, the TALE protein comprises SEQ ID NO:8. In one embodiment, the TALE protein comprises SEQ ID NO:9. In one embodiment, the TALE protein comprises SEQ ID NO:10. In one embodiment, the TALE protein has specific affinity for a centromere nucleic acid target sequence. In one embodiment, the TALE protein is attached to a fluorescent protein. In one embodiment, the fluorescent protein is a green fluorescent protein. In one embodiment, the fluorescent protein is an mCherry protein.

In one embodiment, the present invention contemplates a telomere target nucleic acid sequence including, but not limited to, TAACCC (SEQ ID NO: 11), TAACCCTAA (SEQ ID NO:12), TAACCCTAACCC (SEQ ID NO: 13), TAACCCTAACCCTAA (SEQ ID NO: 14), TAACCCTAACCCTAACCCTA (SEQ ID NO: 15), and TAGGGTTAGGGTTAGGGTTA (SEQ ID NO. 16).

In one embodiment, the present invention contemplates a centromere target nucleic acid sequence including, but not limited to, TAGACAGAAGCATTCTCAGA (SEQ ID NO: 17), TCACTTCAAGATTCTACGGA (SEQ ID NO: 18), TTGAACCACCGTTTTGAAGG (SEQ ID NO:19).

In one embodiment, the present invention contemplates a composition comprising a peptide linked to a fluorescent protein and not attached to a nuclease, wherein said peptide is bound to a telomere target nucleic acid sequence. In one embodiment, the target nucleic acid sequence includes, but is not limited to, TAACCC (SEQ ID NO: 11), TAACCCTAA (SEQ ID NO:12), TAACCCTAACCC (SEQ ID NO: 13), TAACCCTAACCCTAA (SEQ ID NO: 14), TAACCCTAACCCTAACCCTA (SEQ ID NO: 15), and TAGGGTTAGGGTTAGGGTTA (SEQ ID NO. 16). In one embodiment, the peptide includes, but is not limited to, SEQ ID NO:2, SEQ ID NO:3, SEQ ID NO:4, SEQ ID NO:5, SEQ ID NO:6, and SEQ ID NO:7. In one embodiment, the telomere target nucleic acid sequence comprises double stranded deoxyribonucleic acid. In one embodiment, the composition further comprises a live cell. In one embodiment, the composition further comprises a fixed cell.

In one embodiment, the present invention contemplates a composition comprising a peptide linked to a fluorescent protein and not attached to a nuclease, wherein said peptide is bound to a centromere target nucleic acid sequence. In one embodiment, the target nucleic acid sequence includes, but is not limited to, TAGACAGAAGCATTCTCAGA (SEQ ID NO: 17), TCACTTCAAGATTCTACGGA (SEQ ID NO: 18), TTGAACCACCGTTTTGAAGG (SEQ ID NO:19). In one embodiment, the peptide includes, but is not limited to, SEQ ID NO: 8, SEQ ID NO: 9 and SEQ ID NO: 10. In one embodiment, the target nucleic acid sequence is located a human chromosome including, but not limited to, chromosome 15, chromosome 18 and/or chromosome 21. In one embodiment, the centromere target nucleic acid sequence comprises double stranded deoxyribonucleic acid. In one embodiment, the composition further comprises a live cell. In one embodiment, the composition further comprises a fixed cell.

DEFINITIONS

The term "about" as used herein, in the context of any of any assay measurements refers to +/−5% of a given measurement.

The term "affinity" as used herein, refers to any attractive force between substances or particles that causes them to enter into and remain in chemical combination. For example, an inhibitor compound that has a high affinity for a receptor will provide greater efficacy in preventing the receptor from interacting with its natural ligands, than an inhibitor with a low affinity.

The term "derived from" as used herein, refers to the source of a compound or sequence. In one respect, a compound or sequence may be derived from an organism or particular species. In another respect, a compound or sequence may be derived from a larger complex or sequence.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide", refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term "pharmaceutically" or "pharmacologically acceptable", as used herein, refer to molecular entities and compositions that do not produce adverse, allergic, or other untoward reactions when administered to an animal or a human.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

The terms "specific binding" or "specifically binding" when used in reference to the interaction of an nucleic acid and a protein or peptide means that the interaction is dependent upon the presence of a particular structure (i.e., for example, an antigenic determinant or epitope) on a protein.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "functionally equivalent codon", as used herein, refers to different codons that encode the same amino acid. This phenomenon is often referred to as "degeneracy" of the genetic code. For example, six different codons encode the amino acid arginine.

A "variant" of a protein is defined as an amino acid sequence which differs by one or more amino acids from a polypeptide sequence or any homolog of the polypeptide sequence. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs including, but not limited to, DNAStar® software.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively.

A "substitution" results from the replacement of one or more nucleotides or amino acids by different nucleotides or amino acids, respectively.

The term "derivative" as used herein, refers to any chemical modification of a nucleic acid or an amino acid. Illustrative of such modifications would be replacement of hydrogen by an alkyl, acyl, or amino group. For example, a nucleic acid derivative would encode a polypeptide which retains essential biological characteristics.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

As used herein, the term "probe" refers; to any protein, amino acid sequence or amino acid pair, which is capable of attaching to a nucleic acid sequence of interest. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

The term "in operable combination" as used herein, refers to any linkage of nucleic acid sequences in such a manner that a nucleic acid molecule capable of directing the transcription of a given gene and/or the synthesis of a desired protein molecule is produced. Regulatory sequences may be operably combined to an open reading frame including but not limited to initiation signals such as start (i.e., ATG) and stop codons, promoters which may be constitutive (i.e., continuously active) or inducible, as well as enhancers to increase the efficiency of expression, and transcription termination signals.

Transcriptional control signals in eukaryotes comprise "promoter" and "enhancer" elements. Promoters and enhancers consist of short arrays of DNA sequences that interact specifically with cellular proteins involved in transcription. Maniatis, T. et al., *Science* 236:1237 (1987). Promoter and enhancer elements have been isolated from a variety of eukaryotic sources including genes in plant, yeast, insect and mammalian cells and viruses (analogous control elements, i.e., promoters, are also found in prokaryotes). The selection of a particular promoter and enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: *Molecular Cloning: A Laboratory Manual,* 2nd ed., Cold Spring Harbor laboratory Press, New York (1989) pp. 16.7-16.8. A commonly used splice donor and acceptor site is the splice junction from the 16S RNA of SV40.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The terms "binding component", "molecule of interest", "agent of interest", "ligand" or "receptor" as used herein may be any of a large number of different molecules, biological cells or aggregates, and the terms are used interchangeably. Each binding component may be immobilized on a solid substrate and binds to an analyte being detected. Proteins, polypeptides, peptides, nucleic acids (nucleotides, oligonucleotides and polynucleotides), antibodies, ligands, saccharides, polysaccharides, microorganisms such as bacteria, fungi and viruses, receptors, antibiotics, test compounds (particularly those produced by combinatorial chemistry), plant and animal cells, organdies or fractions of each and other biological entities may each be a binding component. Each, in turn, also may be considered as analytes if same bind to a binding component on a chip.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte being measuring. The "binding" interaction may be brief as in the situation where binding causes a chemical reaction to occur. That is typical when the binding component is an enzyme and the analyte is a substrate for the enzyme. Reactions resulting from contact between the binding agent and the analyte are also within the definition of binding for the purposes of the present invention.

The term "luminescence" and/or "fluorescence", as used herein, refers to any process of emitting electromagnetic radiation (light) from an object, chemical and/or compound. Luminescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation. The term "suspected of having", as used herein, refers a medical condition or set of medical conditions (e.g., preliminary symptoms) exhibited by a patient that is insufficient to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

BRIEF DESCRIPTION OF THE FIGURES

FIG. 1A: TALEColor probes were designed to target either strand of the telomere repeat by fusion of various fluorescent proteins at C-terminus.

FIG. 1B: U2OS cells were co-transfected with pairs of TALE-fluorescent proteins and labeling was assessed in the live cells 24 hours later in the appropriate spectral channels of the microscopy system. Top row: TALECerulean-TelL20 (middle left) and TALEVenus-TelR20 (middle right). Middle row: TALEVenus-TelL20 (middle left) and TALECerulean-TelR20 (middle right). Bottom row: TALEVenus-TelL20 (middle left) and TALEmCherry-TelR20 (middle right). The left vertical column of panels are the phase-contrast images and the right column are the two-color overlays respectively. Scale bar, 5 μm.

FIG. 2A: Diagram of TALEGreen-TelL15.

FIG. 2B: U2OS cells were fixed in 90% methanol and incubated with the probe. Shown beneath the diagram are representative images in an interphase and anaphase cell. After exposing fixed cells to the probe, immunostaining was carried out with a TRF-2 antibody followed by a TRITC-labeled secondary antibody. Upper row: probe imaged in both the green and red channels; middle row: TRF2 immunostaining imaged in both channels; bottom row: probe and TRF2 immunostaining imaged in each channel. The left column is phase-contrast images and the right column is both the probe and TRF2 merged onto DAPI staining.

FIG. 2C: U2OS cells in different cell cycle stages were imaged for the probe, TRF2 immunostaining or DAPI, as indicated. Scale bars in A-C are 5 μm.

FIG. 3A: TALE-TelR15 probes were designed with various fused fluorescent proteins as indicated and applied to fixed U2OS cells. Images were captured in the appropriate channels (middle row) and merged with DAPI images (bottom row).

FIG. 3B: A TALE-TelR15 probe with no fused fluorescent protein was produced carrying internal lysine resides labeled with a green dye. The labeling obtained (upper row) was imaged and compared to that with the same TALE carrying fused mCherry (lower row), with the right column representing the respective images overlaid onto DAPI images. Scale bar in both A and B is 5 μm.

FIG. 5A: HeLa 1.3 and HeLa S3 cells cultured either alone or together and then incubated with TALEGreen-TelR15 and imaged Scale bar, 10 μm.

FIG. 5B: Separate coverglass cultures of HeLa 1.3 and HeLa S3 cells were trypsinized, fixed and incubated with TALEGreen-TelR15 together with DNA staining with DAPI or DRAQ5 for the HeLa 1.3 and S3 cells, respectively. The two cell populations were then mixed and imaging flow cytometry was carried out immediately. Single cells were gated by an aspect ratio program in the instrument's software (left panel, middle row). DAPI positive cells (purple) and DRAQ5 positive cells (red) were gated by their intensity (left panel, top row) and their intensity plots are shown in the indicated panels. The DNA intensity plots of the two cell populations (resolved out from the mixture of the two cell lines) are shown in the indicated panels. The scatter plot of TALEGreen-TelR15 signals in all cells is shown in the bottom left panel. These were sorted into DAPI positive (purple) and DRAQ5 positive (red) populations (middle panel in bottom row). The DAPI positive cells were then sorted into distinct levels of telomere labeling: a high level (R1, light green, upper right panel) and a moderate level (R2, dark green, upper right panel). DRAQ5 positive cells with their low level of telomere labeling were sorted in parallel (R3, teal, middle row, right panel).

FIG. 5C: Representative DAPI images for HeLa 1.3 cells not labeled with TALEGreen-TelR15 (left three columns), DAPI positive R1 cells (middle left four columns), DAPI positive R2 cells (middle right four columns), DRAQ5 positive R3 cells (right four columns). BF: brightfield.

FIG. 8A: U2OS cells were transfected with constructs expressing telomere-specific TALE's having different numbers of the oligopeptide repeat ranging from 6 to 20, all fused to Venus. Images were captured (middle row) and merged with DAPI images (bottom row). Scale bar, 5 μm.

FIG. 10 presents one embodiment of a TelR6 binding protein amino acid sequence (SEQ ID NO:2) and associated target sequence (SEQ ID NO: 11). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 11 presents one embodiment of a TelR9 binding protein amino acid sequence (SEQ ID NO:3) and associated target sequence (SEQ ID NO: 12). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 12 presents one embodiment of a TelR12 binding protein amino acid sequence (SEQ ID NO:4) and associated target sequence (SEQ ID NO: 13). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 13 presents one embodiment of a TelR15 binding protein amino acid sequence (SEQ ID NO:5) and associated target sequence (SEQ ID NO: 14). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 14 presents one embodiment of a TelR20 binding protein amino acid sequence (SEQ ID NO:6) and associated target sequence (SEQ ID NO: 15). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 15 presents one embodiment of a TelL20 binding protein amino acid sequence (SEQ ID NO:7) and associated target sequence (SEQ ID NO: 16). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 16 presents one embodiment of a PanCen binding protein amino acid sequence (SEQ ID NO:8) and associated target sequence (SEQ ID NO: 17). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 17 presents one embodiment of a TALE-Cen15-mVenus amino acid sequence (SEQ ID NO:9) and associated target sequence (SEQ ID NO: 18). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

FIG. 18 presents one embodiment of a TALE-Cen18-mVenus amino acid sequence (SEQ ID NO:10) and associated target sequence (SEQ ID NO: 19). Unique amino acid binding pairs are annotated with specific color codes and a dotted underline. Gold: NI amino acid binding pair specific for a target sequence adenosine residue. Red: NG amino acid binding pair specific for a target sequence thymidine residue. Blue: HD amino acid binding pair specific for a target sequence cytosine residue. Green: NH amino acid binding pair specific for a target sequence guanosine residue.

DETAILED DESCRIPTION OF THE INVENTION

Figure 1:
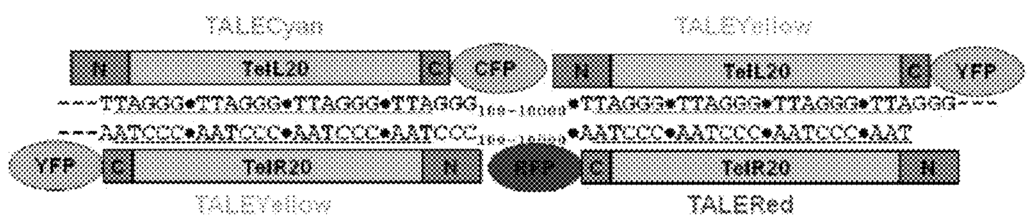
FIG. 1 presents an illustration of telomere detection by TALEColor.
Figure 1:
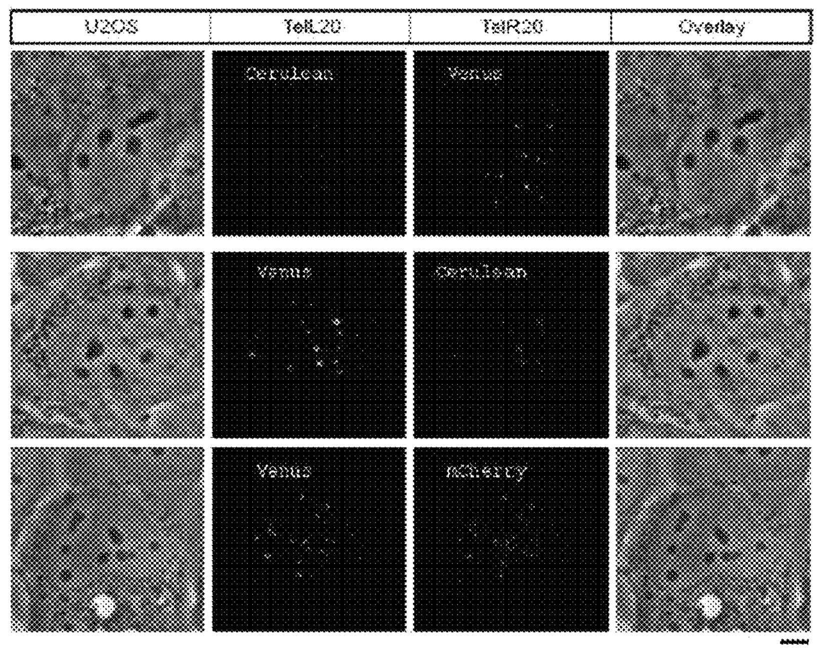

The present invention is related to compositions and methods for detecting chromosomal sites. For example, such methods and compositions are useful to detect repeated nucleic acid sequences in chromosomal telomeres and/or centromeres. The invention is also related to labeled Transcription activator-like effectors that might be used as probes to detect DNA sequences in cell preparations without DNA denaturation.

In one embodiment, the present invention contemplates a composition comprising at least one fluorescent TALE protein capable of binding to a double stranded DNA sequence. In one embodiment, the double stranded DNA sequence comprises a telomeric sequence. In one embodiment, the double stranded DNA sequence comprises a centromeric sequence. In one embodiment, the double stranded DNA sequence comprises at least one a repeated nucleic acid sequence.

I. Transcription Activator-Like Effectors

The most distinctive characteristic of transcription activator like effector (TALE) is a central repeat domain containing between 1.5 and 33.5 repeats that are usually 34 residues in length (the C-terminal repeat is generally shorter and referred to as a "half repeat"). Boch et al., "XanthomonasAvrBs3 Family-Type III Effectors: Discovery and Function" *Annual Review of Phytopathology* 48: 419-36 (2010).

A typical repeat sequence is LTPEQVVAIASHDGGKQALETVQRLLPVLCQAHG (SEQ ID NO:1), but the residues at the 12th and 13th positions are hypervariable where these two amino acids are also known as the repeat variable diresidue (RVD). A simple relationship has been identified between the identity of the RVD in sequential repeats and sequential DNA bases in the TAL effector's target site. Moscou et al., "A simple cipher governs DNA recognition by TAL effectors" *Science* 326:1501 (2009); and Boch et al., "Breaking the code of DNA binding specificity of TAL-type III effectors". *Science* 326: 1509-1512 (2009). The experimentally validated code between RVD sequence and target DNA base can be expressed as NI=A, HD=C, NG=T, NN=R (G or A), and NS=N (A, C, G, or T). Further studies has shown that the RVD NK can target G, although TAL effector nucleases (TALENs) that exclusively use NK instead of NN to target G can be less active. Morbitzer et al., "Regulation of selected genome loci using de novo-engineered transcription activator-like effector (TALE)-type transcription factors" *Proceedings of the National Academy of Sciences* 107 (50) (2010); Miller et al., "A TALE nuclease architecture for efficient genome editing" *Nature Biotechnology* 29 (2): 143-148 (2010); and Huang et al., "Heritable gene targeting in zebrafish using customized TALENs". *Nature Biotechnology* 29 (8):699 (2011). The crystal structure of a TAL effector bound to DNA indicates that each repeat comprises two alpha helices and a short RVD-containing loop where the second residue of the RVD makes sequence-specific DNA contacts while the first residue of the RVD stabilizes the RVD-containing loop. Target sites of TAL effectors also tend to include a T flanking the 5' base targeted by the first repeat and this appears to be due to a contact between this T and a conserved tryptophan in the region N-terminal of the central repeat domain. Mak et al., "The Crystal Structure of TAL Effector PthXol Bound to Its DNA Target" *Science* (2012); and Deng et al., "Structural Basis for Sequence-Specific Recognition of DNA by TAL Effectors" *Science* (2012). This simple code between amino acids in TAL effectors and DNA bases in their target sites has been utilized to generate the TALEs targeted to specific telomeric and centromeric double stranded DNA sequences as disclosed herein. Artificial TAL effectors capable of recognizing new DNA sequences have been designed in a variety of other experimental systems. Christian et al., "TAL Effector Nucleases Create Targeted DNA Double-strand Breaks" Genetics 186 (2): 757-61 (2010); Zhang et al., "Efficient construction of sequence-specific TAL effectors for modulating mammalian transcription" *Nature Biotechnology* 29 (2):149 (2011); and Mahfouz et al., "De novo-engineered transcription activator-like effector (TALE) hybrid nuclease with novel DNA binding specificity creates double-strand breaks" *Proceedings of the National Academy of Sciences* 108: 2623 (2011).

Compositions and kits relating to customized peptides, i.e. d(designer)TAL effector (dTALE) peptides comprising customized polypeptide sequences that act as sequence-specific nucleic acid binding proteins have been reported. Zhang, et al., "Transcription activator-like effectors." US 2012/0270273 (herein incorporated by reference). However, Zhang et al. does not disclose any TALE fusion proteins having the proper amino acid sequence for binding to telomere and/or centromere repeat sequences. Further, Zhang et al. does not disclose any data of TALE-fluorescent peptides bound to genomic DNA. Zhang et al. has also disclosed dTALE-GFP nucleic acid binding peptides having the mCherry, i.e. red, fluorescent label. Zhang, et al., "Efficient construction of sequence-specific TAL effectors for modulating mammalian transcription." *Nature Biotechnology* 29(2):149-153 (2011)—PubMed versions. However, again, there is no data showing that these peptides have any ability to label cells. dTALE-GFP fluorescent cells in this publication. This publication is silent on telomere and centromere, in addition to not showing actual fluorescent images of TALE-fluorescent peptides bound to genomic DNA.

TALE-fusion peptides constructed as engineered proteins having at least one TALE repeat unit as DNA-specific binding domains have been reported. Gregory et al., "Novel DNA-Binding Proteins And Uses Thereof" WO/2011/146121 Specifically, Gregory et al. describes a TALE-fusion peptide consisting of a reporter or selection marker, such as a fluorescent marker or enzyme, wherein the TALE-repeat domain was engineered to recognize a specifically desired target sequence. Gregory et al., however, does not describe a TALE-fluorescent peptide comprising telomere or centromere target sequence binding domains using live cell imaging nor a cell labeled with a TALE-fusion protein.

Fusion polypeptides, including a fusion between a ZFP (zinc-finger protein) DNA-binding domain and a transcriptional activation domain have been reported. Wolffe, et al., "Databases Of Regulatory Sequences; Methods Of Making And Using Same." WO/2001/083732. Wolffe et al. also describes methods to identify accessible DNA binding sites as potential regulatory sequences in many types of chromatin including centromeres and telomeres. Nonetheless, Wolffe et al. does not disclose using a TALE-fluorescent peptide comprising telomere or centromere binding domains.

Transcription activator-like effector proteins (TALEs) from the plant pathogenic bacterial genus *Xanthomonas* have been reported where a DNA-binding domain can be adjusted to bind any desired target sequence with high specificity. Bultmann et al., "Targeted transcriptional activation of silent oct4 pluripotency gene by combining designer TALEs and inhibition of epigenetic modifiers" *Nucleic Acids Research,* 40(12):5368-5377 (2012). Here, TALEs were designed, i.e. dTALEs, targeting a distinct 19-bp sequence of the murine pluripotency gene oct4 having mCherry fused to the N-terminus in order to monitor transfection efficiency and expression levels of the constitutively expressed dTALE vector after transfection into murine and human cells. However, specific dTALE binding to genomic sequences was not shown because these cells were co-transfected with a poct4-GFP reporter construct also containing target nucleic acid sequences. Thus, Bultmann et al. is silent on detecting telomere and centromere nucleic acid sequences, in addition to not showing specific fluorescent images of cells demonstrating TALE-fluorescent peptides bound to genomic DNA.

Two types of TALE chimeric proteins were disclosed as first and second monomers having binding regions for repetitive DNA sequences along with capability for catalytic activity. Duchateau et al., "New TALE-Protein Scaffolds And Uses Thereof" WO/2012/138939. When these two types of monomers form dimers around DNA sequences they became catalytically active as do TALENs when a nuclease catalytic domain such Fok1 is fused to at least one TALE C-terminal region. Duchateau et al. further describes TALEs as having several protein subdomains where at least one protein domain is a reporter protein such as a fluorescent protein, luciferase, or β-galactosidase. However, Duchateau et al. is silent on telomere and centromere, in addition to not showing actual fluorescent images of TALE-fluorescent peptides bound to genomic DNA.

Peptide nucleic acid (PNA), a hybrid peptide-DNA construct where the DNA backbone is replaced by amino acids and peptide bonds, has been reported to specifically target telomeric DNA repeat sequences. Molenaar et al., "Visualizing telomere dynamics in living mammalian cells using PNA probes." *EMBO J.* 22(24): 6631-6641 (2003). Molenaar et al. used a fluorescent cy3 (C3TA2)3-labeled PNA probe that was introduced in living human U2OS and mouse MS5 cells by glass bead loading and was shown to specifically associate with telomeric DNA in vivo by digital fluorescence microscopy. Molenaar et al. does not describe a TALE or TAL effector peptide linked to a fluorescent protein.

Stable expression of fluorescent versions of telomeric proteins (Tagged Telomeric Proteins) has been observed in human primary fibroblasts (IMR90) and HeLa cells with long telomeres (HeLa1.2.11) for positioning of human telomeres in living cells. Crabbe, et al., "Human Telomeres Are Tethered to the Nuclear Envelope during Postmitotic Nuclear Assembly" *Cell Rep.* 2(6):1521-9 9 (2012). Combined expression of EGFP-TRF1 and the histone H2B-mCherry allowed the concomitant visualization of telomeres and chromatin in living cells and fixed cells. HeLa1.2.11 cells. Crabbe et al. does not describe a TALE or TAL effector peptide linked to a fluorescent protein.

A four-dimensional telomere analysis using recordings of living human cells acquired with controlled light exposure microscopy has been reported. De Vos, et al., "Four-Dimensional Telomere Analysis In Recordings Of Living Human Cells Acquired With Controlled Light Exposure Microscopy" *J Microsc.* 238(3):254-64 (2010). The quantitative telomere analysis was done in cell nuclei of living human cells expressing telomere-binding fusion proteins. De Vos et al. does not describe a TALE or TAL effector peptide linked to a fluorescent protein in the performance of this analysis.

Plant and mouse cells expressing PZF (zinc finger):GFP proteins have been analyzed by confocal microscopy. Lindhout et al., "Live cell imaging of repetitive DNA sequences via GFP-tagged polydactyl zinc finger proteins" *Nucleic Acids Res.* 35(16):e107 (2007). For *Arabidopsis*, a PZF:GFP protein aimed to specifically recognize a 9-bp sequence within centromeric 180-bp repeat was used to monitor centromeres in living roots. In mouse cells a PZF:GFP protein was targeted to a 9-bp sequence in the major satellite repeat. Both PZF:GFP proteins localized in chromocenters which represent heterochromatin domains containing centromere and other tandem repeats. Lindhout et al. does not describe a TALE or TAL effector peptide linked to a fluorescent protein.

Transcription activator-like effectors (TALEs) have been reported to recognize specific DNA sequences based on sequence composition of repeating oligopeptide elements. Boch, J. et al., "Breaking the code of DNA binding specificity of TAL-type III effectors: *Science* 326, 1509-1512 (2009). Advances in DNA cloning technologies have enabled facile assembly of TALEs for sequence-specific DNA recognitions well as fusion of paired nucleases (TALENs) for genome engineering. Baker, M., "Gene-editing nucleases" *Nature Methods* 9, 23-26 (2012). Although TALEs and TALENs have rapidly become useful tools for genome editing and transcription regulation, their intranuclear dynamics of DNA recognition is not well understood since they are typically directed to a single-copy sequence, thus limiting cytological studies and applications. Bogdanove et al., "TAL effectors: customizable proteins for DNA targeting" *Science* 333, 1843-6 (2011).

III. TALE-Targeting of Double Stranded Nucleic Acid Sequences

In one embodiment, the present invention contemplates a method is based on Transcriptional Activator-Like Effector (TALE):DNA recognition and targeting to repeated DNA sequences in human genome which is independent of nucleic acid hybridization. In one embodiment, these custom designed peptides are coupled to FPs and expressed from plasmids in bacteria or mammalian cells. In one embodiment, the method further comprises detecting a tandemly repeated double stranded DNA sequence array in a single step. This provides a unique advantage over other conventional methods because the method can provide useful results within an hour. A further advantage is that the expression of probes in bacteria greatly reduces the cost of this analysis. In one embodiment, the equilibrium dissociation constant of the TALE:DNA binding is in the low nanomolar range. Although it is not necessary to understand the mechanism of an invention, it is believed that the affinity of TALE:DNA is equal to or higher than most of antibody-mitogen interactions.

In one embodiment, the present invention contemplates methods for developing chromosome enumeration probes or locus specific probes for clinical diagnosis of genetic diseases, such as chromosome breaks, translocations or unusual locations relative to other chromosomes or non-chromosomal nuclear bodies. In one embodiment, the present invention contemplates a method for assessing telomere length distribution by flow cytometry.

Transcription Activator-Like Effectors (TALEs) are generally believed to be oligopeptide arrays that recognize specific DNA sequences. In typical conventional applications, TALEs can be fused to a nuclease in order to mediate site-directed DNA cleavage for genome engineering. In some embodiments, the present invention contemplate protein TALE DNA probes capable of binding to teleometric and centrometric double stranded DNA target sequences that lack a nuclease. In one embodiment, the protein TALE DNA probe further comprises a fluorescent protein (FP). Expression of TALE proteins from plasmids in human U2OS cells were observed to result in bright signals coincident with telomeres and centromeres, allowing the dynamics of these chromosomal regions to be tracked during interphase and mitosis. Expression of these TALEs (without FPs) by in vitro coupled transcription/translation system, and used them as probes to detect telomeric and centromeric sequences in fixed cells. This is a very rapid procedure that obviates DNA denaturation and other requisite steps in conventional in situ nucleic acid hybridization, since the TALEs recognize specific DNA sequences in the double helix. Further expression of TALEs in *E. Coli* will make it a very low cost.

Previous studies have reported relative intranuclear positions of telomeres and nucleoli in living cells by labeling and tracking ribosomal RNA out of nucleoli in living cells. Politz et al., "Diffusion-based transport of nascent ribosomes in the nucleus" *Mol. Biol. Cell* 14, 4805-4812 (2003). Ribosomal RNA genes may lie close to telomeres in the short arms of several human chromosomes thereby providing a possible mechanism to directly detect and/or label telomeres in live cells. Henderson et al., "Location of ribosomal DNA in the human ribosomal DNA complement" *Proc. Natl. Acad. Sci.* 69, 3394-3398 (1972). Although it is not necessary to understand the mechanism of an invention it is believed that since TALEs recognize specific sequences in double-stranded DNA form, live cell applications would be feasible and that a telomere-specific TALE fused to a fluorescent protein might be a way to label the ends of chromosomes in live cells.

Peptide Nucleic Acid (PNA) probes were used to detect several target telomere and centromere repeat sequences common to human satellites II and III, a centromere repeat sequence specific for the centromeric region of the X chromosome, and for detecting and optionally quantitating the length of multiple copies of a centromere repeat sequence for specific chromosome 18. Lansdorp, et al., "Method For Detecting Multiple Copies Of A Repeat Sequence In A Nucleic Acid Molecule." U.S. Pat. No. 6,514,693 (herein incorporated by reference). These probes were used for detecting and/or determining the length of multiple copies of a telomeric repeat in a nucleic acid molecule in addition to other measurements. Lansdorp et al. does not disclose a TALE or TAL effector peptide linked to a fluorescent protein, does not describe labeling both live and fixed human cells and does not describe flow cytometry sorting or analysis of whole cells. Further, Lansdorp et al. is silent on a probe having a labeled amino acid.

A flow cytometry method has been reported using human, mouse and Chinese hamster cells, i.e. chromosome flow fluorescence in situ hybridization (FISH), called CFF, to analyze repetitive DNA in chromosomes with directly labeled peptide nucleic acid (PNA) probes. Brind'Amour et al. "Analysis Of Repetitive DNA In Chromosomes By Flow Cytometry." Nat Methods, 8: 484-6 (2011). Telomeric sequences of repetitive DNA were detected. The disclosed hybridization probes require denaturation of the target nucleic acid molecules simultaneously by heat or pH treatment. Brind'Amour et al. does not describe a TALE or TAL effector peptide linked to a fluorescent protein, does not describe labeling both live and fixed human cells and does not describe flow cytometry sorting or analysis of whole cells. Further, Brind'Amour et al. is silent on a probe having a labeled amino acid.

Polyamides have been described that recognize pentameric nucleic acid sequences, which are tandemly repeated within the heterochromatic regions of several chromosomes. Gygi, et al., "Use of fluorescent sequence-specific polyamides to discriminate human chromosomes by microscopy and flow cytometry." *Nucleic Acids Res.* 30:2790 (2002). These probes are sequence-specific, minor groove-binding polyamides such that intact (undenatured) DNA is labeled. The molecule folds into a 'hairpin' structure, such that two polyamide oligomers bind in a side-by-side, anti-parallel manner in the minor groove. The polyamide probe results in an intense signal on the targeted regions of chromosome 9, Y, 1, 16 and the acrocentric chromosomes. Gygi, et al., does not describe a TALE or TAL effector peptide linked to a fluorescent protein, does not describe labeling both live and fixed human cells and does not describe flow cytometry sorting or analysis of whole cells. Further, Gygi, et al., is silent on a probe having a labeled amino acid.

Polyamides comprising N-methylpyrrole (Py)-N-methylimidazole (Im) polyamide conjugates have been reported which have been developed from the DNA-binding antibiotics distamycin A and netropsin. Vaijayanth, et al., "Progress and Prospects of Pyrrole-Imidazole Polyamide-Fluorophore Conjugates as Sequence-Selective DNA Probes." *Chem Bio Chem.* 13:(15):2170-2185 (2012). These synthetic small molecules bind with duplex DNA in a sequence-specific manner. Vaijayanth, et al. describes an overview of the current and prospective applications of Py-Im polyamide-fluorophore conjugates, including sequence-specific recognition with fluorescence emission properties, and their potential roles in biological imaging. Vaijayanth et al. does not describe a TALE or TAL effector peptide linked to a fluorescent protein, does not describe labeling both live and fixed human cells and does not describe flow cytometry sorting or analysis of whole cells. Further, Vaijayanth et al. is silent on a probe having a labeled amino acid.

Labeling of telomeric repeats in Syrian hamster primary fibroblast cultures were analyzed using FISH or transfected with a plasmid expressing a telomeric binding protein (TRF1 fused with GFP). Solovjeva, et al., "Characterization of telomeric repeats in metaphase chromosomes and interphase nuclei of Syrian Hamster Fibroblasts." *Molecular Cytogenetics,* 5:37 (2012); and Krutilina, et al., "A negative regulator of telomere-length protein trf1 is associated with interstitial (TTAGGG)n blocks in immortal Chinese hamster ovary cells." *Biochem Biophys Res Commun.* 280(2):471-5 (2001). Relative lengths of telomere signals were estimated. Low-intensity FISH signals were visualized with different frequency of detection on all other metacentric chromosomes excluding chromosome #21., i.e. chromosome 15, 18. These reports did not use any specific probe for centromere DNA, but found interstitial telomeric sequences in pericentromeric heterochromatin regions of the majority of metacentric chromosomes. Solovjeva et al does not describe a TALE or TAL effector peptide linked to a fluorescent protein, does not describe labeling both live and fixed human cells and does not describe flow cytometry sorting or analysis of whole cells. Further, these reports are silent on a probe having a labeled amino acid.

Associations between TALE proteins and nucleic acid target sequences has been discussed. Bonas et al., "Modular DNA-Binding Domains And Methods Of Use" WO 2010/079430; Gregory et al., "Novel DNA-Binding Proteins And Uses Thereof" WO 2011/146121; and Kuhn et al., "Fusion Proteins Comprising A DNA-Binding Domain Of A TAL Effector Protein And A Non-Specific Cleavage Domain Of A Restriction Nuclease And Their Use" WO 2011/154393-A1.

In one embodiment, the present invention contemplates compositions comprising TALEs designed to recognize either DNA strand of the telomeric repeat. See, FIG. 1A. In one embodiment, the TALE comprises a polypeptide constructed from DNA plasmids with in-frame fusions to the desired fluorescent protein, followed by transfection and expression in human U2OS cells. For example, when TALEs TelL20 or TelR20 were co-expressed for 24 hours numerous discrete fluorescent foci were observed colocalization in interphase cells. See, FIG. 1B. In one embodiment, the plasmid comprises a nucleic acid sequence encoding a TelR15 protein of (SEQ ID NO: 20)

ATGGCCACCACCCATATGGGATCCGGTATCCACGGAGTCCCAGCAGCCGT

AGATTTGAGAACTTTGGGATATTCACAGCAGCAGCAGGAAAAGATCAAGC

CCAAAGTGAGGTCGACAGTCGCGCAGCATCACGAAGCGCTGGTGGGTCAT

GGGTTTACACATGCCCACATCGTAGCCTTGTCGCAGCACCCTGCAGCCCT

TGGCACGGTCGCCGTCAAGTACCAGGACATGATTGCGGCGTTGCCGGAAG

CCACACATGAGGCGATCGTCGGTGTGGGGAAACAGTGGAGCGGAGCCCGA

GCGCTTGAGGCCCTGTTGACGGTCGCGGGAGAGCTGAGAGGGCCTCCCCT

TCAGCTGGACACGGGCCAGTTGCTGAAGATCGCGAAGCGGGGAGGAGTCA

CGGCGGTCGAGGCGGTGCACGCGTGGCGCAATGCGCTCACGGGAGCACCC

CTCAACCTGACCCCAGAGCAGGTCGTGGCAATTGCGAGCAACATCGGGGG

AAAGCAGGCACTCGAAACCGTCCAGAGGTTGCTGCCTGTGCTGTGCCAAG

CGCACGGACTTACGCCAGAGCAGGTCGTGGCAATTGCGAGCAACATCGGG

GGAAAGCAGGCACTCGAAACCGTCCAGAGGTTGCTGCCTGTGCTGTGCCA

AGCGCACGGACTAACCCCAGAGCAGGTCGTGGCAATTGCGAGCCATGACG

GGGGAAAGCAGGCACTCGAAACCGTCCAGAGGTTGCTGCCTGTGCTGTGC

CAAGCGCACGGGTTGACCCCAGAGCAGGTCGTGGCAATTGCGAGCCATGA

CGGGGGAAAGCAGGCACTCGAAACCGTCCAGAGGTTGCTGCCTGTGCTGT

GCCAAGCGCACGGCCTGACCCCAGAGCAGGTCGTGGCAATTGCGAGCCAT

GACGGGGGAAAGCAGGCACTCGAAACCGTCCAGAGGTTGCTGCCTGTGCT

GTGCCAAGCGCACGGACTGACACCAGAGCAGGTCGTGGCAATTGCGAGCA

ACGGAGGGGGAAAGCAGGCACTCGAAACCGTCCAGAGGTTGCTGCCTGTG

CTGTGCCAAGCGCACGGACTTACACCCGAACAAGTCGTGGCAATTGCGAG

CAACATCGGGGGAAAGCAGGCACTCGAAACCGTCCAGAGGTTGCTGCCTG

TGCTGTGCCAAGCGCACGGACTTACGCCAGAGCAGGTCGTGGCAATTGCG

AGCAACATCGGGGGAAAGCAGGCACTCGAAACCGTCCAGAGGTTGCTGCC

-continued

TGTGCTGTGCCAAGCGCACGGACTAACCCCAGAGCAGGTCGTGGCAATTG

CGAGCCATGACGGGGGAAAGCAGGCACTCGAAACCGTCCAGAGGTTGCTG

CCTGTGCTGTGCCAAGCGCACGGGTTGACCCCAGAGCAGGTCGTGGCAAT

TGCGAGCCATGACGGGGGAAAGCAGGCACTCGAAACCGTCCAGAGGTTGC

TGCCTGTGCTGTGCCAAGCGCACGGCCTGACCCCAGAGCAGGTCGTGGCA

ATTGCGAGCCATGACGGGGGAAAGCAGGCACTCGAAACCGTCCAGAGGTT

GCTGCCTGTGCTGTGCCAAGCGCACGGACTGACACCAGAGCAGGTCGTGG

CAATTGCGAGCAACGGAGGGGGAAAGCAGGCACTCGAAACCGTCCAGAGG

TTGCTGCCTGTGCTGTGCCAAGCGCACGGCCTCACCCCAGAGCAGGTCGT

GGCAATTGCGAGCAACATCGGGGGAAAGCAGGCACTCGAAACCGTCCAGA

GGTTGCTGCCTGTGCTGTGCCAAGCGCACGGACTCACGCCTGAGCAGGTA

GTGGCTATTGCATCCaacatcGGGGGCAGACCCGCACTGGAGTCAATCGT

GGCCCAGCTTTCGAGGCCGGACCCCGCGCTGGCCGCACTCACTAATGATC

ATCTTGTAGCGCTGGCCTGCCTCGGCGGACGACCCGCCTTGGATGCGGTG

AAGAAGGGGCTCCCGCACGCGCCTGCATTGATTAAGCGGACCAACAGAAG

GATTCCCGAGAGGACATCACATCGAGTGGCAGGCCTGCAGGGAAGTGGAA

TGCGTAAAGGCGAAGAGCTGTTCACTGGTGTCGTCCCTATTCTGGTGGAA

CTGGATGGTGATGTCAACGGTCATAAGTTTTCCGTGCGTGGCGAGGGTGA

AGGTGACGCAACTAATGGTAAACTGACGCTGAAGTTCATCTGTACTACTG

GTAAACTGCCGGTACCTTGGCCGACTCTGGTAACGACGCTGACTTATGGT

GTTCAGTGCTTTGCTCGTTATCCGGACCATATGAAGCAGCATGACTTCTT

CAAGTCCGCCATGCCGGAAGGCTATGTGCAGGAACGCACGATTTCCTTTA

AGGATGACGGCACGTACAAAACGCGTGCGGAAGTGAAATTTGAAGGCGAT

ACCCTGGTAAACCGCATTGAGCTGAAAGGCATTGACTTTAAAGAAGACGG

CAATATCCTGGGCCATAAGCTGGAATACAATTTTAACAGCCACAATGTTT

ACATCACCGCCGATAAACAAAAAAATGGCATTAAAGCGAATTTTAAAATT

CGCCACAACGTGGAGGATGGCAGCGTGCAGCTGGCTGATCACTACCAGCA

AAACACTCCAATCGGTGATGGTCCTGTTCTGCTGCCAGACAATCACTATC

TGAGCACGCAAAGCGTTCTGTCTAAAGATCCGAACGAGAAACGCGATCAT

ATGGTTCTGCTGGAGTTCGTAACCGCAGCGGGCATCACGCATGGTATGGA

TGAACTGTACAAATAG.

Although it is not necessary to understand the mechanism of an invention, it is believed that TALEs recognize specific DNA sequences in native double-stranded DNA by reading from the major grove. It is further believed that co-expression of TALE-FP's designed for either strand of the telomeric repeat resulted in similar patterns of discrete nuclear foci with the two colors displaying complete spatial coincidence indicates that both strands of the telomeric repeat are accessible. For example, U2OS cells are aneuploid, with ~65 chromosomes, so are expected to have ~130 telomeres in G1 cells and ~260 in G2 cells. Janssen et al., "Genetic instability: tipping the balance" *Oncogene* 32, 4459-70 (2013). The data disclosed herein shows that the number of foci (e.g., telomeres) observed was <50, which could mean that not all telomeres were labeled or that many labeled sites are out of the focal plane.

Figure 7:
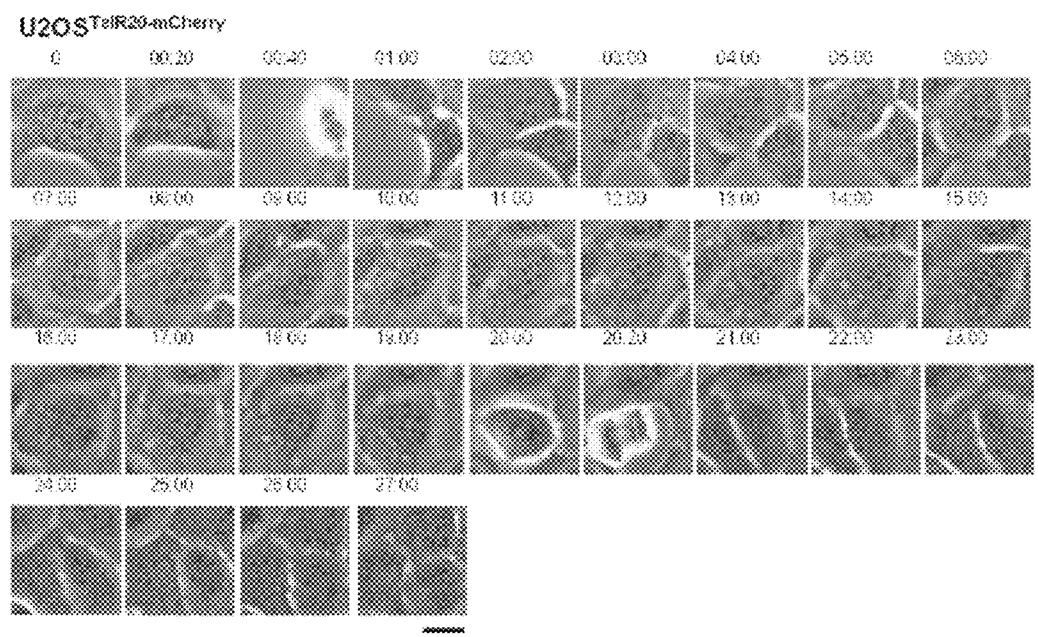
FIG. 7 presents exemplary data of single cell tracking of telomeres during cell cycle progression. The progression of selected U2OSTelR20-mCherry cells was tracked over 27 hours. Scale bar, 20 μm.

Time-lapse imaging was performed in a stable cell line expressing the TelR20-mCherry that tracked dynamic movements of the foci during cell cycle progression. See, FIG. 7. The observed kinetics and spatial parameters were very similar to those previously reported in studies in which telomeres were labeled by other methods in U2OS cells or a human bladder carcinoma cell line. Molenaar et al., "Visualizing telomere dynamics in living mammalian cells using PNA probes" *EMBO J.* 22, 6631-6641 (2003); Jegou et al., "Dynamics of telomere and promyelocytic leukemia nuclear bodies in a telomerase-negative human cell line" *Mol. Biol. Cell* 20, 2070-2082 (2009); and Wang et al., "Rapid telomere motions in live human cells analyzed by highly time-resolved microscopy" *Epigenet. & Chromatin* 1, 4 (2008).

Figure 8:
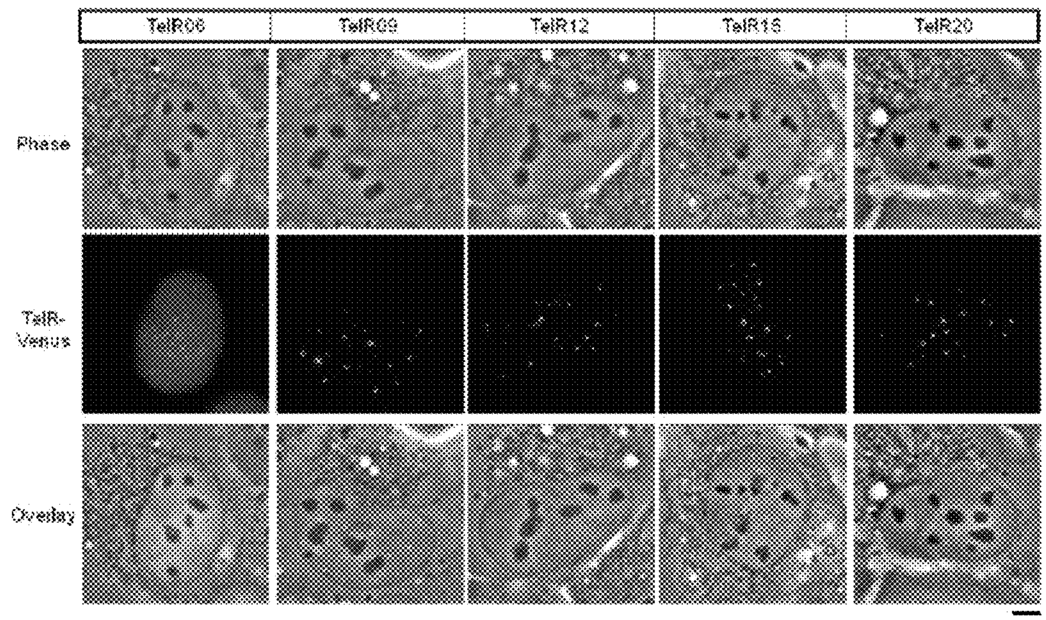
FIG. 8 presents exemplary data of live and fixed cell telomere labeling with fluorescent TALEs of different lengths.
Figure 9:
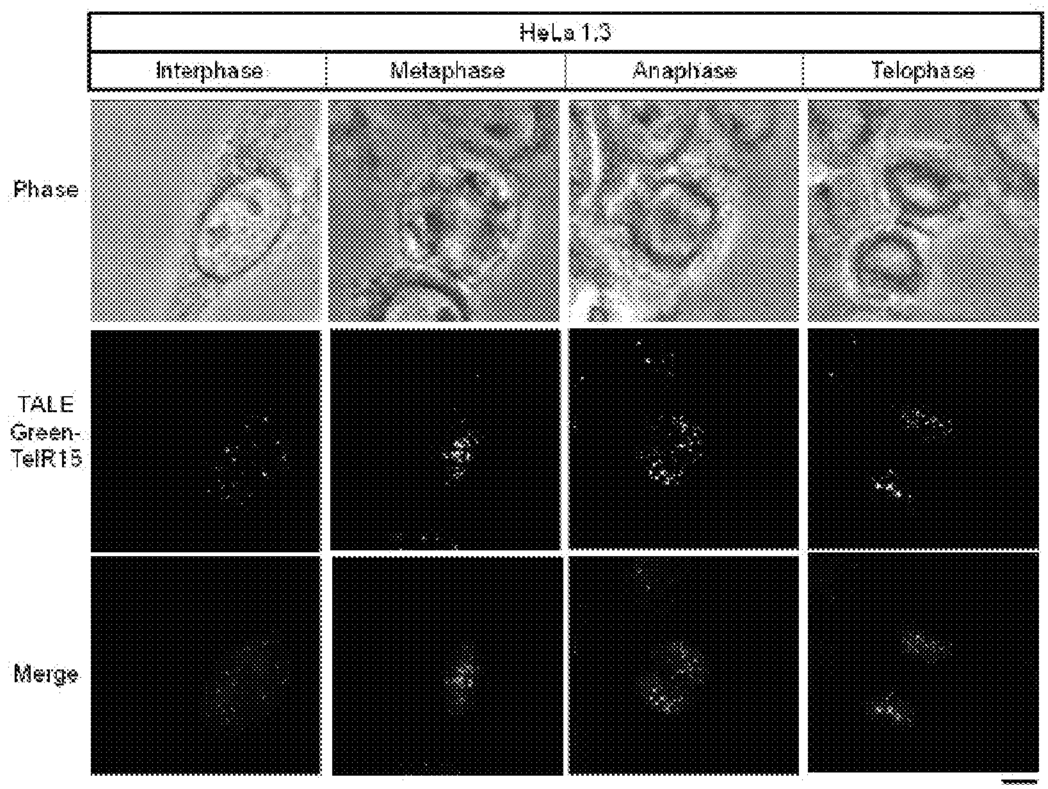
FIG. 9 presents exemplary data of telomeres in different cell cycle stages of HeLa cells. HeLa 1.3 cells were fixed and incubated with the probe TALEGreen-TelR15. Images merged with DAPI are shown in the bottom row. Scale bar, 5 μm.

To examine the specificity of TALEs binding to telomeres, TALEs of various lengths were designed (i.e., for example, TelR06, TelR09, TelR12, TelR15, TelR20). All of these TALEColor probes showed similar patterns in interphase nuclei except TelR06. See, FIG. 8. TALE-TelR06 showed some specific foci but also a high background throughout the nucleus suggesting that TALEs comprising six (6) monomers, or less, may partially lose telomeric specificity.

These data suggested that TALE-FPs might be also used as probes to detect telomeres in fixed cells. One advantage of this approach is that, even in fixed cells, TALE-FPs may bind to double stranded DNA thereby eliminating the conventional requirement of DNA denaturation or possibly other preconditioning and/or annealing steps needed in FISH and thus might offer a shorter turnaround time.

Figure 2:
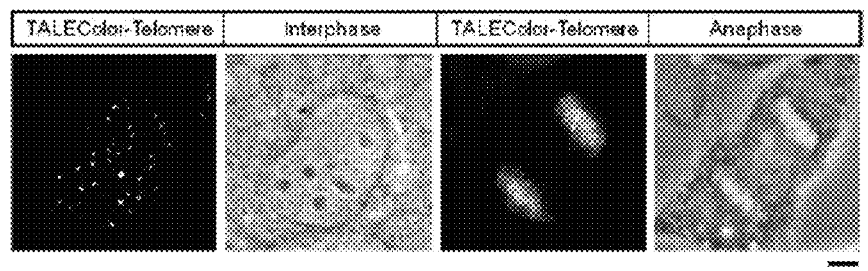
FIG. 2 presents exemplary data of TALE-FP labeled telomeres in fixed cells.
Figure 2:
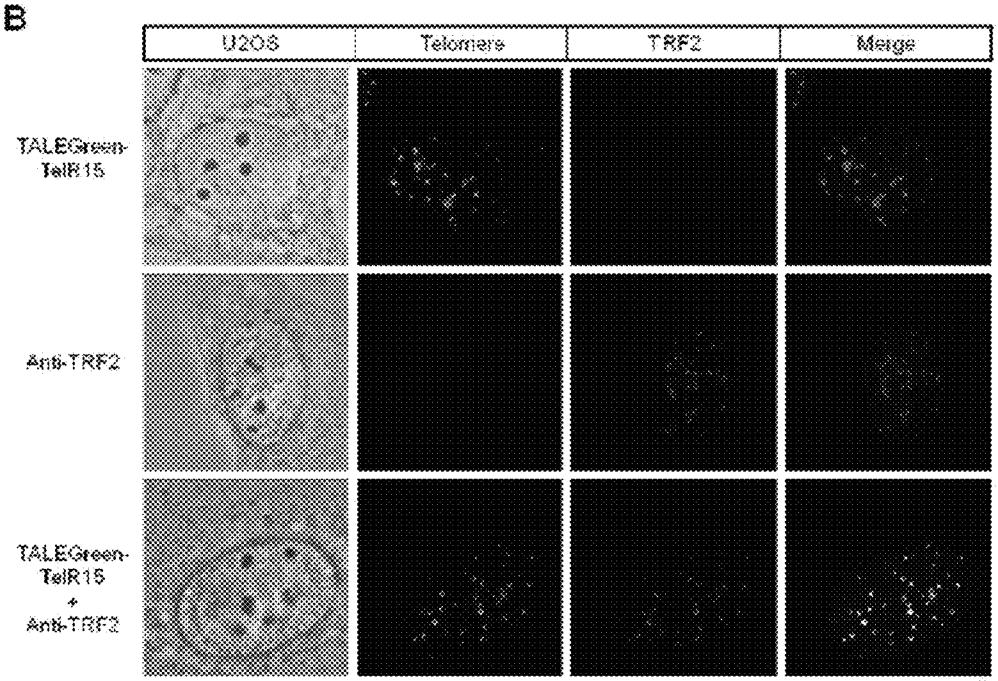
Figure 2:
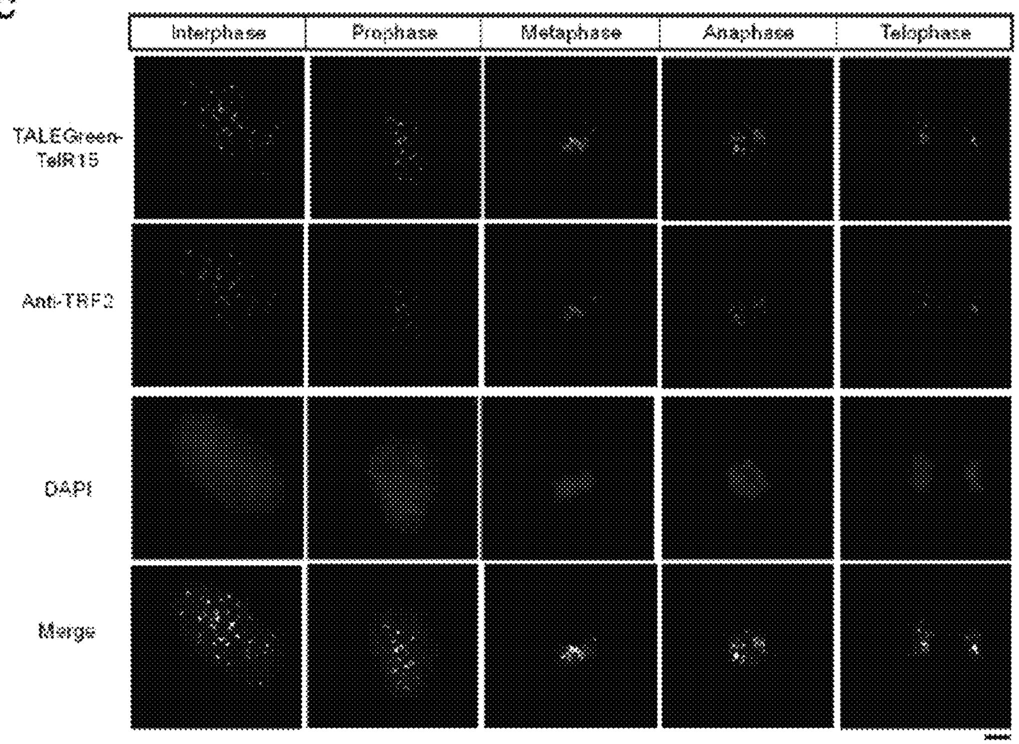

Plasmids were constructed for coupled in vitro transcription-translation of telomere-specific TALEs fused in-frame with various fluorescent proteins. A typical result of an experiment in which the TALEGreen-TelR15 was used in fixed human U2OS cells showed numerous discrete fluorescent foci were observed in interphase and also mitosis. See, FIG. 2A. To confirm that these signals represent binding of the TALE to telomeres, immunostaining was performed using the telomere-specific protein TRF2. Broccoli et al., "Human telomeres contain two distinct Myb-related proteins, TRF1 and TRF2" *Nat. Genet.* 17, 231-235 (1997). This experiment co-localized TALE signals in both interphase and mitotic cells. Compare, FIGS. 2B and 2C. Besides U2OS cells, discrete fluorescent foci were also observed in HeLa cells in interphase and also mitosis.

Figure 3:
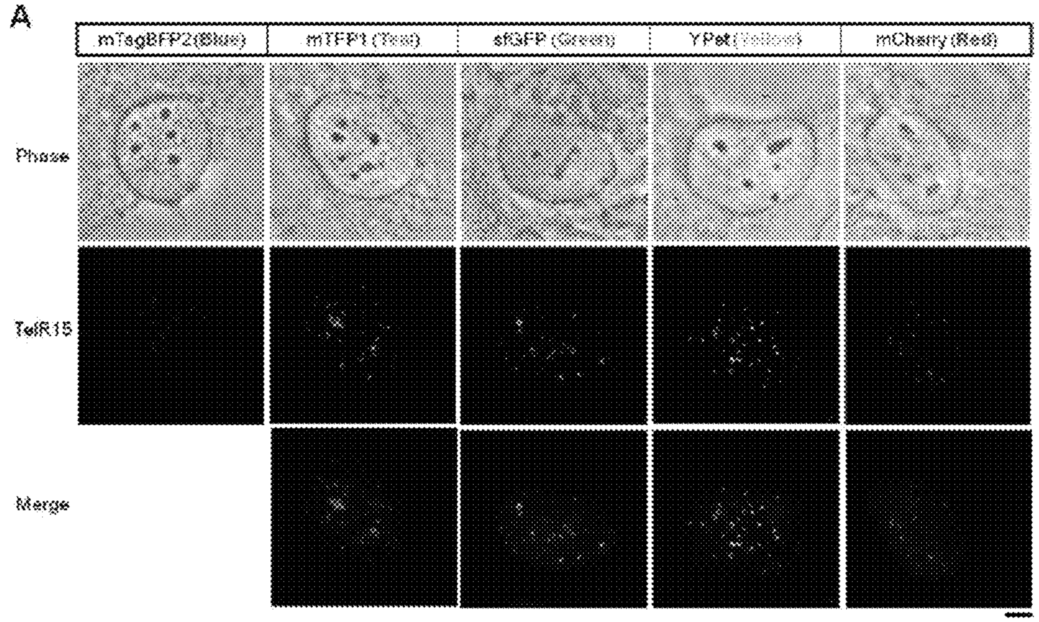
FIG. 3 shows exemplary data of spectral variants of TALEColor probes.
Figure 3:
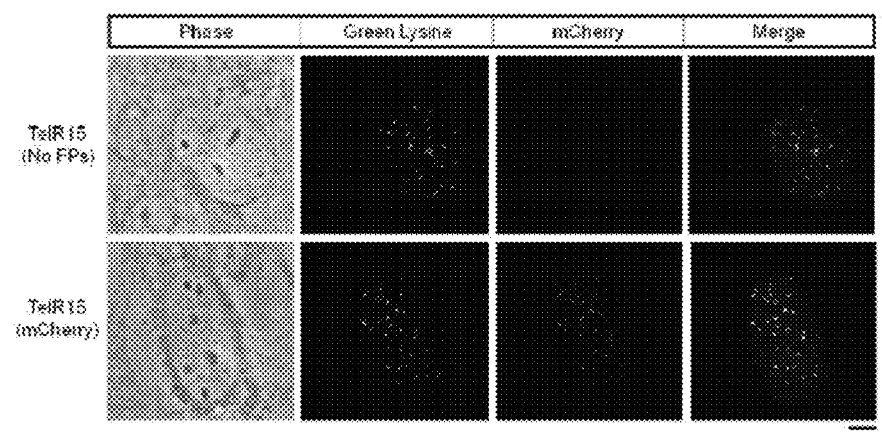

To determine how wide an array of fluorescent proteins (FPs) might be applicable to this method, a number of telomere-TALE-FP plasmids were constructed for coupled in vitro transcription-translation. Further, a plasmid where the telomere-specific TALE was fused to a fluorescent amino acid (Green Lysine), instead of a fluorescent protein. The entire spectrum of fluorescent proteins tested, as well as the Green Lysine-labeled TALE, resulted in comparable signals with the same spatial patterns as established in the live cell experiments. Compare, FIGS. 3A and 3B. These data indicate that TALE-FPs contemplated by the present invention interfere with a specific TALE's DNA sequence recognition nor is the fluorescence intensity problematically attenuated by intramolecular folding interactions back into the TALE. Moreover, since the Green Lysine-labeled TALE also gave the same pattern, and with strong signal intensity, demonstrates that chemical modification within the TALE polypeptide can be accommodated. Meanwhile TALE-FPs purified from *E. coli* also showed bright signals with the same patterns as with in vitro translated TALE-FPs suggesting that TALEColor probes for the fixed cell version of the method can be generated in various ways (data not shown).

Although live cell labeling of telomeres with TALEs offer unique opportunities in basic cell biology and chromosome research, embodiments of the present invention are equally useful in fixed cell preparations. In particular, certain embodiments of a TALE-based, fixed cell telomere detection method could be applied to human cell lines with differing telomere lengths. In one embodiment, the method assesses interphase patterns of telomeres. In other embodiments, TALE-based fixed cell telomere detection methods correlate focal fluorescent signal intensity with telomere length.

Figure 4:
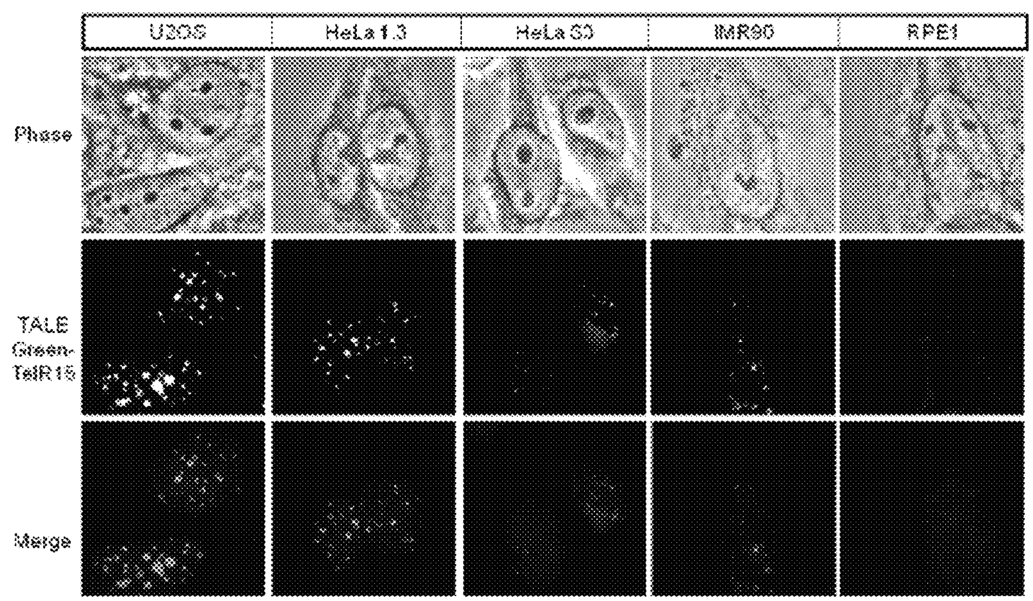
FIG. 4 presents exemplary data of telomeres compared by TALEColor in variety of human cell lines. U2OS, HeLa 1.3, HeLa S3, IMR90 and RPE1 cells were fixed and incubated with TALEGreen-TelR15 (middle row). All the images of TALEGreen-TelR15 (middle row) are scaled to the same. Images merged with DAPI are shown in the bottom row. Scale bar, 5 μm.

The data presented herein shows the results of applying a TALE-telomere probe to fixed human cells having different average telomere lengths. See, FIG. 4. For example, U2OS cells have a wide array of telomere lengths (i.e., for example, between approximately <3 kb to >50 kb) and the HeLa cell line 1.3 has average telomere length of approximately 23 kb. Takai et al., "In vivo stoichiometry of shelterin components" *J. Biol. Chem.* 285, 1457-67 (2010). In contrast, weaker signals were observed in three other human cell lines known to have shorter telomeres: HeLa S3 (telomere length 2-10 kb), IMR90 (Average length ~7.5 kb) and RPE1 (~2-12 kb), suggesting that under the constant probe conditions used in these fixed cell experiments the signals obtained correlate with average telomere length. Bryan et al., "Telomere length dynamics in telomerase-positive immortal human cell populations" *Exp. Cell Res.* 239, 370-8 (1998); Ouellette et al., "Telomerase activity does not always imply telomere maintenance" *Biochem. Biophys. Res. Commun.* 254, 795-803 (1999); and Bodnar et al., "Extension of life-span by introduction of telomerase into normal human cells" *Science* 279, 349-52 (1998).

Figure 5:
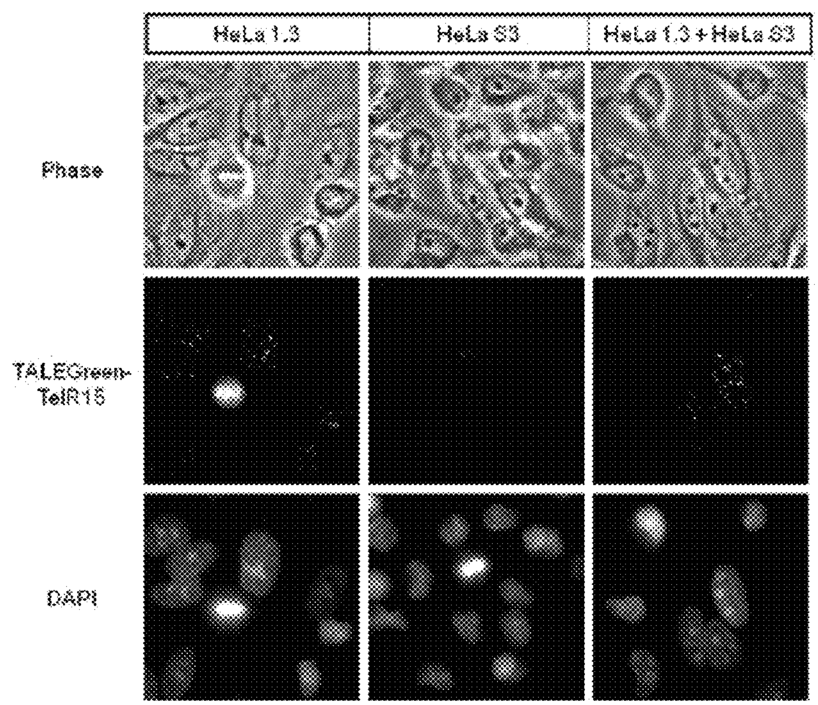
FIG. 5 presents exemplary data of imaging flow cytometry assessment of average telomere length and intra-cell population heterogeneity.
Figure 5:
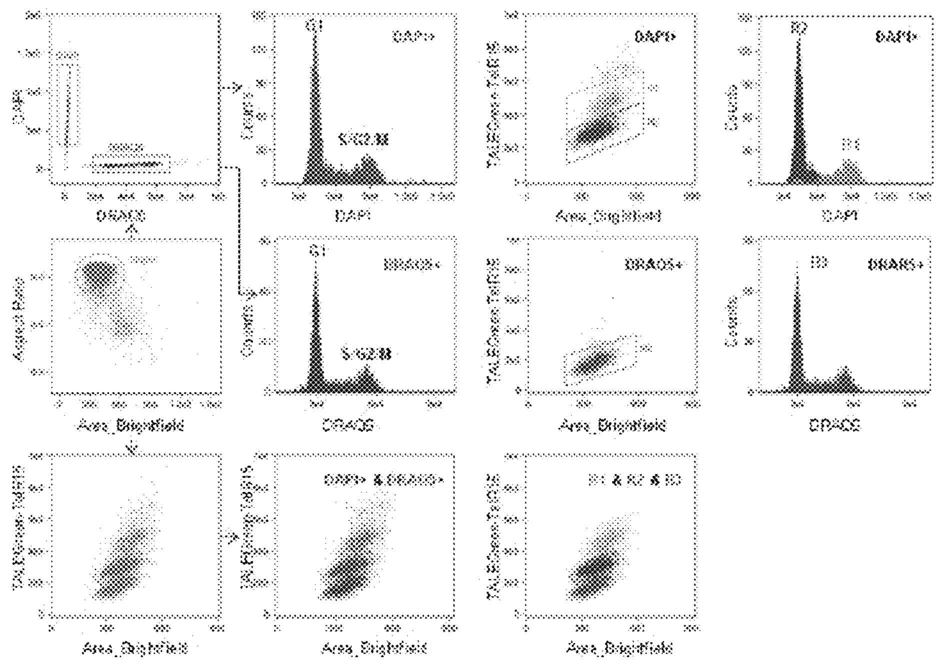
Figure 5:
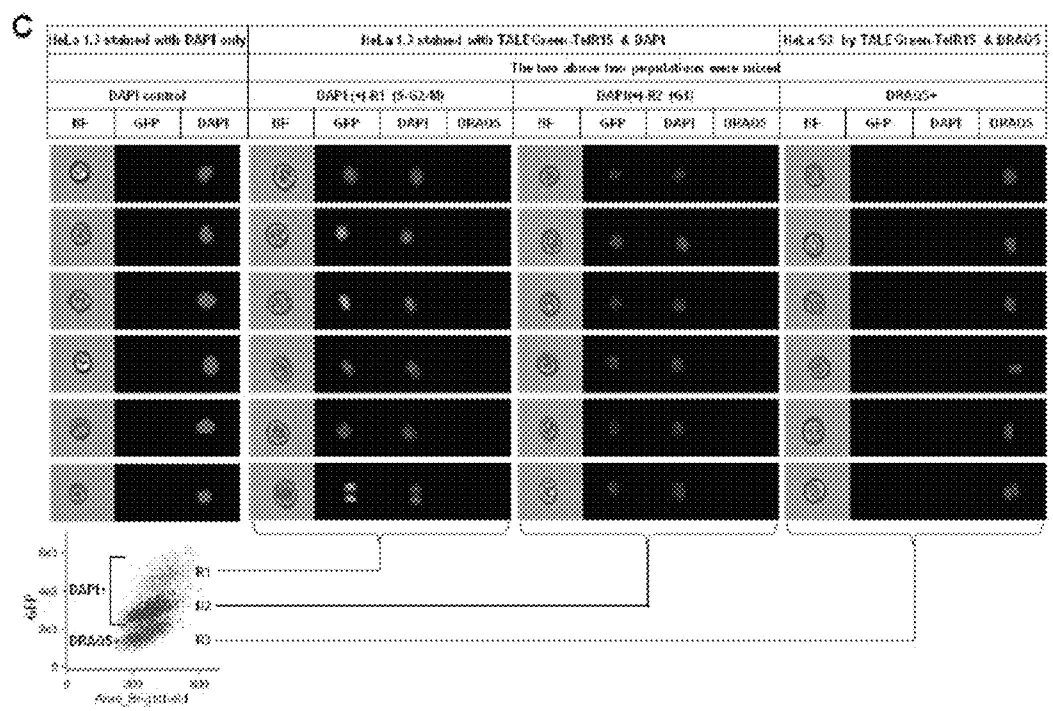

The relationship between the TALE probe signal intensity and the length of telomeres were further demonstrated by comparing the 1.3 HeLa cell line with the S3 HeLa cell line because these cell lines have different telomere lengths (e.g., average length ~23 kb and 2-10 kb, respectively). The two cell lines were co-cultured on coverglasses and subjected to TALE labeling. The telomere signals in HeLa 1.3 were much brighter as can be seen in separate or co-cultured cells. See, FIG. 5A. Imaging flow cytometry was then used to analyze telomere length by TALE labeling of suspension cultures of the two cell lines. DAPI and DRAQ5 were used to stain the DNA of HeLa 1.3 and S3 respectively, the cells were then mixed and TALE labeled with TALEGreen-TelR15, followed by FACS with the instrument's parallel single cell imaging capability. The two cell populations were clearly resolved on the basis of their two DNA labels. See, FIG. 5B, top left panel. Further, each population displayed a typical cell cycle distribution including G1, S, G2/M phases by DNA contents. See, FIG. 5B, middle left/top row and middle left/middle row. The TALEGreen-TelR15 signals were observed to separate into three populations. See, FIG. 5B, bottom left panel. As can be seen in the overlay plots, HeLa 1.3 was DAPI-positive with high and moderate telomere labeling, while HeLa S3 cells were DRAQ5-positive with low telomere labeling. See, FIG. 5B, middle left/bottom row. These data are compatible with the known telomere lengths of these two cell lines and consistent with the imaging from the coverglass cultures. See, FIG. 5A.

Various telomere labeling populations were then analyzed in each of these two cell lines with respect to the cell cycle. See, FIG. 5B. The DAPI-positive cells were gated as "R1" (high telomere labeling, shown in light green) and "R2" (moderate telomere labeling, shown as dark green). The DRAR5-positive population were gated as "R3" (low telomere labeling, shown as teal). The individual or overlay plots of R1, R2 and R3 are shown. See, FIG. 5B, middle right column. It can be seen that the high telomere labeling population was typified by a greater proportion of S/G2/M phase cells whereas the moderate telomere labeled population was enriched in G1 phase cells. See, FIG. 5B, top right panel.

Imaging flow cytometry was performed to generate images of each single cell represented in the above plots. The R1 population cells were DAPI-positive (purple, representing HeLa 1.3 cells) and displayed high TALEGreen-TelR15 signals (green) where the majority of this population included mitotic cells. See, FIG. 5C, middle left four columns. The R2 cell population were also DAPI-positive (and thus were HeLa 1.3) and had a moderate telomere labeling where the majority of this population included G1 cells. See, FIG. 5C, middle right four columns. The R3 cell population, defined as DRAQ5-positive (red, thus representing HeLa S3 cells) displayed low telomere labeling and included all cell cycle stages. See, FIG. 5C, right four columns.

In some embodiments, the presently contemplated TALE-based method was equally capable of detecting other tandemly repetitive DNA sequences. For example, when using satellite DNA sequences lying at or adjacent to centromeres. Human centromeric DNA are generally comprised of alpha satellite sequences, a tandem repeat family that are commonly studied in a chromosome-specific manner. Willard et al., "Hierarchical order in chromosome-specific human alpha satellite DNA" *Trends in Genetics* 3, 192-198 (1987). A plasmid was designed encoding a TALE that recognizes a motif specific to the alpha satellite consensus sequence providing a "Pan-Cen" probe that may be used concurrently with a telomere-specific TALE. Waye et al., "Nucleotide sequence heterogeneity of alpha satellite repetitive DNA: a survey of alphoid sequences from different human chromosomes" *Nucleic Acids Res.* 15, 7549-7569 (1987); and Vissel et al., "Human alpha satellite DNA-consensus sequence and conserved regions" *Nucleic Acids Res.* 15, 6751-6752 (1987).

Figure 6:
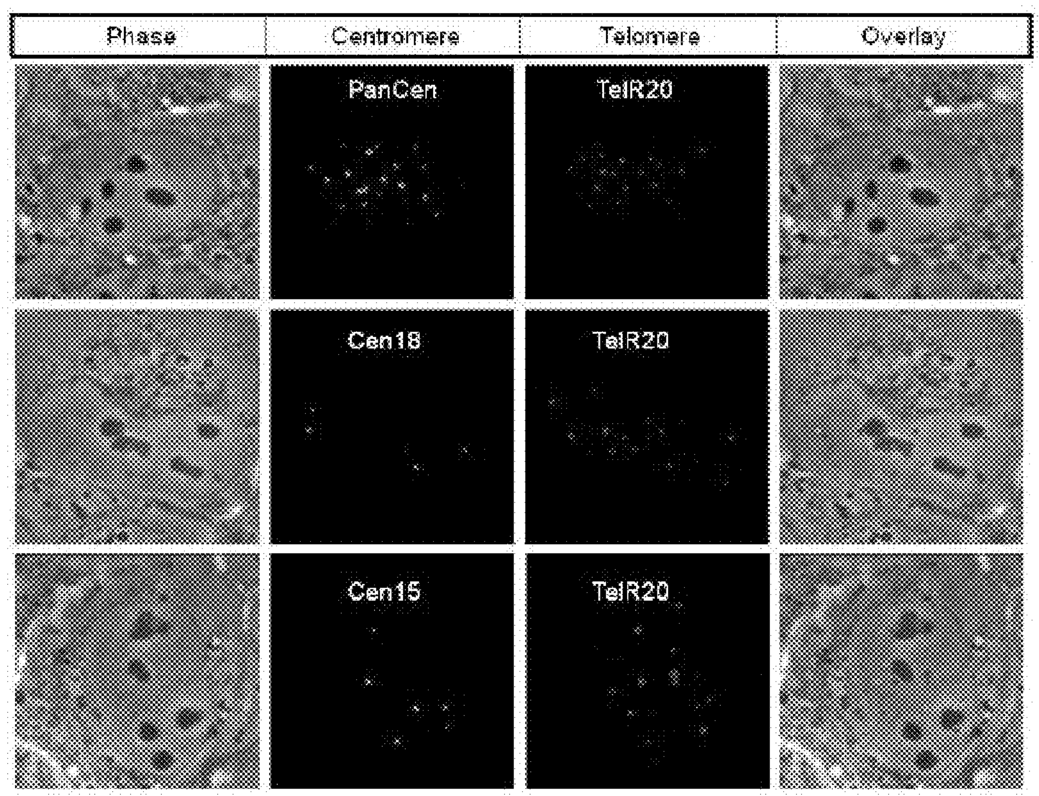
FIG. 6 presents exemplary data of live cell imaging of centromeres and telomeres by TALEColor. U2OS cells were co-transfected for 24 hours with TALEmCherry-TelR20 to label telomeres together with one of three TALEs designed to recognize centromeric repeats. Upper row: TALEVenus-PanCen, a TALE predicted to bind all human centromeres; middle row: TALEVenus-Cen18, specific for an α-satellite higher order repeat on chromosome 18 (D18Z1); bottom row: TALEVenus-Cen15, specific an α-satellite higher order repeat on chromosome 15 (D15Z3); Overlay images are shown in the right column. Scale bar, 5 μm.

These data demonstrated a pattern of discrete nuclear foci labeled with the Pan-Cen probe that was non-overlapping with a pattern of telomere foci. See, FIG. 6, upper row. This data is consistent with previous findings that telomeres and centromeres are neither coincident nor polarized (e.g, a Rabl-configuration) in most of higher eukaryotic cells. TALEs were then designed that were specific for higher order alpha satellite repeats that are unique to either chromosome 18 and 15 bp expression in U2OS cells. Alexandrov et al., "Chromosome-specific alpha satellites: two distinct families on human chromosome 18" *Genomics* 11, 15-23 (1991); and Choo et al., "Identification of two distinct subfamilies of alpha satellite DNA that are highly specific for human chromosome 15" *Genomics* 7, 143-151 (1990). Each of these TALEs labeled a set of discrete foci: five with the Cen18 and six with the Cen15 probes respectively, consistent with the karyotype of U2OS cells, viz. trisomy of chromosomes 18 and 15. See, FIG. 6, middle row and bottom row, respectively.

In one embodiment, the present invention contemplates a plasmid comprising a nucleic acid encoding a Cen15 probe having the sequence of:

```
                                       (SEQ ID NO: 21)
ATGGACTATAAGGACCACGACGGAGACTACAAGGATCATGATATTGATTA
```

-continued

```
CAAAGACGATGACGATAAGATGGCCCCAAAGAAGAAGCGGAAGGTCGGTA

TCCACGGAGTCCCAGCAGCCGTAGATTTGAGAACTTTGGGATATTCACAG

CAGCAGCAGGAAAAGATCAAGCCCAAAGTGAGGTCGACAGTCGCGCAGCA

TCACGAAGCGCTGGTGGGTCATGGGTTTACACATGCCCACATCGTAGCCT

TGTCGCAGCACCCTGCAGCCCTTGGCACGGTCGCCGTCAAGTACCAGGAC

ATGATTGCGGCGTTGCCGGAAGCCACACATGAGGCGATCGTCGGTGTGGG

GAAACAGTGGAGCGGAGCCCGAGCGCTTGAGGCCCTGTTGACGGTCGCGG

GAGAGCTGAGAGGGCCTCCCCTTCAGCTGGACACGGGCCAGTTGCTGAAG

ATCGCGAAGCGGGGAGGAGTCACGGCGGTCGAGGCGGTGCACGCGTGGCG

CAATGCGCTCACGGGAGCACCCCTCAACCTGACCCCAGAGCAGGTCGTGG

CAATTGCGAGCCATGACGGGGGAAAGCAGGCACTCGAAACCGTCCAGAGG

TTGCTGCCTGTGCTGTGCCAAGCGCACGGACTTACGCCAGAGCAGGTCGT

GGCAATTGCGAGCAACATCGGGGGAAAGCAGGCACTCGAAACCGTCCAGA

GGTTGCTGCCTGTGCTGTGCCAAGCGCACGGACTAACCCCAGAGCAGGTC

GTGGCAATTGCGAGCCATGACGGGGGAAAGCAGGCACTCGAAACCGTCCA

GAGGTTGCTGCCTGTGCTGTGCCAAGCGCACGGGTTGACCCCAGAGCAGG

TCGTGGCAATTGCGAGCAACGGAGGGGGAAAGCAGGCACTCGAAACCGTC

CAGAGGTTGCTGCCTGTGCTGTGCCAAGCGCACGGCCTGACCCCAGAGCA

GGTCGTGGCAATTGCGAGCAACGGAGGGGGAAAGCAGGCACTCGAAACCG

TCCAGAGGTTGCTGCCTGTGCTGTGCCAAGCGCACGGACTGACACCAGAG

CAGGTCGTGGCAATTGCGAGCCATGACGGGGGAAAGCAGGCACTCGAAAC

CGTCCAGAGGTTGCTGCCTGTGCTGTGCCAAGCGCACGGACTTACACCCG

AACAAGTCGTGGCAATTGCGAGCAACATCGGGGGAAAGCAGGCACTCGAA

ACCGTCCAGAGGTTGCTGCCTGTGCTGTGCCAAGCGCACGGACTTACGCC

AGAGCAGGTCGTGGCAATTGCGAGCAACATCGGGGGAAAGCAGGCACTCG

AAACCGTCCAGAGGTTGCTGCCTGTGCTGTGCCAAGCGCACGGACTAACC

CCAGAGCAGGTCGTGGCAATTGCGAGCAACCACGGGGGAAAGCAGGCACT

CGAAACCGTCCAGAGGTTGCTGCCTGTGCTGTGCCAAGCGCACGGGTTGA

CCCCAGAGCAGGTCGTGGCAATTGCGAGCAACATCGGGGGAAAGCAGGCA

CTCGAAACCGTCCAGAGGTTGCTGCCTGTGCTGTGCCAAGCGCACGGCCT

GACCCCAGAGCAGGTCGTGGCAATTGCGAGCAACGGAGGGGGAAAGCAGG

CACTCGAAACCGTCCAGAGGTTGCTGCCTGTGCTGTGCCAAGCGCACGGA

CTGACACCAGAGCAGGTCGTGGCAATTGCGAGCAACGGAGGGGGAAAGCA

GGCACTCGAAACCGTCCAGAGGTTGCTGCCTGTGCTGTGCCAAGCGCACG

GCCTCACCCCAGAGCAGGTCGTGGCAATTGCGAGCCATGACGGGGGAAAG

CAGGCACTCGAAACCGTCCAGAGGTTGCTGCCTGTGCTGTGCCAAGCGCA

CGGACTTACGCCAGAGCAGGTCGTGGCAATTGCGAGCAACGGAGGGGGAA

AGCAGGCACTCGAAACCGTCCAGAGGTTGCTGCCTGTGCTGTGCCAAGCG

CACGGACTAACCCCAGAGCAGGTCGTGGCAATTGCGAGCAACATCGGGGG

AAAGCAGGCACTCGAAACCGTCCAGAGGTTGCTGCCTGTGCTGTGCCAAG

CGCACGGGTTGACCCCAGAGCAGGTCGTGGCAATTGCGAGCCATGACGGG
```

-continued

```
GGAAAGCAGGCACTCGAAACCGTCCAGAGGTTGCTGCCTGTGCTGTGCCA
AGCGCACGGCCTGACCCCAGAGCAGGTCGTGGCAATTGCGAGCAACCACG
GGGGAAAGCAGGCACTCGAAACCGTCCAGAGGTTGCTGCCTGTGCTGTGC
CAAGCGCACGGACTGACACCAGAGCAGGTCGTGGCAATTGCGAGCAACCA
CGGGGGAAAGCAGGCACTCGAAACCGTCCAGAGGTTGCTGCCTGTGCTGT
GCCAAGCGCACGGACTCACGCCTGAGCAGGTAGTGGCTATTGCATCCAAC
ATCGGGGGCAGACCCGCACTGGAGTCAATCGTGGCCCAGCTTTCGAGGCC
GGACCCCGCGCTGGCCGCACTCACTAATGATCATCTTGTAGCGCTGGCCT
GCCTCGGCGGACGACCCGCCTTGGATGCGGTGAAGAAGGGGCTCCCGCAC
GCGCCTGCATTGATTAAGCGGACCAACAGAAGGATTCCCGAGAGGACATC
ACATCGAGTGGCAGGCCTGCAGGGAAGTGGAAGTATGGTGAGCAAGGGCG
AGGAGCTGTTCACCGGGGTGGTGCCCATCCTGGTCGAGCTGGACGGCGAC
GTAAACGGCCACAAGTTCAGCGTGTCCGGCGAGGGCGAGGGCGATGCCAC
CTACGGCAAGCTGACCCTGAAGCTGATCTGCACCACCGGCAAGCTGCCCG
TGCCCTGGCCCACCCTCGTGACCACCCTGGGCTACGGCCTGCAGTGCTTC
GCCCGCTACCCCGACCACATGAAGCAGCACGACTTCTTCAAGTCCGCCAT
GCCCGAAGGCTACGTCCAGGAGCGCACCATCTTCTTCAAGGACGACGGCA
ACTACAAGACCCGCGCCGAGGTGAAGTTCGAGGGCGACACCCTGGTGAAC
CGCATCGAGCTGAAGGGCATCGACTTCAAGGAGGACGGCAACATCCTGGG
GCACAAGCTGGAGTACAACTACAACAGCCACAACGTCTATATCACCGCCG
ACAAGCAGAAGAACGGCATCAAGGCCAACTTCAAGATCCGCCACAACATC
GAGGACGGCGGCGTGCAGCTCGCCGACCACTACCAGCAGAACACCCCCAT
CGGCGACGGCCCCGTGCTGCTGCCCGACAACCACTACCTGAGCTACCAGT
CCAAGCTGAGCAAAGACCCCAACGAGAAGCGCGATCACATGGTCCTGCTG
GAGTTCGTGACCGCCGCCGGGATCACTCTCGGCATGGACGAGCTGTACAA
GTAG.
```

In one embodiment, the present invention contemplates a plasmid comprising a nucleic acid encoding a Cen18 probe having the sequence of:

```
                                      (SEQ ID NO: 22)
ATGGACTATAAGGACCACGACGGAGACTACAAGGATCATGATATTGATTA
CAAAGACGATGACGATAAGATGGCCCCAAAGAAGAAGCGGAAGGTCGGTA
TCCACGGAGTCCCAGCAGCCGTAGATTTGAGAACTTTGGGATATTCACAG
CAGCAGCAGGAAAAGATCAAGCCCAAAGTGAGGTCGACAGTCGCGCAGCA
TCACGAAGCGCTGGTGGGTCATGGGTTTACACATGCCCACATCGTAGCCT
TGTCGCAGCACCCTGCAGCCCTTGGCACGGTCGCCGTCAAGTACCAGGAC
ATGATTGCGGCGTTGCCGGAAGCCACACATGAGGCGATCGTCGGTGTGGG
GAAACAGTGGAGCGGAGCCCGAGCGCTTGAGGCCCTGTTGACGGTCGCGG
GAGAGCTGAGAGGGCCTCCCCTTCAGCTGGACACGGGCCAGTTGCTGAAG
ATCGCGAAGCGGGGAGGAGTCACGGCGGTCGAGGCGGTGCACGCGTGGCG
CAATGCGCTCACGGGAGCACCCCTCAACCTGACCCCAGAGCAGGTCGTGG
```

-continued

```
CAATTGCGAGCAACGGAGGGGGAAAGCAGGCACTCGAAACCGTCCAGAGG
TTGCTGCCTGTGCTGTGCCAAGCGCACGGACTTACGCCAGAGCAGGTCGT
GGCAATTGCGAGCAACCACGGGGGAAAGCAGGCACTCGAAACCGTCCAGA
GGTTGCTGCCTGTGCTGTGCCAAGCGCACGGACTAACCCCAGAGCAGGTC
GTGGCAATTGCGAGCAACATCGGGGGAAAGCAGGCACTCGAAACCGTCCA
GAGGTTGCTGCCTGTGCTGTGCCAAGCGCACGGGTTGACCCCAGAGCAGG
TCGTGGCAATTGCGAGCAACATCGGGGGAAAGCAGGCACTCGAAACCGTC
CAGAGGTTGCTGCCTGTGCTGTGCCAAGCGCACGGCCTGACCCCAGAGCA
GGTCGTGGCAATTGCGAGCCATGACGGGGGAAAGCAGGCACTCGAAACCG
TCCAGAGGTTGCTGCCTGTGCTGTGCCAAGCGCACGGACTGACACCAGAG
CAGGTCGTGGCAATTGCGAGCCATGACGGGGGAAAGCAGGCACTCGAAAC
CGTCCAGAGGTTGCTGCCTGTGCTGTGCCAAGCGCACGGACTTACACCCG
AACAAGTCGTGGCAATTGCGAGCAACATCGGGGGAAAGCAGGCACTCGAA
ACCGTCCAGAGGTTGCTGCCTGTGCTGTGCCAAGCGCACGGACTTACGCC
AGAGCAGGTCGTGGCAATTGCGAGCCATGACGGGGGAAAGCAGGCACTCG
AAACCGTCCAGAGGTTGCTGCCTGTGCTGTGCCAAGCGCACGGACTAACC
CCAGAGCAGGTCGTGGCAATTGCGAGCCATGACGGGGGAAAGCAGGCACT
CGAAACCGTCCAGAGGTTGCTGCCTGTGCTGTGCCAAGCGCACGGGTTGA
CCCCAGAGCAGGTCGTGGCAATTGCGAGCAACCACGGGGGAAAGCAGGCA
CTCGAAACCGTCCAGAGGTTGCTGCCTGTGCTGTGCCAAGCGCACGGCCT
GACCCCAGAGCAGGTCGTGGCAATTGCGAGCAACGGAGGGGGAAAGCAGG
CACTCGAAACCGTCCAGAGGTTGCTGCCTGTGCTGTGCCAAGCGCACGGA
CTGACACCAGAGCAGGTCGTGGCAATTGCGAGCAACGGAGGGGGAAAGCA
GGCACTCGAAACCGTCCAGAGGTTGCTGCCTGTGCTGTGCCAAGCGCACG
GCCTCACCCCAGAGCAGGTCGTGGCAATTGCGAGCAACGGAGGGGGAAAG
CAGGCACTCGAAACCGTCCAGAGGTTGCTGCCTGTGCTGTGCCAAGCGCA
CGGACTTACGCCAGAGCAGGTCGTGGCAATTGCGAGCAACGGAGGGGGAA
AGCAGGCACTCGAAACCGTCCAGAGGTTGCTGCCTGTGCTGTGCCAAGCG
CACGGACTAACCCCAGAGCAGGTCGTGGCAATTGCGAGCAACCACGGGGG
AAAGCAGGCACTCGAAACCGTCCAGAGGTTGCTGCCTGTGCTGTGCCAAG
TCGCACGGGTTGACCCCAGAGCAGGCGTGGCAATTGCGAGCAACATCGGG
GGAAAGCAGGCACTCGAAACCGTCCAGAGGTTGCTGCCTGTGCTGTGCCA
AGCGCACGGCCTGACCCCAGAGCAGGTCGTGGCAATTGCGAGCAACATCG
GGGGAAAGCAGGCACTCGAAACCGTCCAGAGGTTGCTGCCTGTGCTGTGC
CAAGCGCACGGACTGACACCAGAGCAGGTCGTGGCAATTGCGAGCAACCA
CGGGGGAAAGCAGGCACTCGAAACCGTCCAGAGGTTGCTGCCTGTGCTGT
GCCAAGCGCACGGACTCACGCCTGAGCAGGTAGTGGCTATTGCATCCaac
cacGGGGGCAGACCCGCACTGGAGTCAATCGTGGCCCAGCTTTCGAGGCC
GGACCCCGCGCTGGCCGCACTCACTAATGATCATCTTGTAGCGCTGGCCT
GCCTCGGCGGACGACCCGCCTTGGATGCGGTGAAGAAGGGGCTCCCGCAC
```

-continued

```
GCGCCTGCATTGATTAAGCGGACCAACAGAAGGATTCCCGAGAGGACATC
ACATCGAGTGGCAGGCCTGCAGGGAAGTGGAAGTATGGTGAGCAAGGGCG
AGGAGCTGTTCACCGGGGTGGTGCCCATCCTGGTCGAGCTGGACGGCGAC
TGTAAACGGCCACAAGTTCAGCGTGCCGGCGAGGGCGAGGGCGATGCCAC
CTACGGCAAGCTGACCCTGAAGCTGATCTGCACCACCGGCAAGCTGCCCG
TGCCCTGGCCCACCCTCGTGACCACCCTGGGCTACGGCCTGCAGTGCTTC
GCCCGCTACCCCGACCACATGAAGCAGCACGACTTCTTCAAGTCCGCCAT
GCCCGAAGGCTACGTCCAGGAGCGCACCATCTTCTTCAAGGACGACGGCA
ACTACAAGACCCGCGCCGAGGTGAAGTTCGAGGGCGACACCCTGGTGAAC
CGCATCGAGCTGAAGGGCATCGACTTCAAGGAGGACGGCAACATCCTGGG
GCACAAGCTGGAGTACAACTACAACAGCCACAACGTCTATATCACCGCCG
ACAAGCAGAAGAACGGCATCAAGGCCAACTTCAAGATCCGCCACAACATC
GAGGACGGCGGCGTGCAGCTCGCCGACCACTACCAGCAGAACACCCCCAT
CGGCGACGGCCCCGTGCTGCTGCCCGACAACCACTACCTGAGCTACCAGT
CCAAGCTGAGCAAAGACCCCAACGAGAAGCGCGATCACATGGTCCTGCTG
AGAGTTCGTGACCGCCGCCGGGATCCTCTCGGCATGGACGAGCTGTACAA
GTAG.
```

In one embodiment, the present invention contemplates a plasmid comprising a nucleic acid encoding a Pan Cen probe having the sequence of:

```
                                              (SEQ ID NO: 23)
ATGGACTATAAGGACCACGACGGAGACTACAAGGATCATGATATTGATTA
CAAAGACGATGACGATAAGATGGCCCCAAAGAAGAAGCGGAAGGTCGGTA
TCCACGGAGTCCCAGCAGCCGTAGATTTGAGAACTTTGGGATATTCACAG
CAGCAGCAGGAAAAGATCAAGCCCAAAGTGAGGTCGACAGTCGCGCAGCA
TCACGAAGCGCTGGTGGGTCATGGGTTTACACATGCCCACATCGTAGCCT
TGTCGCAGCACCCTGCAGCCCTTGGCACGGTCGCCGTCAAGTACCAGGAC
ATGATTGCGGCGTTGCCGGAAGCCACACATGAGGCGATCGTCGGTGTGGG
GAAACAGTGGAGCGGAGCCCGAGCGCTTGAGGCCCTGTTGACGGTCGCGG
GAGAGCTGAGAGGGCCTCCCCTTCAGCTGGACACGGGCCAGTTGCTGAAG
ATCGCGAAGCGGGGAGGAGTCACGGCGGTCGAGGCGGTGCACGCGTGGCG
CAATGCGCTCACGGGAGCACCCCTCAACCTGACCCCAGAGCAGGTCGTGG
CAATTGCGAGCAACATCGGGGGAAAGCAGGCACTCGAAACCGTCCAGAGG
TTGCTGCCTGTGCTGTGCCAAGCGCACGGACTTACGCCAGAGCAGGTCGT
GGCAATTGCGAGCAACCACGGGGGAAAGCAGGCACTCGAAACCGTCCAGA
GGTTGCTGCCTGTGCTGTGCCAAGCGCACGGACTAACCCCAGAGCAGGTC
GTGGCAATTGCGAGCAACATCGGGGGAAAGCAGGCACTCGAAACCGTCCA
GAGGTTGCTGCCTGTGCTGTGCCAAGCGCACGGGTTGACCCCAGAGCAGG
TCGTGGCAATTGCGAGCCATGACGGGGGAAAGCAGGCACTCGAAACCGTC
CAGAGGTTGCTGCCTGTGCTGTGCCAAGCGCACGGCCTGACCCCAGAGCA
GGTCGTGGCAATTGCGAGCAACATCGGGGGAAAGCAGGCACTCGAAACCG
```

-continued

```
TCCAGAGGTTGCTGCCTGTGCTGTGCCAAGCGCACGGACTGACACCAGAG
CAGGTCGTGGCAATTGCGAGCAACCACGGGGGAAAGCAGGCACTCGAAAC
CGTCCAGAGGTTGCTGCCTGTGCTGTGCCAAGCGCACGGACTTACACCCG
AACAAGTCGTGGCAATTGCGAGCAACATCGGGGGAAAGCAGGCACTCGAA
ACCGTCCAGAGGTTGCTGCCTGTGCTGTGCCAAGCGCACGGACTTACGCC
AGAGCAGGTCGTGGCAATTGCGAGCAACATCGGGGGAAAGCAGGCACTCG
AAACCGTCCAGAGGTTGCTGCCTGTGCTGTGCCAAGCGCACGGACTAACC
CCAGAGCAGGTCGTGGCAATTGCGAGCAACCACGGGGGAAAGCAGGCACT
CGAAACCGTCCAGAGGTTGCTGCCTGTGCTGTGCCAAGCGCACGGGTTGA
CCCCAGAGCAGGTCGTGGCAATTGCGAGCCATGACGGGGGAAAGCAGGCA
CTCGAAACCGTCCAGAGGTTGCTGCCTGTGCTGTGCCAAGCGCACGGCCT
GACCCCAGAGCAGGTCGTGGCAATTGCGAGCAACATCGGGGGAAAGCAGG
CACTCGAAACCGTCCAGAGGTTGCTGCCTGTGCTGTGCCAAGCGCACGGA
CTGACACCAGAGCAGGTCGTGGCAATTGCGAGCAACGGAGGGGGAAAGCA
GGCACTCGAAACCGTCCAGAGGTTGCTGCCTGTGCTGTGCCAAGCGCACG
GCCTCACCCCAGAGCAGGTCGTGGCAATTGCGAGCAACGGAGGGGGAAAG
CAGGCACTCGAAACCGTCCAGAGGTTGCTGCCTGTGCTGTGCCAAGCGCA
CGGACTTACGCCAGAGCAGGTCGTGGCAATTGCGAGCCATGACGGGGGAA
AGCAGGCACTCGAAACCGTCCAGAGGTTGCTGCCTGTGCTGTGCCAAGCG
CACGGACTAACCCCAGAGCAGGTCGTGGCAATTGCGAGCAACGGAGGGGG
AAAGCAGGCACTCGAAACCGTCCAGAGGTTGCTGCCTGTGCTGTGCCAAG
CGCACGGGTTGACCCCAGAGCAGGTCGTGGCAATTGCGAGCCATGACGGG
GGAAAGCAGGCACTCGAAACCGTCCAGAGGTTGCTGCCTGTGCTGTGCCA
AGCGCACGGCCTGACCCCAGAGCAGGTCGTGGCAATTGCGAGCAACATCG
GGGGAAAGCAGGCACTCGAAACCGTCCAGAGGTTGCTGCCTGTGCTGTGC
CAAGCGCACGGACTGACACCAGAGCAGGTCGTGGCAATTGCGAGCAACCA
CGGGGGAAAGCAGGCACTCGAAACCGTCCAGAGGTTGCTGCCTGTGCTGT
GCCAAGCGCACGGACTCACGCCTGAGCAGGTAGTGGCTATTGCATCCaac
atcGGGGGCAGACCCGCACTGGAGTCAATCGTGGCCCAGCTTTCGAGGCC
GGACCCCGCGCTGGCCGCACTCACTAATGATCATCTTGTAGCGCTGGCCT
GCCTCGGCGGACGACCCGCCTTGGATGCGGTGAAGAAGGGGCTCCCGCAC
GCGCCTGCATTGATTAAGCGGACCAACAGAAGGATTCCCGAGAGGACATC
ACATCGAGTGGCAGGCCTGCAGGGAAGTGGAAGTATGGTGAGCAAGGGCG
AGGAGCTGTTCACCGGGGTGGTGCCCATCCTGGTCGAGCTGGACGGCGAC
GTAAACGGCCACAAGTTCAGCGTGTCCGGCGAGGGCGAGGGCGATGCCAC
CTACGGCAAGCTGACCCTGAAGCTGATCTGCACCACCGGCAAGCTGCCCG
TGCCCTGGCCCACCCTCGTGACCACCCTGGGCTACGGCCTGCAGTGCTTC
GCCCGCTACCCCGACCACATGAAGCAGCACGACTTCTTCAAGTCCGCCAT
GCCCGAAGGCTACGTCCAGGAGCGCACCATCTTCTTCAAGGACGACGGCA
ACTACAAGACCCGCGCCGAGGTGAAGTTCGAGGGCGACACCCTGGTGAAC
CGCATCGAGCTGAAGGGCATCGACTTCAAGGAGGACGGCAACATCCTGGG
```

-continued

```
GCACAAGCTGGAGTACAACTACAACAGCCACAACGTCTATATCACCGCCG

ACAAGCAGAAGAACGGCATCAAGGCCAACTTCAAGATCCGCCACAACATC

GAGGACGGCGGCGTGCAGCTCGCCGACCACTACCAGCAGAACACCCCCAT

CGGCGACGGCCCCGTGCTGCTGCCCGACAACCACTACCTGAGCTACCAGT

CCAAGCTGAGCAAAGACCCCAACGAGAAGCGCGATCACATGGTCCTGCTG

GAGTTCGTGACCGCCGCCGGGATCACTCTCGGCATGGACGAGCTGTACAA

GTAG.
```

Human chromosome 15 is one of five autosomes that carry a tandem array of repeated genes for ribosomal RNA in their acrocentric arms. Therefore, the juxtaposition of the centromere 15 and telomere signals near nucleoli in a number of cases is notable. See, FIG. 6, lower row, far right panel. Although it is not necessary to understand the mechanism of an invention, it is believed that this observation triangulates the centromere, the rDNA array (nucleolus) and the adjacent telomere in a spatial configuration compatible with the close distances among these three sites on chromosome 15. This suggests that the TALE-based method is accurately reading interphase genomic space.

In one embodiment, the present invention contemplates methods of detecting nucleic acid sequences using the specific nucleotide sequence recognition capacity of Transcription Activator-Like Effector (TALE's). In one embodiment, the method comprises a high affinity of TALE for double stranded DNA sequence targets. Although it is not necessary to understand the mechanism of an invention, it is believed that such sequence specificity and preferential recognition of targeted sequences in native DNA, the attachment of a fluorescent protein to a given TALE produces strong signals when a targeted sequence is tandemly repeated in the genome provided that a tethered fluorescent protein did not interfere with DNA sequence recognition in the TALE backbone. The present data is consistent with this belief. In some embodiments, the present invention contemplates specific target nucleic acids, located in either the centromere chromosome region and/or the teleomere chromosome region. See, Table I.

TABLE I

TALE Probe Targeting Of Centromere And/Or Teleomer Nucleic Acid Sequences

| TALE Probe Designation | Target Sequence | Sequence Identification Number |
|---|---|---|
| TALE-TelR6 | TAACCC | SEQ ID NO: 11 |
| TALE-TelR9 | TAACCCTAA | SEQ ID NO: 12 |
| TALE-TelR12 | TAACCCTAACCC | SEQ ID NO: 13 |
| TALE-TelR15 | TAACCCTAACCCTAA | SEQ ID NO: 14 |
| TALE-TelR20 | TAACCCTAACCCTAACCCTA | SEQ ID NO: 15 |
| TALE-TelL20 | TAGGGTTAGGGTTAGGGTTA | SEQ ID NO: 16 |
| TALE-PanCen | TAGACAGAAGCATTCTCAGA | SEQ ID NO: 17 |
| TALE-Cen15 | TCACTTCAAGATTCTACGGA | SEQ ID NO: 18 |
| TALE-Cen18 | TTGAACCACCGTTTTGAAGG | SEQ ID NO: 19 |

The compositions and methods disclosed herein label telomeric repeat double stranded DNA sequences, centromere sequence common to all chromosomes and centromere repeat sequences that are chromosome specific. It is expected that this method can be successful in detecting any other tandemly repeated DNA sequence element in any genome, including, but not limited to, genes for ribosomal RNA (known to undergo expansion or attrition) or ones implicated in human diseases prior to and after genomic expansion. Clinically, these methods are directly relevant to the study, diagnosis and treatment of trinucleotide repeat expansion diseases. Mirkin, S. M., "Expandable DNA repeats and human disease" *Nature* 447, 932-40 (2007). The ability of this method to label specific human chromosomes also offers unique opportunities to detect aberrant chromosomes. For example, the intranuclear dynamics of all three 21 chromosomes in human trisomy 21 patient cells may be labeled and tracked in relation to the territories they explore in these live cell studies. Antonarakis et al., "Chromosome 21 and down syndrome: from genomics to pathophysiology" *Nat. Rev. Genet.* 5, 725-38 (2004).

The highly sensitive sequence specificity of TALEs provide that the present embodiments may have broad clinical applications. Meckler et al., "Quantitative analysis of TALE-DNA interactions suggests polarity effects" *Nucleic Acids Res.* 41, 4118-28 (2013). The specific intensity of the TALE fluorescence and the genomic prevalence of specific targeted DNA sequences (down to possibly single-copy genes) are generally considered the primary considerations. Another consideration is that the presently disclosed TALE-based method docks (i.e., attaches, binds, etc) a protein (e.g., a TALE protein) with its attached fluorescent protein onto a specific DNA target sequence. Although the present data suggest that the fluorescent protein does not interfere with the binding of the TALE protein to the double stranded DNA target sequence, live cell applications of this method are interpreted by treating the fluorescent protein as "cargo".

In some embodiments, the fixed cell TALE-based method has a number of advantages over conventional methods known in the art. For example, the preparation of fluorescent TALEs by coupled in vitro transcription-translation is very time-efficient compared to the synthesis or commercial procurement of fluorescent oligonucleotide probes for conventional FISH. Even more advantageous is the very fast timescale of the TALE-based protocol. Starting with a coverglass culture, the steps of methanol fixation, rinse, probe incubation, and rinse takes less than one hour as compared to several hours in typical FISH methods. Further, the ability of TALE's to recognize targeted sequences in double-stranded DNA obviates the need for a DNA denaturation step. Non-bound TALE's require only a single, rapid wash for removal.

Preliminary studies using the presently disclosed method with human cells having differing telomere lengths suggested that the TALE-based signals may be useful to actually measure an average telomere length. Absent a direct determination of how many TALEs bind along the telomeric repeat in a truly quantitative way (i.e. with a linear relationship between telomere length and signal intensity over a wide range), it is clear that the signal intensities do correlate with the average telomere lengths of the cell lines. This result suggests that this method, with refinement, could have clinical applications in diagnostic situations where the average telomere length of a cell biopsy is relevant. Kim, et al., "Specific association of human telomere activity with immortal cells and cancer" *Science* 266, 2011-2015 (1994).

EXPERIMENTAL

Example I

Construction of TALEColor Plasmids

TALEs for TALEColor were assembled using the TAL effector toolbox obtained from Addgene (Cambridge, Mass.). Sanjana et al., "A transcription activator-like effector toolbox for genome engineering" *Nat. Protoc.* 7: 171-92 (2012). The destination vector for mammalian cell expression was derived from pcDNA4-TO-Hygromycin and contains a FLAG tag, the SV40 NLS and a truncated wild-type TALE backbone from the toolbox. Ma et al., "A highly efficient multifunctional tandem affinity purification approach applicable to diverse organisms" *Mol. Cell. Proteomics* 11, 501-11 (2012).

For specific telomere and centromere DNA probes, tandem repeats of 34-amino acid TALE monomers targeting 6-20 bp in the case of telomeric repeats and 20 bp in the case of the centromeric repeats were inserted into the destination vector to generate pcDNA4-TO-TelL20-mCerulean, pcDNA4-TO-TelL20-mVenus, pcDNA4-TO-TelR20-mCerulean, pcDNA4-TO-TelR20-mVenus, pcDNA4-TO-TelR20-mCherry for telomeres; and pcDNA4-TO-PanCen-mVenus, pcDNA4-TO-Cen18-mVenus, pcDNA4-TO-Cen15-mVenus for centromeres.

To produce TALEColors by in vitro coupled transcription-translation for the fixed cell application the 1-Step Human Coupled IVT Kit (Pierce, Rockford, Ill.) was used. TelR15 coding sequences were subcloned from the mammalian expression plasmid into in vitro translation plasmid pT7CFE1-His and generated pT7CFE1-TelR15-mTagBFP2, pT7CFE1-TelR15-mTFP1, pT7CFE1-TelR15-sfGFP, pT7CFE1-TelR15-YPet, pT7CFE1-TelR15-mCherry. To produce TelR15 with Green Lysine incorporation, TelR15 or TelR15-mCherry were subcloned into the bacterial expression plasmid pET30a to generate pET30a-TelR15 and pET30a-TelR15-mCherry. and these plasmids were then used to program coupled transcription-translation in the TnT T7 Quick Coupled kit (Promega, Madison, Wis.) in the presence of Green Lysine (Promega, Madison, Wis.).

Example II

Telomere and Centromere Target Sequences of TALEColors

TALEs were designed to target the human telomere repeat (TTAGGG) regions on either strand. The forward telomere target sequence (TelL) was the 20-mer TAGGGTTAGGGTTAGGGTTA (SEQ ID NO: 16). The reverse telomere target sequences (TelR) were the 20-mer TAACCCTAACCCTAACCCTA (SEQ ID NO: 15), the 15-mer TAACCCTAACCCTAA (SEQ ID NO: 14), the 12-mer TAACCCTAACCC (SEQ ID NO: 13), the 9-mer: TAACCCTAA (SEQ ID NO: 12) and the 6-mer: TAACCC (SEQ ID NO: 11). The pan-centromere target sequence, the chromosome 15-specific centromere target sequence and the chromosome 18-specific centromere target sequence were TAGACAGAAGCATTCTCAGA (SEQ ID NO: 17), TTGAACCACCGTTTTGAAGG (SEQ ID NO: 19) and TCACTTCAAGATTCTACGGA (SEQ ID NO: 18) respectively.

Example III

Cell Culture and Transfection of TALEColors

The U205, HeLa 1.311, HeLa S3 and IMR90 cells were cultured at 37° C. in Dulbecco-modified Eagle's Minimum Essential Medium (DMEM, Life Technologies, Grand Island, N.Y.) supplemented with 10% fetal bovine serum (FBS). RPE1 cells were cultured at 37° C. in DMEM:F12 medium supplemented with 10% FBS. Uetake et al., "Cell cycle progression and de novo centriole assembly after centrosomal removal in untransformed human cells" *J. Cell Biol.* 176, 173-82 (2007). For live imaging, cells were grown on Lab-Tek two-well coverglasses in HEPES-buffered DMEM containing 10% FBS, penicillin (100 units/ml) and streptomycin (100 μg/ml) and then overlaid with mineral oil. 50 ng of TALEColor plasmids were transfected using lipofectamine 2000 (Life Technologies, Grand Island, N.Y.) and the cells were incubated for another 24 hrs. The microscope stage incubation chamber was maintained at 37° C. as described previously. Jacobson et al., "RNA traffic and localization reported by fluorescence cytochemistry" *In: Analysis of mRNA Formation and Function*. Richter, J. D., ed. Academic Press, NY, pp. 341-359 (1997).

Phase-contrast and fluorescence microscopy were performed with a Leica DM-IRB inverted microscope equipped a mercury arc lamp, a 10-position filter wheel (Sutter Instrument, Novato, Calif.), CFP/YFP/HcRed filter set, GFP/DsRed filter set (Semrock, Rochester, N.Y.), a CCD camera (Photometrics, Tuscon, Ariz.) and MetaMorph acquisition software (Molecular Devices, San Jose, Calif.).

Example IV

DNA Labeling by TALEColors in Fixed Cells

Cells grown on coverslips were fixed in ice-cold methanol for 10 min at −20° C. All subsequent steps were carried out at room temperature. The fixed cells were incubated with 2N HCl for 5 min and then washed twice with PBS for 5 min each and then incubated with a given TALEColor probe as a 1:10 dilution from the coupled in vitro transcription-translation reactions mixtures for 30 min. The cells were then washed once with PBS for 5 min. Coverslips were mounted in Prolong Antifade (Molecular Probes, Eugene, Oreg.), and images were captured with the fluorescence microscopy system described above.

Example V

TALEColor Quantification and Single-Cell Imaging by Flow Cytometry

After labeling fixed cells with a given TALEColor probe as described above, they were trypsinized and centrifuged at 200 g for 5 min. and then washed once with PBS. The cell concentration was adjusted to $1\times10^7$/ml in PBS and ice-cold methanol was then added to a final concentration of 90% (vol/vol) with gentle mixing. $10^6$ cells were resuspended in 100 μl of 2N HCl and incubated at 5 min at ambient temperature, then washed 3 times with 100 μl PBS (300 g, 2 min.). The cells were resuspended and DNA was labeled by adding 100 μl PBS containing 1 μg/ml of DAPI or DRAQ5 for 10 min. and then washed twice with 100 μl PBS. Imaging flow cytometry was performed in the UMass Medical School FACS Core Facility with an Amnis FlowSight imaging cytometer (Amnis, Seattle, Wash.). GFP was excited at 488 nm and its emission was collected in a 505-560 nm channel; DAPI was excited at 405 nm and its emission collected using a 430-505 nm filter. DRAQ5 was excited at 642 nm and its emission collected using a 642-740 nm filter. Flow cytometry and quantitative imaging data were acquired and analyzed by INSPIRE and IDEAS software (Amnis, Seattle, Wash.), respectively.

I claim:

1. A fusion protein comprising a plurality of repeat amino acid sequences and a fluorescent protein, wherein said fusion protein is not coupled to a nuclease and at least one of said repeat amino acid sequences has a specific affinity for a telomere nucleic acid residue.

2. The fusion protein of claim 1, wherein said repeat amino acid sequences comprise:

```
                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,

                                   (SEQ ID NO: 25)
LTPEQVVAIASNGGGKQALETVQRLLPVLCQAHG,
and

                                   (SEQ ID NO: 26)
LTPEQVVAIASNIGG.
```

3. The fusion protein of claim 1, wherein said fusion protein comprises SEQ ID NO:2.

4. The fusion protein of claim 1, wherein said fusion protein comprises SEQ ID NO:3.

5. The fusion protein of claim 1, wherein said fusion protein comprises SEQ ID NO:4.

6. The fusion protein of claim 1, wherein said fusion protein comprises SEQ ID NO:5.

7. The fusion protein of claim 1, wherein said fusion protein comprises SEQ ID NO:6.

8. The fusion protein of claim 1, wherein said protein fusion comprises SEQ ID NO:7.

9. The fusion protein of claim 1, wherein said fluorescent protein is a green fluorescent protein.

10. The fusion protein of claim 1, wherein said fluorescent protein is an mCherry protein.

11. A fusion protein comprising a plurality of repeat amino acid sequences and a fluorescent protein, wherein said fusion protein is not coupled to a nuclease and at least one of said repeat amino acid sequences has a specific affinity for a centromere nucleic acid residue.

12. The fusion protein of claim 11, wherein said plurality of repeat amino acid sequences comprise:

```
                                   (SEQ ID NO: 25)
LTPEQVVAIASNGGGKQALETVQRLLPVLCQAHG,

                                   (SEQ ID NO: 27)
LTPEQVVAIASNHGGKQALETVQRLLPVLCQAHG,

                                   (SEQ ID NO: 24)
LTPEQVVAIASNIGGKQALETVQRLLPVLCQAHG,

                                    (SEQ ID NO: 1)
LTPEQVVAIASHDGGKQALETVQRLLPVLCQAHG,
and

                                  (SEQ ID NO: 29)
LTPEQVVAIASNHGG.
```

13. The fusion protein of claim 11 wherein said fusion protein comprises SEQ ID NO:8.

14. The fusion protein of claim 11, wherein said fusion protein comprises SEQ ID NO:9.

15. The fusion protein of claim 11, wherein said fusion protein comprises SEQ ID NO:10.

16. The fusion protein of claim 11, wherein said fluorescent protein is a green fluorescent protein.

17. The fusion protein of claim 11, wherein said fluorescent protein is an mCherry protein.

18. A telomere target nucleic acid sequence selected from the group consisting of

```
                              (SEQ ID NO: 11)
TAACCC

                              (SEQ ID NO: 12)
TAACCCTAA

                              (SEQ ID NO: 13)
TAACCCTAACCC,

                              (SEQ ID NO: 14)
TAACCCTAACCCTAA,

                              (SEQ ID NO: 15)
TAACCCTAACCCTAACCCTA,
and

                              (SEQ ID NO. 16)
TAGGGTTAGGGTTAGGGTTA.
```

19. A centromere target nucleic acid sequence selected from the group consisting of

```
                              (SEQ ID NO: 17)
TAGACAGAAGCATTCTCAGA

                              (SEQ ID NO: 18)
TCACTTCAAGATTCTACGGA,

                               (SEQ ID NO:19)
TTGAACCACCGTTTTGAAGG.
```

20. A composition comprising a peptide linked to a fluorescent protein and not attached to a nuclease, wherein said peptide is bound to a telomere target nucleic acid sequence.

21. The composition of claim 20, wherein said target nucleic acid sequence is selected from the group consisting of

```
                              (SEQ ID NO: 11)
TAACCC,

                              (SEQ ID NO: 12)
TAACCCTAA,

                              (SEQ ID NO: 13)
TAACCCTAACCC,

                              (SEQ ID NO: 14)
TAACCCTAACCCTAA,

                              (SEQ ED NO: 15)
TAACCCTAACCCTAACCCTA,
and

                              (SEQ ID NO. 16)
TAGGGTTAGGGTTAGGGTTA.
```

22. The composition of claim 20, wherein said peptide is selected from the group consisting of SEQ ID NO:2, SEQ ID NO:3, SEQ ID NO:4, SEQ ID NO:5, SEQ ID NO:6, and SEQ ID NO:7.

23. The composition of claim 20, wherein said telomere target nucleic acid sequence comprises double stranded deoxyribonucleic acid.

24. The composition of claim 20, wherein said composition further comprises a live cell.

25. The composition of claim 20, wherein said composition further comprises a fixed cell.

26. A composition comprising a peptide linked to a fluorescent protein and not attached to a nuclease, wherein said peptide is bound to a centromere target nucleic acid sequence.

27. The composition of claim 26, wherein said target nucleic acid sequence is selected from the group consisting of

```
                              (SEQ ID NO: 17)
TAGACAGAAGCATTCTCAGA,

                              (SEQ ID NO: 18)
TCACTTCAAGATTCTACGGA,

                              (SEQ ID NO: 19)
TTGAACCACCGTTTTGAAGG.
```

28. The composition of claim 26, wherein said peptide is selected from the group consisting of SEQ ID NO: 8, SEQ ID NO: 9 and SEQ ID NO: 10.

29. The composition of claim 26, wherein said target nucleic acid sequence is located a human chromosome selected from the group consisting of chromosome 15, chromosome 18 and chromosome 21.

30. The composition of claim 26, wherein said centromere target nucleic acid sequence comprises double stranded deoxyribonucleic acid.

31. The composition of claim 26, wherein said composition further comprises a live cell.

32. The composition of claim 26, wherein said composition further comprises a fixed cell.

* * * * *

SEQUENCE LISTING

```
<160> NUMBER OF SEQ ID NOS: 29

<210> SEQ ID NO 1
<211> LENGTH: 34
<212> TYPE: PRT
<213> ORGANISM: Artificial Sequence
<220> FEATURE:
<223> OTHER INFORMATION: Synthetic

<400> SEQUENCE: 1

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 2
<211> LENGTH: 371
<212> TYPE: PRT
<213> ORGANISM: Artificial Sequence
<220> FEATURE:
<223> OTHER INFORMATION: Synthetic

<400> SEQUENCE: 2

Met Ala Thr Thr His Met Gly Ser Gly Ile His Gly Val Pro Ala Ala
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
                85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu Thr Pro Glu Gln Val Val Ala
145                 150                 155                 160

Ile Ala Ser Asn Ile Gly Gly Lys Gln Ala Leu Glu Thr Val Gln Arg
                165                 170                 175

Leu Leu Pro Val Leu Cys Gln Ala His Gly Leu Thr Pro Glu Gln Val
            180                 185                 190

Val Ala Ile Ala Ser Asn Ile Gly Gly Lys Gln Ala Leu Glu Thr Val
        195                 200                 205

Gln Arg Leu Leu Pro Val Leu Cys Gln Ala His Gly Leu Thr Pro Glu
    210                 215                 220

Gln Val Val Ala Ile Ala Ser His Asp Gly Gly Lys Gln Ala Leu Glu
225                 230                 235                 240
```

```
Thr Val Gln Arg Leu Leu Pro Val Leu Cys Gln Ala His Gly Leu Thr
                245                 250                 255

Pro Glu Gln Val Val Ala Ile Ala Ser His Asp Gly Gly Lys Gln Ala
            260                 265                 270

Leu Glu Thr Val Gln Arg Leu Leu Pro Val Leu Cys Gln Ala His Gly
        275                 280                 285

Leu Thr Pro Glu Gln Val Val Ala Ile Ala Ser His Asp Gly Gly Arg
    290                 295                 300

Pro Ala Leu Glu Ser Ile Val Ala Gln Leu Ser Arg Pro Asp Pro Ala
305                 310                 315                 320

Leu Ala Ala Leu Thr Asn Asp His Leu Val Ala Leu Ala Cys Leu Gly
                325                 330                 335

Gly Arg Pro Ala Leu Asp Ala Val Lys Lys Gly Leu Pro His Ala Pro
            340                 345                 350

Ala Leu Ile Lys Arg Thr Asn Arg Arg Ile Pro Glu Arg Thr Ser His
        355                 360                 365

Arg Val Ala
    370


<210> SEQ ID NO 3
<211> LENGTH: 473
<212> TYPE: PRT
<213> ORGANISM: Artificial Sequence
<220> FEATURE:
<223> OTHER INFORMATION: Synthetic

<400> SEQUENCE: 3

Met Ala Thr Thr His Met Gly Ser Gly Ile His Gly Val Pro Ala Ala
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
                85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu Thr Pro Glu Gln Val Val Ala
145                 150                 155                 160

Ile Ala Ser Asn Ile Gly Gly Lys Gln Ala Leu Glu Thr Val Gln Arg
                165                 170                 175

Leu Leu Pro Val Leu Cys Gln Ala His Gly Leu Thr Pro Glu Gln Val
            180                 185                 190

Val Ala Ile Ala Ser Asn Ile Gly Gly Lys Gln Ala Leu Glu Thr Val
        195                 200                 205

Gln Arg Leu Leu Pro Val Leu Cys Gln Ala His Gly Leu Thr Pro Glu
    210                 215                 220
```

```
Gln Val Val Ala Ile Ala Ser His Asp Gly Gly Lys Gln Ala Leu Glu
225                 230                 235                 240

Thr Val Gln Arg Leu Leu Pro Val Leu Cys Gln Ala His Gly Leu Thr
                245                 250                 255

Pro Glu Gln Val Val Ala Ile Ala Ser His Asp Gly Gly Lys Gln Ala
            260                 265                 270

Leu Glu Thr Val Gln Arg Leu Leu Pro Val Leu Cys Gln Ala His Gly
        275                 280                 285

Leu Thr Pro Glu Gln Val Val Ala Ile Ala Ser His Asp Gly Gly Lys
    290                 295                 300

Gln Ala Leu Glu Thr Val Gln Arg Leu Leu Pro Val Leu Cys Gln Ala
305                 310                 315                 320

His Gly Leu Thr Pro Glu Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser Asn
        355                 360                 365

Ile Gly Gly Lys Gln Ala Leu Glu Thr Val Gln Arg Leu Leu Pro Val
    370                 375                 380

Leu Cys Gln Ala His Gly Leu Thr Pro Glu Gln Val Val Ala Ile Ala
385                 390                 395                 400

Ser Asn Ile Gly Gly Arg Pro Ala Leu Glu Ser Ile Val Ala Gln Leu
                405                 410                 415

Ser Arg Pro Asp Pro Ala Leu Ala Ala Leu Thr Asn Asp His Leu Val
            420                 425                 430

Ala Leu Ala Cys Leu Gly Gly Arg Pro Ala Leu Asp Ala Val Lys Lys
        435                 440                 445

Gly Leu Pro His Ala Pro Ala Leu Ile Lys Arg Thr Asn Arg Arg Ile
    450                 455                 460

Pro Glu Arg Thr Ser His Arg Val Ala
465                 470
```

```
<210> SEQ ID NO 4
<211> LENGTH: 575
<212> TYPE: PRT
<213> ORGANISM: Artificial Sequence
<220> FEATURE:
<223> OTHER INFORMATION: Synthetic

<400> SEQUENCE: 4

Met Ala Thr Thr His Met Gly Ser Gly Ile His Gly Val Pro Ala Ala
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
                85                  90                  95

Ser Gly Ala Arg Ala Leu Glu Ala Leu Leu Thr Val Ala Gly Glu Leu
            100                 105                 110
```

```
Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu Thr Pro Glu Gln Val Val Ala
145                 150                 155                 160

Ile Ala Ser Asn Ile Gly Gly Lys Gln Ala Leu Glu Thr Val Gln Arg
                165                 170                 175

Leu Leu Pro Val Leu Cys Gln Ala His Gly Leu Thr Pro Glu Gln Val
            180                 185                 190

Val Ala Ile Ala Ser Asn Ile Gly Gly Lys Gln Ala Leu Glu Thr Val
        195                 200                 205

Gln Arg Leu Leu Pro Val Leu Cys Gln Ala His Gly Leu Thr Pro Glu
    210                 215                 220

Gln Val Val Ala Ile Ala Ser His Asp Gly Gly Lys Gln Ala Leu Glu
225                 230                 235                 240

Thr Val Gln Arg Leu Leu Pro Val Leu Cys Gln Ala His Gly Leu Thr
                245                 250                 255

Pro Glu Gln Val Val Ala Ile Ala Ser His Asp Gly Gly Lys Gln Ala
            260                 265                 270

Leu Glu Thr Val Gln Arg Leu Leu Pro Val Leu Cys Gln Ala His Gly
        275                 280                 285

Leu Thr Pro Glu Gln Val Val Ala Ile Ala Ser His Asp Gly Gly Lys
    290                 295                 300

Gln Ala Leu Glu Thr Val Gln Arg Leu Leu Pro Val Leu Cys Gln Ala
305                 310                 315                 320

His Gly Leu Thr Pro Glu Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser Asn
        355                 360                 365

Ile Gly Gly Lys Gln Ala Leu Glu Thr Val Gln Arg Leu Leu Pro Val
    370                 375                 380

Leu Cys Gln Ala His Gly Leu Thr Pro Glu Gln Val Val Ala Ile Ala
385                 390                 395                 400

Ser Asn Ile Gly Gly Lys Gln Ala Leu Glu Thr Val Gln Arg Leu Leu
                405                 410                 415

Pro Val Leu Cys Gln Ala His Gly Leu Thr Pro Glu Gln Val Val Ala
            420                 425                 430

Ile Ala Ser His Asp Gly Gly Lys Gln Ala Leu Glu Thr Val Gln Arg
        435                 440                 445

Leu Leu Pro Val Leu Cys Gln Ala His Gly Leu Thr Pro Glu Gln Val
    450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Ala His Gly Leu Thr Pro Glu
                485                 490                 495

Gln Val Val Ala Ile Ala Ser His Asp Gly Gly Arg Pro Ala Leu Glu
            500                 505                 510

Ser Ile Val Ala Gln Leu Ser Arg Pro Asp Pro Ala Leu Ala Ala Leu
        515                 520                 525
```

```
Thr Asn Asp His Leu Val Ala Leu Ala Cys Leu Gly Gly Arg Pro Ala
    530                 535                 540

Leu Asp Ala Val Lys Lys Gly Leu Pro His Ala Pro Ala Leu Ile Lys
545                 550                 555                 560

Arg Thr Asn Arg Arg Ile Pro Glu Arg Thr Ser His Arg Val Ala
                565                 570                 575


<210> SEQ ID NO 5
<211> LENGTH: 677
<212> TYPE: PRT
<213> ORGANISM: Artificial Sequence
<220> FEATURE:
<223> OTHER INFORMATION: Synthetic

<400> SEQUENCE: 5

Met Ala Thr Thr His Met Gly Ser Gly Ile His Gly Val Pro Ala Ala
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
                85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu Thr Pro Glu Gln Val Val Ala
145                 150                 155                 160

Ile Ala Ser Asn Ile Gly Gly Lys Gln Ala Leu Glu Thr Val Gln Arg
                165                 170                 175

Leu Leu Pro Val Leu Cys Gln Ala His Gly Leu Thr Pro Glu Gln Val
            180                 185                 190

Val Ala Ile Ala Ser Asn Ile Gly Gly Lys Gln Ala Leu Glu Thr Val
        195                 200                 205

Gln Arg Leu Leu Pro Val Leu Cys Gln Ala His Gly Leu Thr Pro Glu
    210                 215                 220

Gln Val Val Ala Ile Ala Ser His Asp Gly Gly Lys Gln Ala Leu Glu
225                 230                 235                 240

Thr Val Gln Arg Leu Leu Pro Val Leu Cys Gln Ala His Gly Leu Thr
                245                 250                 255

Pro Glu Gln Val Val Ala Ile Ala Ser His Asp Gly Gly Lys Gln Ala
            260                 265                 270

Leu Glu Thr Val Gln Arg Leu Leu Pro Val Leu Cys Gln Ala His Gly
        275                 280                 285

Leu Thr Pro Glu Gln Val Val Ala Ile Ala Ser His Asp Gly Gly Lys
    290                 295                 300

Gln Ala Leu Glu Thr Val Gln Arg Leu Leu Pro Val Leu Cys Gln Ala
305                 310                 315                 320
```

```
His Gly Leu Thr Pro Glu Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser Asn
        355                 360                 365

Ile Gly Gly Lys Gln Ala Leu Glu Thr Val Gln Arg Leu Leu Pro Val
    370                 375                 380

Leu Cys Gln Ala His Gly Leu Thr Pro Glu Gln Val Val Ala Ile Ala
385                 390                 395                 400

Ser Asn Ile Gly Gly Lys Gln Ala Leu Glu Thr Val Gln Arg Leu Leu
                405                 410                 415

Pro Val Leu Cys Gln Ala His Gly Leu Thr Pro Glu Gln Val Val Ala
            420                 425                 430

Ile Ala Ser His Asp Gly Gly Lys Gln Ala Leu Glu Thr Val Gln Arg
        435                 440                 445

Leu Leu Pro Val Leu Cys Gln Ala His Gly Leu Thr Pro Glu Gln Val
    450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Ala His Gly Leu Thr Pro Glu
                485                 490                 495

Gln Val Val Ala Ile Ala Ser His Asp Gly Gly Lys Gln Ala Leu Glu
            500                 505                 510

Thr Val Gln Arg Leu Leu Pro Val Leu Cys Gln Ala His Gly Leu Thr
        515                 520                 525

Pro Glu Gln Val Val Ala Ile Ala Ser Asn Gly Gly Gly Lys Gln Ala
    530                 535                 540

Leu Glu Thr Val Gln Arg Leu Leu Pro Val Leu Cys Gln Ala His Gly
545                 550                 555                 560

Leu Thr Pro Glu Gln Val Val Ala Ile Ala Ser Asn Ile Gly Gly Lys
                565                 570                 575

Gln Ala Leu Glu Thr Val Gln Arg Leu Leu Pro Val Leu Cys Gln Ala
            580                 585                 590

His Gly Leu Thr Pro Glu Gln Val Val Ala Ile Ala Ser Asn Ile Gly
        595                 600                 605

Gly Arg Pro Ala Leu Glu Ser Ile Val Ala Gln Leu Ser Arg Pro Asp
    610                 615                 620

Pro Ala Leu Ala Ala Leu Thr Asn Asp His Leu Val Ala Leu Ala Cys
625                 630                 635                 640

Leu Gly Gly Arg Pro Ala Leu Asp Ala Val Lys Lys Gly Leu Pro His
                645                 650                 655

Ala Pro Ala Leu Ile Lys Arg Thr Asn Arg Arg Ile Pro Glu Arg Thr
            660                 665                 670

Ser His Arg Val Ala
        675
```

<210> SEQ ID NO 6
<211> LENGTH: 847
<212> TYPE: PRT
<213> ORGANISM: Artificial Sequence
<220> FEATURE:
<223> OTHER INFORMATION: Synthetic

<400> SEQUENCE: 6

```
Met Ala Thr Thr His Met Gly Ser Gly Ile His Gly Val Pro Ala Ala
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
                85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu Thr Pro Glu Gln Val Val Ala
145                 150                 155                 160

Ile Ala Ser Asn Ile Gly Gly Lys Gln Ala Leu Glu Thr Val Gln Arg
                165                 170                 175

Leu Leu Pro Val Leu Cys Gln Ala His Gly Leu Thr Pro Glu Gln Val
            180                 185                 190

Val Ala Ile Ala Ser Asn Ile Gly Gly Lys Gln Ala Leu Glu Thr Val
        195                 200                 205

Gln Arg Leu Leu Pro Val Leu Cys Gln Ala His Gly Leu Thr Pro Glu
    210                 215                 220

Gln Val Val Ala Ile Ala Ser His Asp Gly Gly Lys Gln Ala Leu Glu
225                 230                 235                 240

Thr Val Gln Arg Leu Leu Pro Val Leu Cys Gln Ala His Gly Leu Thr
                245                 250                 255

Pro Glu Gln Val Val Ala Ile Ala Ser His Asp Gly Gly Lys Gln Ala
            260                 265                 270

Leu Glu Thr Val Gln Arg Leu Leu Pro Val Leu Cys Gln Ala His Gly
        275                 280                 285

Leu Thr Pro Glu Gln Val Val Ala Ile Ala Ser His Asp Gly Gly Lys
    290                 295                 300

Gln Ala Leu Glu Thr Val Gln Arg Leu Leu Pro Val Leu Cys Gln Ala
305                 310                 315                 320

His Gly Leu Thr Pro Glu Gln Val Val Ala Ile Ala Ser Asn Gly Gly
                325                 330                 335

Gly Lys Gln Ala Leu Glu Thr Val Gln Arg Leu Leu Pro Val Leu Cys
            340                 345                 350

Gln Ala His Gly Leu Thr Pro Glu Gln Val Val Ala Ile Ala Ser Asn
        355                 360                 365

Ile Gly Gly Lys Gln Ala Leu Glu Thr Val Gln Arg Leu Leu Pro Val
    370                 375                 380

Leu Cys Gln Ala His Gly Leu Thr Pro Glu Gln Val Val Ala Ile Ala
385                 390                 395                 400

Ser Asn Ile Gly Gly Lys Gln Ala Leu Glu Thr Val Gln Arg Leu Leu
                405                 410                 415

Pro Val Leu Cys Gln Ala His Gly Leu Thr Pro Glu Gln Val Val Ala
```

```
            420                 425                 430

Ile Ala Ser His Asp Gly Gly Lys Gln Ala Leu Glu Thr Val Gln Arg
        435                 440                 445

Leu Leu Pro Val Leu Cys Gln Ala His Gly Leu Thr Pro Glu Gln Val
    450                 455                 460

Val Ala Ile Ala Ser His Asp Gly Gly Lys Gln Ala Leu Glu Thr Val
465                 470                 475                 480

Gln Arg Leu Leu Pro Val Leu Cys Gln Ala His Gly Leu Thr Pro Glu
                485                 490                 495

Gln Val Val Ala Ile Ala Ser His Asp Gly Gly Lys Gln Ala Leu Glu
            500                 505                 510

Thr Val Gln Arg Leu Leu Pro Val Leu Cys Gln Ala His Gly Leu Thr
        515                 520                 525

Pro Glu Gln Val Val Ala Ile Ala Ser Asn Gly Gly Gly Lys Gln Ala
    530                 535                 540

Leu Glu Thr Val Gln Arg Leu Leu Pro Val Leu Cys Gln Ala His Gly
545                 550                 555                 560

Leu Thr Pro Glu Gln Val Val Ala Ile Ala Ser Asn Ile Gly Gly Lys
                565                 570                 575

Gln Ala Leu Glu Thr Val Gln Arg Leu Leu Pro Val Leu Cys Gln Ala
            580                 585                 590

His Gly Leu Thr Pro Glu Gln Val Val Ala Ile Ala Ser Asn Ile Gly
        595                 600                 605

Gly Lys Gln Ala Leu Glu Thr Val Gln Arg Leu Leu Pro Val Leu Cys
    610                 615                 620

Gln Ala His Gly Leu Thr Pro Glu Gln Val Val Ala Ile Ala Ser His
625                 630                 635                 640

Asp Gly Gly Lys Gln Ala Leu Glu Thr Val Gln Arg Leu Leu Pro Val
                645                 650                 655

Leu Cys Gln Ala His Gly Leu Thr Pro Glu Gln Val Val Ala Ile Ala
            660                 665                 670

Ser His Asp Gly Gly Lys Gln Ala Leu Glu Thr Val Gln Arg Leu Leu
        675                 680                 685

Pro Val Leu Cys Gln Ala His Gly Leu Thr Pro Glu Gln Val Val Ala
    690                 695                 700

Ile Ala Ser His Asp Gly Gly Lys Gln Ala Leu Glu Thr Val Gln Arg
705                 710                 715                 720

Leu Leu Pro Val Leu Cys Gln Ala His Gly Leu Thr Pro Glu Gln Val
                725                 730                 735

Val Ala Ile Ala Ser Asn Gly Gly Gly Lys Gln Ala Leu Glu Thr Val
            740                 745                 750

Gln Arg Leu Leu Pro Val Leu Cys Gln Ala His Gly Leu Thr Pro Glu
        755                 760                 765

Gln Val Val Ala Ile Ala Ser Asn Ile Gly Gly Arg Pro Ala Leu Glu
    770                 775                 780

Ser Ile Val Ala Gln Leu Ser Arg Pro Asp Pro Ala Leu Ala Ala Leu
785                 790                 795                 800

Thr Asn Asp His Leu Val Ala Leu Ala Cys Leu Gly Gly Arg Pro Ala
                805                 810                 815

Leu Asp Ala Val Lys Lys Gly Leu Pro His Ala Pro Ala Leu Ile Lys
            820                 825                 830

Arg Thr Asn Arg Arg Ile Pro Glu Arg Thr Ser His Arg Val Ala
        835                 840                 845
```

<210> SEQ ID NO 7
<211> LENGTH: 831
<212> TYPE: PRT
<213> ORGANISM: Artificial Sequence
<220> FEATURE:
<223> OTHER INFORMATION: Synthetic

<400> SEQUENCE: 7

```
Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn His Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn His Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn His Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365
```

```
Leu Cys Gln Ala His Gly Leu Thr Pro Glu Gln Val Val Ala Ile Ala
    370                 375                 380

Ser Asn His Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn His Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn His Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser Asn Ile Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Glu Gln Val Val Ala Ile Ala Ser Asn His Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

His Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655

Ser Asn His Gly Gly Lys Gln Ala Leu Glu Thr Val Gln Arg Leu Leu
            660                 665                 670

Pro Val Leu Cys Gln Ala His Gly Leu Thr Pro Glu Gln Val Val Ala
        675                 680                 685

Ile Ala Ser Asn Gly Gly Gly Lys Gln Ala Leu Glu Thr Val Gln Arg
    690                 695                 700

Leu Leu Pro Val Leu Cys Gln Ala His Gly Leu Thr Pro Glu Gln Val
705                 710                 715                 720

Val Ala Ile Ala Ser Asn Gly Gly Gly Lys Gln Ala Leu Glu Thr Val
                725                 730                 735

Gln Arg Leu Leu Pro Val Leu Cys Gln Ala His Gly Leu Thr Pro Glu
            740                 745                 750

Gln Val Val Ala Ile Ala Ser Asn Ile Gly Gly Arg Pro Ala Leu Glu
        755                 760                 765

Ser Ile Val Ala Gln Leu Ser Arg Pro Asp Pro Ala Leu Ala Ala Leu
    770                 775                 780
```

```
Thr Asn Asp His Leu Val Ala Leu Ala Cys Leu Gly Gly Arg Pro Ala
785                 790                 795                 800

Leu Asp Ala Val Lys Lys Gly Leu Pro His Ala Pro Ala Leu Ile Lys
                805                 810                 815

Arg Thr Asn Arg Arg Ile Pro Glu Arg Thr Ser His Arg Val Ala
            820                 825                 830


<210> SEQ ID NO 8
<211> LENGTH: 831
<212> TYPE: PRT
<213> ORGANISM: Artificial Sequence
<220> FEATURE:
<223> OTHER INFORMATION: Synthetic

<400> SEQUENCE: 8

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Glu Gln Val Val Ala
    130                 135                 140

Ile Ala Ser Asn Ile Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn His Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn His Gly
305                 310                 315                 320
```

```
Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn His Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Glu Gln Val Val Ala Ile Ala Ser His Asp Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

Gly Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655

Ser His Asp Gly Gly Lys Gln Ala Leu Glu Thr Val Gln Arg Leu Leu
            660                 665                 670

Pro Val Leu Cys Gln Ala His Gly Leu Thr Pro Glu Gln Val Val Ala
        675                 680                 685

Ile Ala Ser Asn Ile Gly Gly Lys Gln Ala Leu Glu Thr Val Gln Arg
    690                 695                 700

Leu Leu Pro Val Leu Cys Gln Ala His Gly Leu Thr Pro Glu Gln Val
705                 710                 715                 720

Val Ala Ile Ala Ser Asn His Gly Gly Lys Gln Ala Leu Glu Thr Val
                725                 730                 735

Gln Arg Leu Leu Pro Val Leu Cys Gln Ala His Gly Leu Thr Pro Glu
```

```
            740                 745                 750

Gln Val Val Ala Ile Ala Ser Asn Ile Gly Gly Arg Pro Ala Leu Glu
        755                 760                 765

Ser Ile Val Ala Gln Leu Ser Arg Pro Asp Pro Ala Leu Ala Ala Leu
    770                 775                 780

Thr Asn Asp His Leu Val Ala Leu Ala Cys Leu Gly Gly Arg Pro Ala
785                 790                 795                 800

Leu Asp Ala Val Lys Lys Gly Leu Pro His Ala Pro Ala Leu Ile Lys
                805                 810                 815

Arg Thr Asn Arg Arg Ile Pro Glu Arg Thr Ser His Arg Val Ala
            820                 825                 830


<210> SEQ ID NO 9
<211> LENGTH: 831
<212> TYPE: PRT
<213> ORGANISM: Artificial Sequence
<220> FEATURE:
<223> OTHER INFORMATION: Synthetic

<400> SEQUENCE: 9

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Gly Lys
```

-continued

```
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn His Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser His Asp Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Glu Gln Val Val Ala Ile Ala Ser Asn Gly Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

Ile Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655

Ser His Asp Gly Gly Lys Gln Ala Leu Glu Thr Val Gln Arg Leu Leu
            660                 665                 670

Pro Val Leu Cys Gln Ala His Gly Leu Thr Pro Glu Gln Val Val Ala
        675                 680                 685

Ile Ala Ser Asn His Gly Gly Lys Gln Ala Leu Glu Thr Val Gln Arg
    690                 695                 700
```

```
Leu Leu Pro Val Leu Cys Gln Ala His Gly Leu Thr Pro Glu Gln Val
705                 710                 715                 720

Val Ala Ile Ala Ser Asn His Gly Gly Lys Gln Ala Leu Glu Thr Val
                725                 730                 735

Gln Arg Leu Leu Pro Val Leu Cys Gln Ala His Gly Leu Thr Pro Glu
            740                 745                 750

Gln Val Val Ala Ile Ala Ser Asn Ile Gly Gly Arg Pro Ala Leu Glu
        755                 760                 765

Ser Ile Val Ala Gln Leu Ser Arg Pro Asp Pro Ala Leu Ala Ala Leu
    770                 775                 780

Thr Asn Asp His Leu Val Ala Leu Ala Cys Leu Gly Gly Arg Pro Ala
785                 790                 795                 800

Leu Asp Ala Val Lys Lys Gly Leu Pro His Ala Pro Ala Leu Ile Lys
                805                 810                 815

Arg Thr Asn Arg Arg Ile Pro Glu Arg Thr Ser His Arg Val Ala
            820                 825                 830


<210> SEQ ID NO 10
<211> LENGTH: 831
<212> TYPE: PRT
<213> ORGANISM: Artificial Sequence
<220> FEATURE:
<223> OTHER INFORMATION: Synthetic

<400> SEQUENCE: 10

Val Asp Leu Arg Thr Leu Gly Tyr Ser Gln Gln Gln Gln Glu Lys Ile
1               5                   10                  15

Lys Pro Lys Val Arg Ser Thr Val Ala Gln His His Glu Ala Leu Val
            20                  25                  30

Gly His Gly Phe Thr His Ala His Ile Val Ala Leu Ser Gln His Pro
        35                  40                  45

Ala Ala Leu Gly Thr Val Ala Val Lys Tyr Gln Asp Met Ile Ala Ala
    50                  55                  60

Leu Pro Glu Ala Thr His Glu Ala Ile Val Gly Val Gly Lys Gln Trp
65                  70                  75                  80

Ser Gly Ala Arg Ala Leu Glu Ala Leu Leu Thr Val Ala Gly Glu Leu
                85                  90                  95

Arg Gly Pro Pro Leu Gln Leu Asp Thr Gly Gln Leu Leu Lys Ile Ala
            100                 105                 110

Lys Arg Gly Gly Val Thr Ala Val Glu Ala Val His Ala Trp Arg Asn
        115                 120                 125

Ala Leu Thr Gly Ala Pro Leu Asn Leu Thr Pro Glu Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn His Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Arg Leu Leu Pro Val Leu Cys Gln Ala His Gly Leu Thr
225                 230                 235                 240
```

```
Pro Glu Gln Val Val Ala Ile Ala Ser Asn Ile Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn His Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Glu Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser Asn Gly Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Glu Gln Val Val Ala Ile Ala Ser Asn Gly Gly
            580                 585                 590

Gly Lys Gln Ala Leu Glu Thr Val Gln Arg Leu Leu Pro Val Leu Cys
        595                 600                 605

Gln Ala His Gly Leu Thr Pro Glu Gln Val Val Ala Ile Ala Ser Asn
    610                 615                 620

His Gly Gly Lys Gln Ala Leu Glu Thr Val Gln Arg Leu Leu Pro Val
625                 630                 635                 640

Leu Cys Gln Ala His Gly Leu Thr Pro Glu Gln Val Val Ala Ile Ala
                645                 650                 655
```

```
Ser Asn Ile Gly Gly Lys Gln Ala Leu Glu Thr Val Gln Arg Leu Leu
            660                 665                 670

Pro Val Leu Cys Gln Ala His Gly Leu Thr Pro Glu Gln Val Val Ala
        675                 680                 685

Ile Ala Ser Asn Ile Gly Gly Lys Gln Ala Leu Glu Thr Val Gln Arg
    690                 695                 700

Leu Leu Pro Val Leu Cys Gln Ala His Gly Leu Thr Pro Glu Gln Val
705                 710                 715                 720

Val Ala Ile Ala Ser Asn His Gly Gly Lys Gln Ala Leu Glu Thr Val
                725                 730                 735

Gln Arg Leu Leu Pro Val Leu Cys Gln Ala His Gly Leu Thr Pro Glu
            740                 745                 750

Gln Val Val Ala Ile Ala Ser Asn His Gly Gly Arg Pro Ala Leu Glu
        755                 760                 765

Ser Ile Val Ala Gln Leu Ser Arg Pro Asp Pro Ala Leu Ala Ala Leu
    770                 775                 780

Thr Asn Asp His Leu Val Ala Leu Ala Cys Leu Gly Gly Arg Pro Ala
785                 790                 795                 800

Leu Asp Ala Val Lys Lys Gly Leu Pro His Ala Pro Ala Leu Ile Lys
                805                 810                 815

Arg Thr Asn Arg Arg Ile Pro Glu Arg Thr Ser His Arg Val Ala
            820                 825                 830
```

<210> SEQ ID NO 11
<211> LENGTH: 6
<212> TYPE: DNA
<213> ORGANISM: Artificial Sequence
<220> FEATURE:
<223> OTHER INFORMATION: Synthetic

<400> SEQUENCE: 11 taaccc 6

<210> SEQ ID NO 12
<211> LENGTH: 9
<212> TYPE: DNA
<213> ORGANISM: Artificial Sequence
<220> FEATURE:
<223> OTHER INFORMATION: Synthetic

<400> SEQUENCE: 12 taaccctaa 9

<210> SEQ ID NO 13
<211> LENGTH: 12
<212> TYPE: DNA
<213> ORGANISM: Artificial Sequence
<220> FEATURE:
<223> OTHER INFORMATION: Synthetic

<400> SEQUENCE: 13
taaccctaac cc 12

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
taaccctaac cctaa 15

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
taaccctaac cctaacccta 20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tagggttagg gttagggtta 20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tagacagaag cattctcaga 20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tcacttcaag attctacgga 20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ttgaaccacc gttttgaagg 20

<210> SEQ ID NO 20
<211> LENGTH: 2766
<212> TYPE: DNA
<213> ORGANISM: Artificial Sequence
<220> FEATURE:
<223> OTHER INFORMATION: Synthetic

<400> SEQUENCE: 20
atggccacca cccatatggg atccggtatc cacggagtcc cagcagccgt agatttgaga 60
actttgggat attcacagca gcagcaggaa aagatcaagc ccaaagtgag gtcgacagtc 120
gcgcagcatc acgaagcgct ggtgggtcat gggtttacac atgcccacat cgtagccttg 180
tcgcagcacc ctgcagccct tggcacggtc gccgtcaagt accaggacat gattgcggcg 240

```
ttgccggaag ccacacatga ggcgatcgtc ggtgtgggga aacagtggag cggagcccga    300
gcgcttgagg ccctgttgac ggtcgcggga gagctgagag ggcctcccct tcagctggac    360
acgggccagt tgctgaagat cgcgaagcgg ggaggagtca cggcggtcga ggcggtgcac    420
gcgtggcgca atgcgctcac gggagcaccc ctcaacctga ccccagagca ggtcgtggca    480
attgcgagca acatcggggg aaagcaggca ctcgaaaccg tccagaggtt gctgcctgtg    540
ctgtgccaag cgcacggact tacgccagag caggtcgtgg caattgcgag caacatcggg    600
ggaaagcagg cactcgaaac cgtccagagg ttgctgcctg tgctgtgcca agcgcacgga    660
ctaaccccag agcaggtcgt ggcaattgcg agccatgacg gggaaagca ggcactcgaa    720
accgtccaga ggttgctgcc tgtgctgtgc caagcgcacg ggttgacccc agagcaggtc    780
gtggcaattg cgagccatga cgggggaaag caggcactcg aaaccgtcca gaggttgctg    840
cctgtgctgt gccaagcgca cggcctgacc ccagagcagg tcgtggcaat tgcgagccat    900
gacgggggaa agcaggcact cgaaaccgtc cagaggttgc tgcctgtgct gtgccaagcg    960
cacggactga caccagagca ggtcgtggca attgcgagca acggaggggg aaagcaggca   1020
ctcgaaaccg tccagaggtt gctgcctgtg ctgtgccaag cgcacggact tacacccgaa   1080
caagtcgtgg caattgcgag caacatcggg ggaaagcagg cactcgaaac cgtccagagg   1140
ttgctgcctg tgctgtgcca agcgcacgga cttacgccag agcaggtcgt ggcaattgcg   1200
agcaacatcg gggaaagca ggcactcgaa accgtccaga ggttgctgcc tgtgctgtgc   1260
caagcgcacg gactaacccc agagcaggtc gtggcaattg cgagccatga cgggggaaag   1320
caggcactcg aaaccgtcca gaggttgctg cctgtgctgt gccaagcgca cgggttgacc   1380
ccagagcagg tcgtggcaat tgcgagccat gacgggggaa agcaggcact cgaaaccgtc   1440
cagaggttgc tgcctgtgct gtgccaagcg cacggcctga ccccagagca ggtcgtggca   1500
attgcgagcc atgacggggg aaagcaggca ctcgaaaccg tccagaggtt gctgcctgtg   1560
ctgtgccaag cgcacggact gacaccagag caggtcgtgg caattgcgag caacggaggg   1620
ggaaagcagg cactcgaaac cgtccagagg ttgctgcctg tgctgtgcca agcgcacggc   1680
ctcaccccag agcaggtcgt ggcaattgcg agcaacatcg gggaaagca ggcactcgaa   1740
accgtccaga ggttgctgcc tgtgctgtgc caagcgcacg gactcacgcc tgagcaggta   1800
gtggctattg catccaacat cgggggcaga cccgcactgg agtcaatcgt ggcccagctt   1860
tcgaggccgg accccgcgct ggccgcactc actaatgatc atcttgtagc gctggcctgc   1920
ctcggcggac gacccgcctt ggatgcggtg aagaaggggc tcccgcacgc gcctgcattg   1980
attaagcgga ccaacagaag gattcccgag aggacatcac atcgagtggc aggcctgcag   2040
ggaagtggaa tgcgtaaagg cgaagagctg ttcactggtg tcgtccctat tctggtggaa   2100
ctggatggtg atgtcaacgg tcataagttt tccgtgcgtg gcgagggtga aggtgacgca   2160
actaatggta aactgacgct gaagttcatc tgtactactg gtaaactgcc ggtaccttgg   2220
ccgactctgg taacgacgct gacttatggt gttcagtgct ttgctcgtta tccggaccat   2280
atgaagcagc atgacttctt caagtccgcc atgccggaag gctatgtgca ggaacgcacg   2340
atttccttta aggatgacgg cacgtacaaa acgcgtgcgg aagtgaaatt tgaaggcgat   2400
accctggtaa accgcattga gctgaaaggc attgacttta aagaagacgg caatatcctg   2460
ggccataagc tggaatacaa ttttaacagc cacaatgttt acatcaccgc cgataaacaa   2520
aaaaatggca ttaaagcgaa ttttaaaatt cgccacaacg tggaggatgg cagcgtgcag   2580
```

ctggctgatc actaccagca aaacactcca atcggtgatg gtcctgttct gctgccagac 2640
aatcactatc tgagcacgca aagcgttctg tctaaagatc cgaacgagaa acgcgatcat 2700
atggttctgc tggagttcgt aaccgcagcg ggcatcacgc atggtatgga tgaactgtac 2760
aaatag 2766

<210> SEQ ID NO 21
<211> LENGTH: 3354
<212> TYPE: DNA
<213> ORGANISM: Artificial Sequence
<220> FEATURE:
<223> OTHER INFORMATION: Synthetic

<400> SEQUENCE: 21
atggactata aggaccacga cggagactac aaggatcatg atattgatta caaagacgat 60
gacgataaga tggccccaaa gaagaagcgg aaggtcggta tccacggagt cccagcagcc 120
gtagatttga gaactttggg atattcacag cagcagcagg aaaagatcaa gcccaaagtg 180
aggtcgacag tcgcgcagca tcacgaagcg ctggtgggtc atgggtttac acatgcccac 240
atcgtagcct tgtcgcagca ccctgcagcc cttggcacgg tcgccgtcaa gtaccaggac 300
atgattgcgg cgttgccgga agccacacat gaggcgatcg tcggtgtggg gaaacagtgg 360
agcggagccc gagcgcttga ggccctgttg acggtcgcgg gagagctgag agggcctccc 420
cttcagctgg acacgggcca gttgctgaag atcgcgaagc ggggaggagt cacggcggtc 480
gaggcggtgc acgcgtggcg caatgcgctc acgggagcac ccctcaacct gaccccagag 540
caggtcgtgg caattgcgag ccatgacggg ggaaagcagg cactcgaaac cgtccagagg 600
ttgctgcctg tgctgtgcca agcgcacgga cttacgccag agcaggtcgt ggcaattgcg 660
agcaacatcg ggggaaagca ggcactcgaa accgtccaga ggttgctgcc tgtgctgtgc 720
caagcgcacg gactaacccc agagcaggtc gtggcaattg cgagccatga cgggggaaag 780
caggcactcg aaaccgtcca gaggttgctg cctgtgctgt gccaagcgca cgggttgacc 840
ccagagcagg tcgtggcaat tgcgagcaac ggagggggaa agcaggcact cgaaaccgtc 900
cagaggttgc tgcctgtgct gtgccaagcg cacggcctga ccccagagca ggtcgtggca 960
attgcgagca acggaggggg aaagcaggca ctcgaaaccg tccagaggtt gctgcctgtg 1020
ctgtgccaag cgcacggact gacaccagag caggtcgtgg caattgcgag ccatgacggg 1080
ggaaagcagg cactcgaaac cgtccagagg ttgctgcctg tgctgtgcca agcgcacgga 1140
cttacacccg aacaagtcgt ggcaattgcg agcaacatcg ggggaaagca ggcactcgaa 1200
accgtccaga ggttgctgcc tgtgctgtgc caagcgcacg gacttacgcc agagcaggtc 1260
gtggcaattg cgagcaacat cgggggaaag caggcactcg aaaccgtcca gaggttgctg 1320
cctgtgctgt gccaagcgca cggactaacc ccagagcagg tcgtggcaat tgcgagcaac 1380
cacgggggaa agcaggcact cgaaaccgtc cagaggttgc tgcctgtgct gtgccaagcg 1440
cacgggttga ccccagagca ggtcgtggca attgcgagca acatcggggg aaagcaggca 1500
ctcgaaaccg tccagaggtt gctgcctgtg ctgtgccaag cgcacggcct gaccccagag 1560
caggtcgtgg caattgcgag caacggaggg ggaaagcagg cactcgaaac cgtccagagg 1620
ttgctgcctg tgctgtgcca agcgcacgga ctgacaccag agcaggtcgt ggcaattgcg 1680
agcaacggag gggaaagca ggcactcgaa accgtccaga ggttgctgcc tgtgctgtgc 1740
caagcgcacg gcctcacccc agagcaggtc gtggcaattg cgagccatga cgggggaaag 1800
caggcactcg aaaccgtcca gaggttgctg cctgtgctgt gccaagcgca cggacttacg 1860

```
ccagagcagg tcgtggcaat tgcgagcaac ggagggggaa agcaggcact cgaaaccgtc   1920

cagaggttgc tgcctgtgct gtgccaagcg cacggactaa ccccagagca ggtcgtggca   1980

attgcgagca acatcggggg aaagcaggca ctcgaaaccg tccagaggtt gctgcctgtg   2040

ctgtgccaag cgcacgggtt gaccccagag caggtcgtgg caattgcgag ccatgacggg   2100

ggaaagcagg cactcgaaac cgtccagagg ttgctgcctg tgctgtgcca agcgcacggc   2160

ctgaccccag agcaggtcgt ggcaattgcg agcaaccacg gggaaagca ggcactcgaa    2220

accgtccaga ggttgctgcc tgtgctgtgc caagcgcacg gactgacacc agagcaggtc   2280

gtggcaattg cgagcaacca cgggggaaag caggcactcg aaaccgtcca gaggttgctg   2340

cctgtgctgt gccaagcgca cggactcacg cctgagcagg tagtggctat tgcatccaac   2400

atcgggggca gacccgcact ggagtcaatc gtggcccagc tttcgaggcc ggaccccgcg   2460

ctggccgcac tcactaatga tcatcttgta gcgctggcct gcctcggcgg acgacccgcc   2520

ttggatgcgg tgaagaaggg gctcccgcac gcgcctgcat tgattaagcg gaccaacaga   2580

aggattcccg agaggacatc acatcgagtg gcaggcctgc agggaagtgg aagtatggtg   2640

agcaagggcg aggagctgtt caccggggtg gtgcccatcc tggtcgagct ggacggcgac   2700

gtaaacggcc acaagttcag cgtgtccggc gagggcgagg gcgatgccac ctacggcaag   2760

ctgaccctga agctgatctg caccaccggc aagctgcccg tgccctggcc caccctcgtg   2820

accaccctgg gctacggcct gcagtgcttc gcccgctacc ccgaccacat gaagcagcac   2880

gacttcttca agtccgccat gcccgaaggc tacgtccagg agcgcaccat cttcttcaag   2940

gacgacggca actacaagac ccgcgccgag gtgaagttcg agggcgacac cctggtgaac   3000

cgcatcgagc tgaagggcat cgacttcaag gaggacggca acatcctggg gcacaagctg   3060

gagtacaact acaacagcca caacgtctat atcaccgccg acaagcagaa gaacggcatc   3120

aaggccaact tcaagatccg ccacaacatc gaggacggcg gcgtgcagct cgccgaccac   3180

taccagcaga acacccccat cggcgacggc cccgtgctgc tgcccgacaa ccactacctg   3240

agctaccagt ccaagctgag caaagacccc aacgagaagc gcgatcacat ggtcctgctg   3300

gagttcgtga ccgccgccgg gatcactctc ggcatggacg agctgtacaa gtag         3354
```

<210> SEQ ID NO 22
<211> LENGTH: 3354
<212> TYPE: DNA
<213> ORGANISM: Artificial Sequence
<220> FEATURE:
<223> OTHER INFORMATION: Synthetic

<400> SEQUENCE: 22

```
atggactata aggaccacga cggagactac aaggatcatg atattgatta caaagacgat     60

gacgataaga tggccccaaa gaagaagcgg aaggtcggta tccacggagt cccagcagcc    120

gtagatttga gaactttggg atattcacag cagcagcagg aaaagatcaa gcccaaagtg    180

aggtcgacag tcgcgcagca tcacgaagcg ctggtgggtc atgggtttac acatgcccac    240

atcgtagcct tgtcgcagca ccctgcagcc cttggcacgg tcgccgtcaa gtaccaggac    300

atgattgcgg cgttgccgga agccacacat gaggcgatcg tcggtgtggg gaaacagtgg    360

agcggagccc gagcgcttga ggccctgttg acggtcgcgg gagagctgag agggcctccc    420

cttcagctgg acacgggcca gttgctgaag atcgcgaagc ggggaggagt cacggcggtc    480

gaggcggtgc acgcgtggcg caatgcgctc acgggagcac ccctcaacct gaccccagag    540
```

```
caggtcgtgg caattgcgag caacggaggg ggaaagcagg cactcgaaac cgtccagagg    600
ttgctgcctg tgctgtgcca agcgcacgga cttacgccag agcaggtcgt ggcaattgcg    660
agcaaccacg gggaaagca ggcactcgaa accgtccaga ggttgctgcc tgtgctgtgc    720
caagcgcacg gactaacccc agagcaggtc gtggcaattg cgagcaacat cgggggaaag    780
caggcactcg aaaccgtcca gaggttgctg cctgtgctgt gccaagcgca cgggttgacc    840
ccagagcagg tcgtggcaat tgcgagcaac atcgggggaa agcaggcact cgaaaccgtc    900
cagaggttgc tgcctgtgct gtgccaagcg cacggcctga ccccagagca ggtcgtggca    960
attgcgagcc atgacggggg aaagcaggca ctcgaaaccg tccagaggtt gctgcctgtg   1020
ctgtgccaag cgcacggact gacaccagag caggtcgtgg caattgcgag ccatgacggg   1080
ggaaagcagg cactcgaaac cgtccagagg ttgctgcctg tgctgtgcca agcgcacgga   1140
cttacacccg aacaagtcgt ggcaattgcg agcaacatcg gggaaagca ggcactcgaa   1200
accgtccaga ggttgctgcc tgtgctgtgc caagcgcacg gacttacgcc agagcaggtc   1260
gtggcaattg cgagccatga cgggggaaag caggcactcg aaaccgtcca gaggttgctg   1320
cctgtgctgt gccaagcgca cggactaacc ccagagcagg tcgtggcaat tgcgagccat   1380
gacgggggaa agcaggcact cgaaaccgtc cagaggttgc tgcctgtgct gtgccaagcg   1440
cacgggttga ccccagagca ggtcgtggca attgcgagca accacggggg aaagcaggca   1500
ctcgaaaccg tccagaggtt gctgcctgtg ctgtgccaag cgcacggcct gaccccagag   1560
caggtcgtgg caattgcgag caacggaggg ggaaagcagg cactcgaaac cgtccagagg   1620
ttgctgcctg tgctgtgcca agcgcacgga ctgacaccag agcaggtcgt ggcaattgcg   1680
agcaacggag gggaaagca ggcactcgaa accgtccaga ggttgctgcc tgtgctgtgc   1740
caagcgcacg gcctcacccc agagcaggtc gtggcaattg cgagcaacgg agggggaaag   1800
caggcactcg aaaccgtcca gaggttgctg cctgtgctgt gccaagcgca cggacttacg   1860
ccagagcagg tcgtggcaat tgcgagcaac ggagggggaa agcaggcact cgaaaccgtc   1920
cagaggttgc tgcctgtgct gtgccaagcg cacggactaa ccccagagca ggtcgtggca   1980
attgcgagca accacggggg aaagcaggca ctcgaaaccg tccagaggtt gctgcctgtg   2040
ctgtgccaag cgcacgggtt gaccccagag caggtcgtgg caattgcgag caacatcggg   2100
ggaaagcagg cactcgaaac cgtccagagg ttgctgcctg tgctgtgcca agcgcacggc   2160
ctgaccccag agcaggtcgt ggcaattgcg agcaacatcg gggaaagca ggcactcgaa   2220
accgtccaga ggttgctgcc tgtgctgtgc caagcgcacg gactgacacc agagcaggtc   2280
gtggcaattg cgagcaacca cgggggaaag caggcactcg aaaccgtcca gaggttgctg   2340
cctgtgctgt gccaagcgca cggactcacg cctgagcagg tagtggctat tgcatccaac   2400
cacgggggca gacccgcact ggagtcaatc gtggcccagc tttcgaggcc ggaccccgcg   2460
ctggccgcac tcactaatga tcatcttgta gcgctggcct gcctcggcgg acgacccgcc   2520
ttggatgcgg tgaagaaggg gctcccgcac gcgcctgcat tgattaagcg gaccaacaga   2580
aggattcccg agaggacatc acatcgagtg gcaggcctgc agggaagtgg aagtatggtg   2640
agcaagggcg aggagctgtt caccggggtg gtgcccatcc tggtcgagct ggacggcgac   2700
gtaaacggcc acaagttcag cgtgtccggc gagggcgagg gcgatgccac ctacggcaag   2760
ctgaccctga agctgatctg caccaccggc aagctgcccg tgccctggcc caccctcgtg   2820
accaccctgg gctacggcct gcagtgcttc gcccgctacc ccgaccacat gaagcagcac   2880
gacttcttca agtccgccat gcccgaaggc tacgtccagg agcgcaccat cttcttcaag   2940
```

```
gacgacggca actacaagac ccgcgccgag gtgaagttcg agggcgacac cctggtgaac   3000

cgcatcgagc tgaagggcat cgacttcaag gaggacggca acatcctggg gcacaagctg   3060

gagtacaact acaacagcca caacgtctat atcaccgccg acaagcagaa gaacggcatc   3120

aaggccaact tcaagatccg ccacaacatc gaggacggcg gcgtgcagct cgccgaccac   3180

taccagcaga acacccccat cggcgacggc cccgtgctgc tgcccgacaa ccactacctg   3240

agctaccagt ccaagctgag caaagacccc aacgagaagc gcgatcacat ggtcctgctg   3300

gagttcgtga ccgccgccgg gatcactctc ggcatggacg agctgtacaa gtag         3354
```

<210> SEQ ID NO 23
<211> LENGTH: 3354
<212> TYPE: DNA
<213> ORGANISM: Artificial Sequence
<220> FEATURE:
<223> OTHER INFORMATION: Synthetic

<400> SEQUENCE: 23

```
atggactata aggaccacga cggagactac aaggatcatg atattgatta caaagacgat     60

gacgataaga tggccccaaa gaagaagcgg aaggtcggta tccacggagt cccagcagcc    120

gtagatttga gaactttggg atattcacag cagcagcagg aaaagatcaa gcccaaagtg    180

aggtcgacag tcgcgcagca tcacgaagcg ctggtgggtc atgggtttac acatgcccac    240

atcgtagcct tgtcgcagca ccctgcagcc cttggcacgg tcgccgtcaa gtaccaggac    300

atgattgcgg cgttgccgga agccacacat gaggcgatcg tcggtgtggg gaaacagtgg    360

agcggagccc gagcgcttga ggccctgttg acggtcgcgg gagagctgag agggcctccc    420

cttcagctgg acacgggcca gttgctgaag atcgcgaagc ggggaggagt cacggcggtc    480

gaggcggtgc acgcgtggcg caatgcgctc acgggagcac ccctcaacct gaccccagag    540

caggtcgtgg caattgcgag caacatcggg ggaaagcagg cactcgaaac cgtccagagg    600

ttgctgcctg tgctgtgcca agcgcacgga cttacgccag agcaggtcgt ggcaattgcg    660

agcaaccacg gggaaagca ggcactcgaa accgtccaga ggttgctgcc tgtgctgtgc     720

caagcgcacg gactaacccc agagcaggtc gtggcaattg cgagcaacat cgggggaaag    780

caggcactcg aaaccgtcca gaggttgctg cctgtgctgt gccaagcgca cgggttgacc    840

ccagagcagg tcgtggcaat tgcgagccat gacgggggaa agcaggcact cgaaaccgtc    900

cagaggttgc tgcctgtgct gtgccaagcg cacggcctga ccccagagca ggtcgtggca    960

attgcgagca acatcggggg aaagcaggca ctcgaaaccg tccagaggtt gctgcctgtg   1020

ctgtgccaag cgcacggact gacaccagag caggtcgtgg caattgcgag caaccacggg   1080

ggaaagcagg cactcgaaac cgtccagagg ttgctgcctg tgctgtgcca agcgcacgga   1140

cttacacccg aacaagtcgt ggcaattgcg agcaacatcg gggaaagca ggcactcgaa    1200

accgtccaga ggttgctgcc tgtgctgtgc caagcgcacg gacttacgcc agagcaggtc   1260

gtggcaattg cgagcaacat cgggggaaag caggcactcg aaaccgtcca gaggttgctg   1320

cctgtgctgt gccaagcgca cggactaacc ccagagcagg tcgtggcaat tgcgagcaac   1380

cacgggggaa agcaggcact cgaaaccgtc cagaggttgc tgcctgtgct gtgccaagcg   1440

cacgggttga ccccagagca ggtcgtggca attgcgagcc atgacggggg aaagcaggca   1500

ctcgaaaccg tccagaggtt gctgcctgtg ctgtgccaag cgcacggcct gaccccagag   1560

caggtcgtgg caattgcgag caacatcggg ggaaagcagg cactcgaaac cgtccagagg   1620
```

```
ttgctgcctg tgctgtgcca agcgcacgga ctgacaccag agcaggtcgt ggcaattgcg   1680
agcaacggag ggggaaagca ggcactcgaa accgtccaga ggttgctgcc tgtgctgtgc   1740
caagcgcacg gcctcacccc agagcaggtc gtggcaattg cgagcaacgg agggggaaag   1800
caggcactcg aaaccgtcca gaggttgctg cctgtgctgt gccaagcgca cggacttacg   1860
ccagagcagg tcgtggcaat tgcgagccat gacgggggaa agcaggcact cgaaaccgtc   1920
cagaggttgc tgcctgtgct gtgccaagcg cacggactaa ccccagagca ggtcgtggca   1980
attgcgagca acggaggggg aaagcaggca ctcgaaaccg tccagaggtt gctgcctgtg   2040
ctgtgccaag cgcacgggtt gaccccagag caggtcgtgg caattgcgag ccatgacggg   2100
ggaaagcagg cactcgaaac cgtccagagg ttgctgcctg tgctgtgcca agcgcacggc   2160
ctgaccccag agcaggtcgt ggcaattgcg agcaacatcg gggaaagca ggcactcgaa   2220
accgtccaga ggttgctgcc tgtgctgtgc caagcgcacg gactgacacc agagcaggtc   2280
gtggcaattg cgagcaacca cgggggaaag caggcactcg aaaccgtcca gaggttgctg   2340
cctgtgctgt gccaagcgca cggactcacg cctgagcagg tagtggctat tgcatccaac   2400
atcgggggca gacccgcact ggagtcaatc gtggcccagc tttcgaggcc ggaccccgcg   2460
ctggccgcac tcactaatga tcatcttgta gcgctggcct gcctcggcgg acgacccgcc   2520
ttggatgcgg tgaagaaggg gctcccgcac gcgcctgcat tgattaagcg gaccaacaga   2580
aggattcccg agaggacatc acatcgagtg gcaggcctgc agggaagtgg aagtatggtg   2640
agcaagggcg aggagctgtt caccggggtg gtgcccatcc tggtcgagct ggacggcgac   2700
gtaaacggcc acaagttcag cgtgtccggc gagggcgagg gcgatgccac ctacggcaag   2760
ctgaccctga agctgatctg caccaccggc aagctgcccg tgccctggcc caccctcgtg   2820
accaccctgg gctacggcct gcagtgcttc gcccgctacc ccgaccacat gaagcagcac   2880
gacttcttca agtccgccat gcccgaaggc tacgtccagg agcgcaccat cttcttcaag   2940
gacgacggca actacaagac ccgcgccgag gtgaagttcg agggcgacac cctggtgaac   3000
cgcatcgagc tgaagggcat cgacttcaag gaggacggca acatcctggg gcacaagctg   3060
gagtacaact acaacagcca caacgtctat atcaccgccg acaagcagaa gaacggcatc   3120
aaggccaact tcaagatccg ccacaacatc gaggacggcg gcgtgcagct cgccgaccac   3180
taccagcaga acacccccat cggcgacggc cccgtgctgc tgcccgacaa ccactacctg   3240
agctaccagt ccaagctgag caaagacccc aacgagaagc gcgatcacat ggtcctgctg   3300
gagttcgtga ccgccgccgg gatcactctc ggcatggacg agctgtacaa gtag         3354
```

<210> SEQ ID NO 24
<211> LENGTH: 34
<212> TYPE: PRT
<213> ORGANISM: Artificial Sequence
<220> FEATURE:
<223> OTHER INFORMATION: Synthetic

<400> SEQUENCE: 24

```
Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly
```

<210> SEQ ID NO 25
<211> LENGTH: 34

```
<212> TYPE: PRT
<213> ORGANISM: Artificial Sequence
<220> FEATURE:
<223> OTHER INFORMATION: Synthetic

<400> SEQUENCE: 25

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Leu Thr Pro Glu Gln Val Val Ala Ile Ala Ser Asn Ile Gly
1               5                   10


<210> SEQ ID NO 27
<211> LENGTH: 34
<212> TYPE: PRT
<213> ORGANISM: Artificial Sequence
<220> FEATURE:
<223> OTHER INFORMATION: Synthetic

<400> SEQUENCE: 27

Leu Thr Pro Glu Gln Val Val Ala Ile Ala Ser Asn His Gly Gly Lys
1               5                   10                  15

Gln Ala Leu Glu Thr Val Gln Arg Leu Leu Pro Val Leu Cys Gln Ala
            20                  25                  30

His Gly


<210> SEQ ID NO 28
<211> LENGTH: 35
<212> TYPE: PRT
<213> ORGANISM: Artificial Sequence
<220> FEATURE:
<223> OTHER INFORMATION: Synthetic

<400> SEQUENCE: 28

Leu Thr Pro Glu Gln Val Val Ala Ile Ala Ser Asn His Gly Gly Arg
1               5                   10                  15

Pro Ala Leu Glu Ser Ile Val Ala Gln Leu Ser Arg Pro Asp Pro Ala
            20                  25                  30

Leu Ala Ala
        35


<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Leu Thr Pro Glu Gln Val Val Ala Ile Ala Ser Asn His Gly Gly
1               5                   10                  15
```